United States Patent
Solem

(10) Patent No.: US 8,758,432 B2
(45) Date of Patent: Jun. 24, 2014

(54) BLOOD FLOW CONTROLLING APPARATUS

(75) Inventor: Jan O. Solem, Bjarred (SE)

(73) Assignee: Edwards Lifesciences AG, Nyon (CH)

( * ) Notice: Subject to any disclaimer, the term of this patent is extended or adjusted under 35 U.S.C. 154(b) by 0 days.

(21) Appl. No.: 13/531,184

(22) Filed: Jun. 22, 2012

(65) Prior Publication Data

US 2013/0090728 A1 Apr. 11, 2013

Related U.S. Application Data

(63) Continuation of application No. 11/407,582, filed on Apr. 19, 2006, now abandoned.

(30) Foreign Application Priority Data

Apr. 21, 2005 (SE) ........................................ 0500891

(51) Int. Cl.
*A61F 2/24* (2006.01)
(52) U.S. Cl.
USPC ........................... 623/2.17; 623/2.1; 623/1.26
(58) Field of Classification Search
CPC .... A61F 2/2412; A61F 2/2418; A61F 2/2448
USPC .............. 623/1.24–1.26, 2.1–2.19, 2.36, 2.37
See application file for complete search history.

(56) References Cited

U.S. PATENT DOCUMENTS

| | | | | |
|---|---|---|---|---|
| 6,482,228 | B1 * | 11/2002 | Norred | 623/2.17 |
| 7,404,824 | B1 * | 7/2008 | Webler et al. | 623/2.36 |
| 2003/0130731 | A1 * | 7/2003 | Vidlund et al. | 623/2.37 |
| 2005/0124969 | A1 * | 6/2005 | Fitzgerald et al. | 604/508 |
| 2006/0149360 | A1 * | 7/2006 | Schwammenthal et al. | 623/1.24 |

* cited by examiner

*Primary Examiner* — Jason-Dennis Stewart
(74) *Attorney, Agent, or Firm* — David L. Hauser

(57) ABSTRACT

A method for reducing regurgitation in a mitral valve using a blood flow controlling apparatus. The blood flow controlling apparatus comprises an anchoring means, preferably arranged to anchor the apparatus to a wall of the left ventricle. The blood flow controlling apparatus further comprises a valve means configured to expand in a direction transverse to blood flow. The valve means is preferably positioned within a native mitral valve and expands for making contact with the mitral valve leaflets during ventricular systole, thereby preventing blood from regurgitating back through the mitral valve into the left atrium. When blood flows from the left atrium to the left ventricle during ventricular diastole, the valve means collapses for allowing blood to pass freely through the mitral valve.

18 Claims, 73 Drawing Sheets

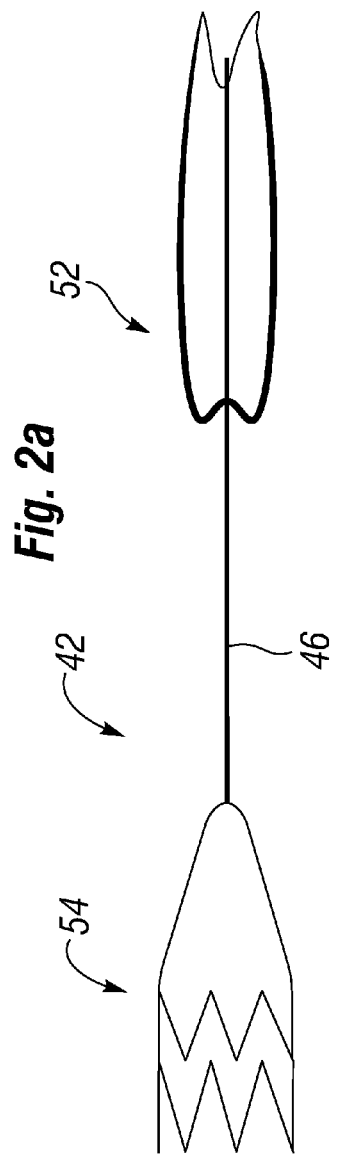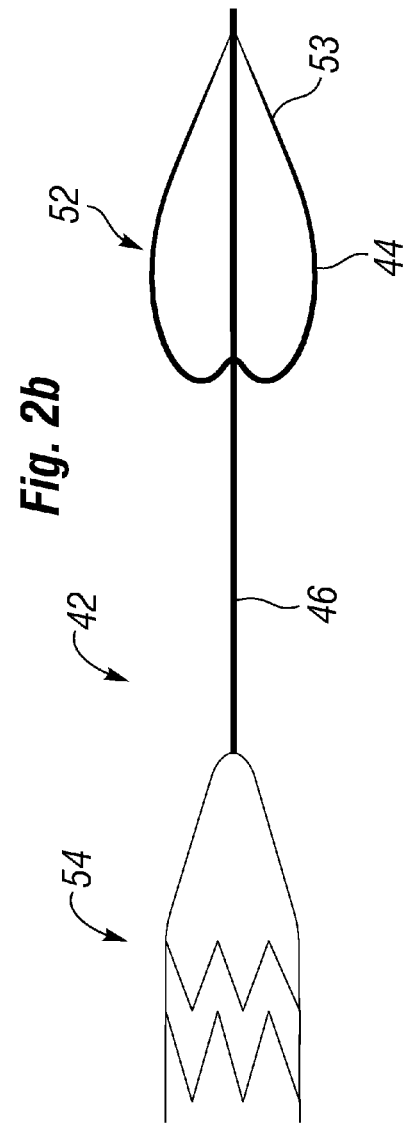

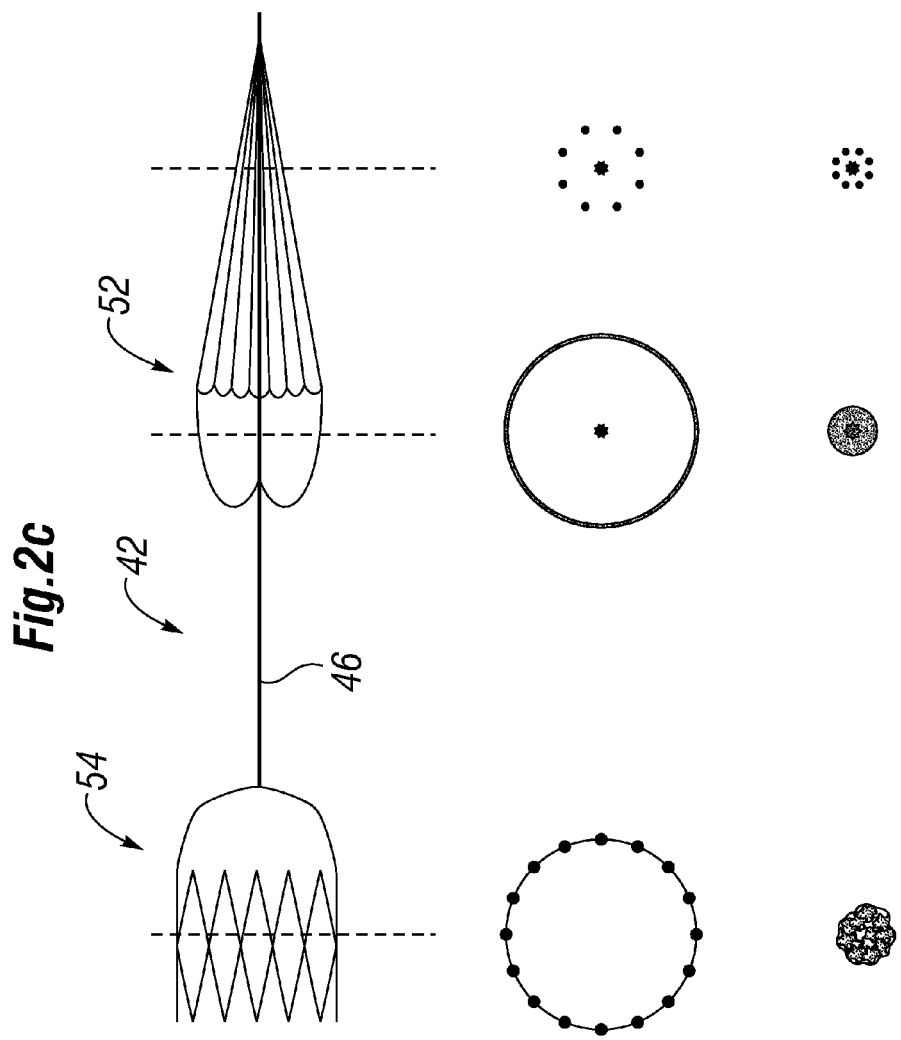

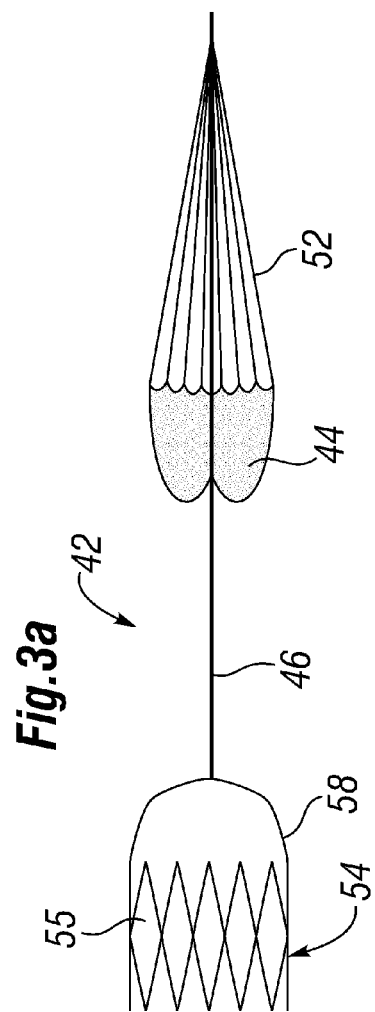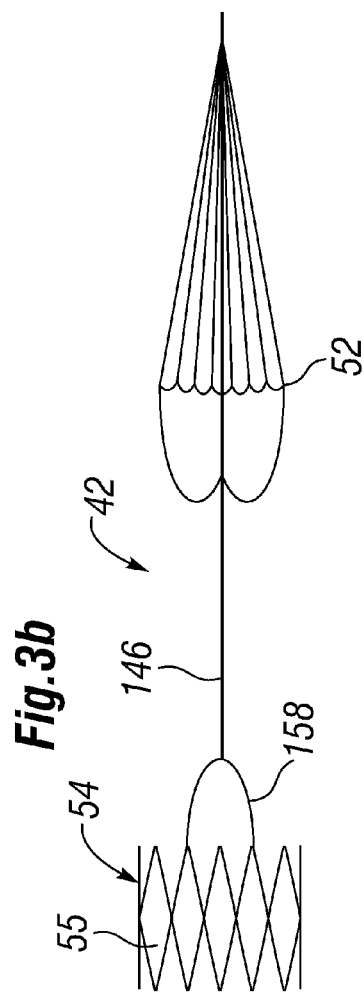

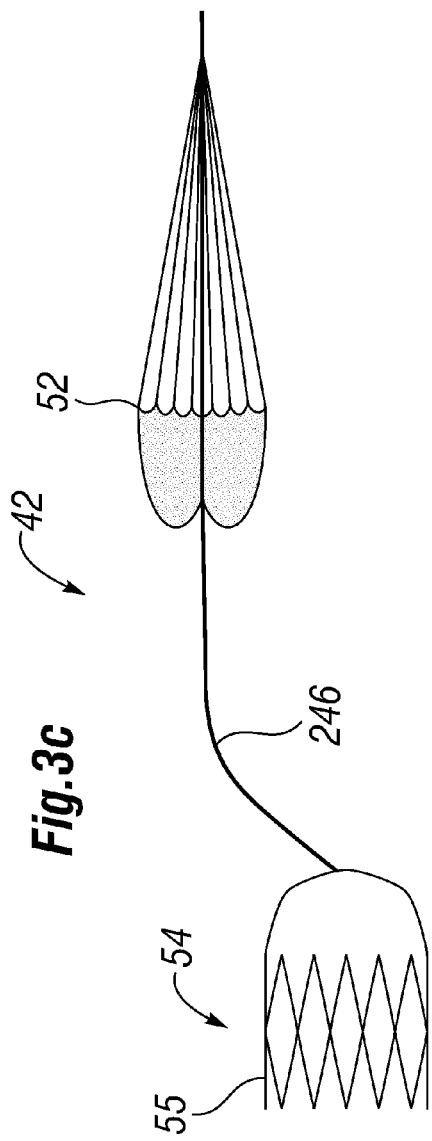
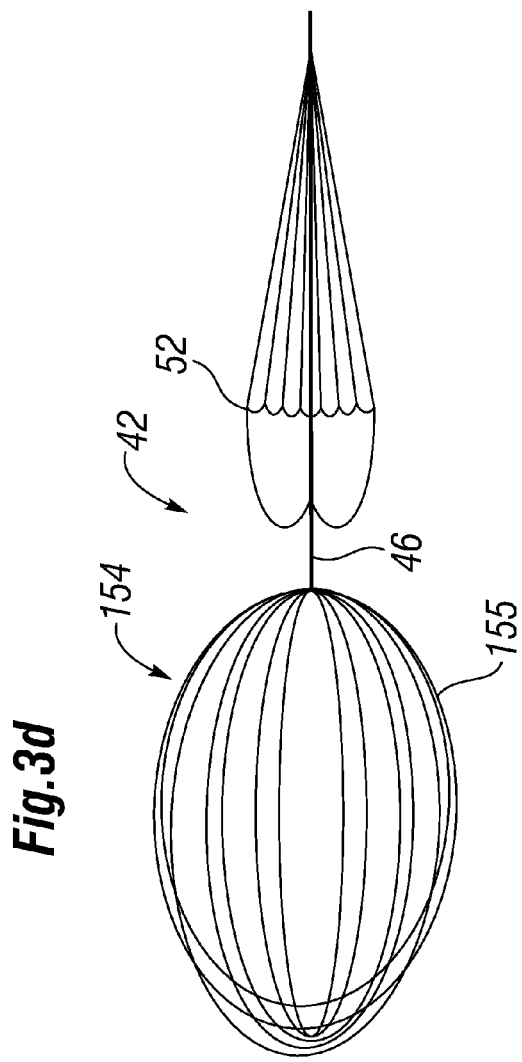

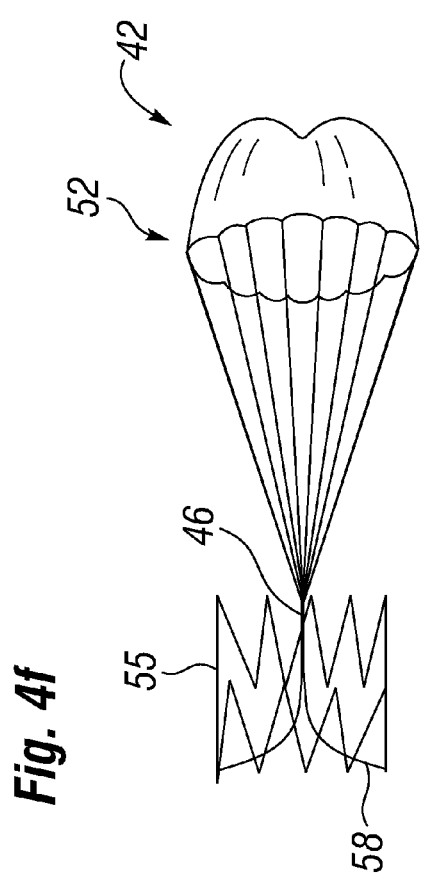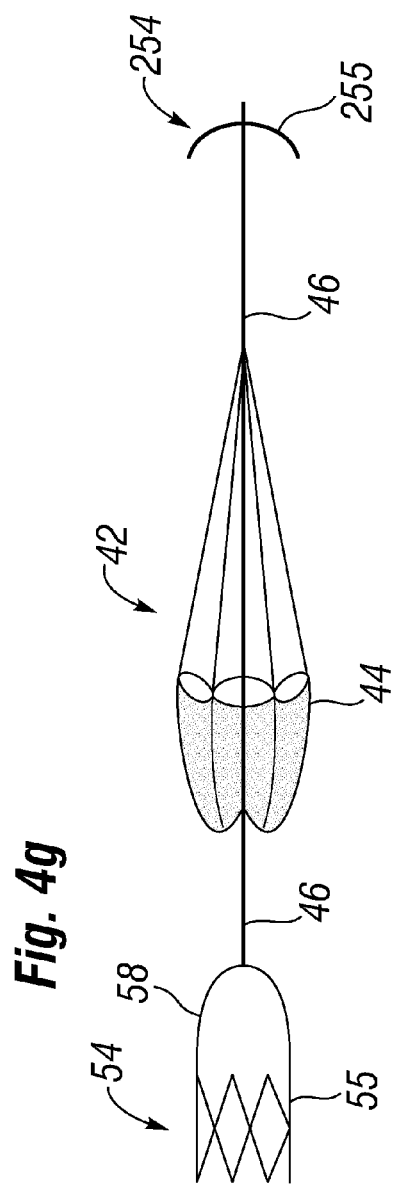

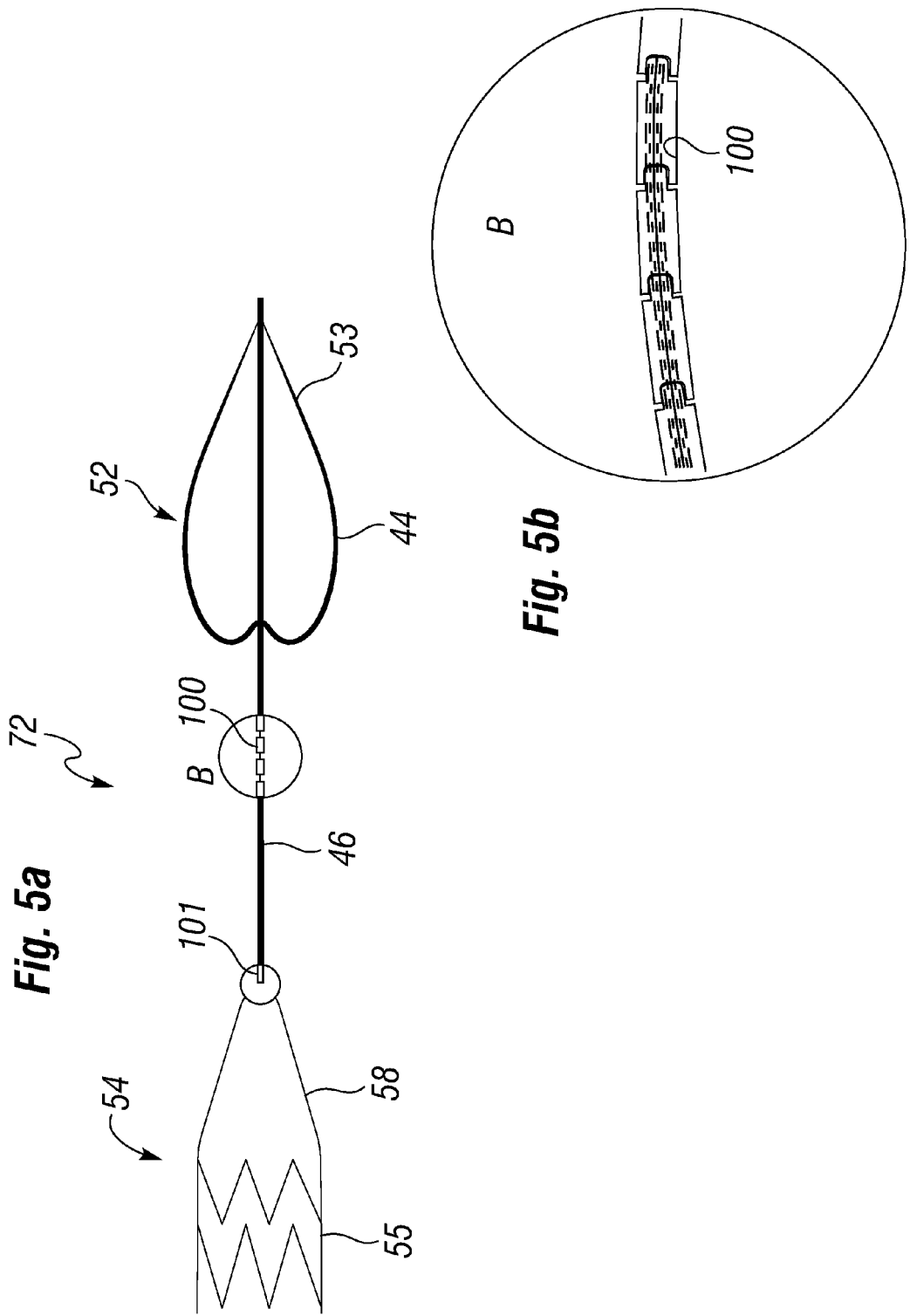

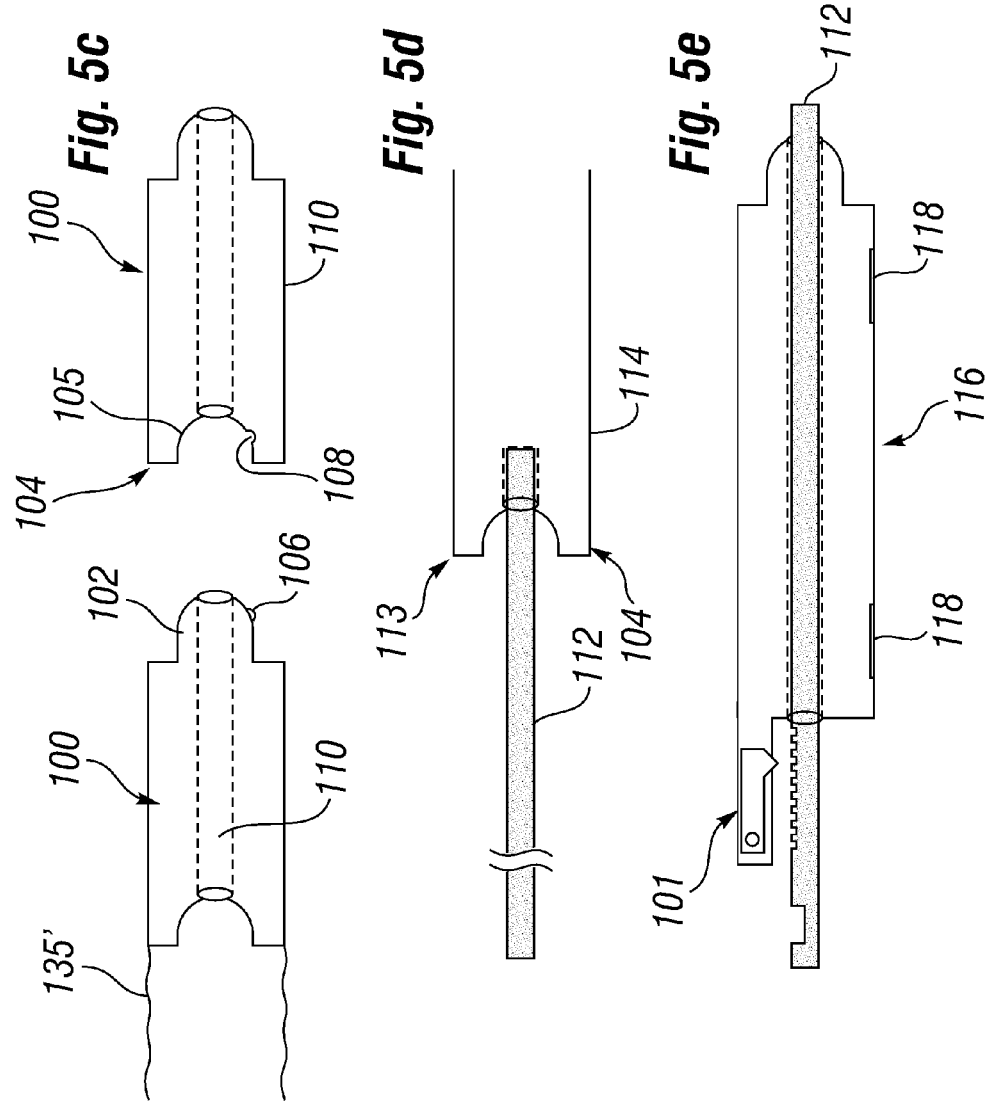

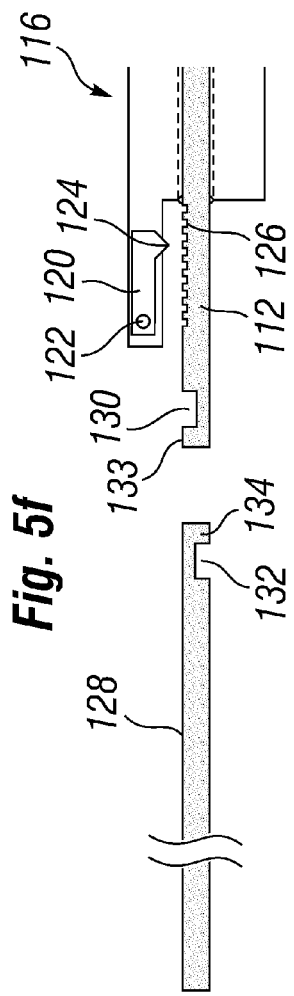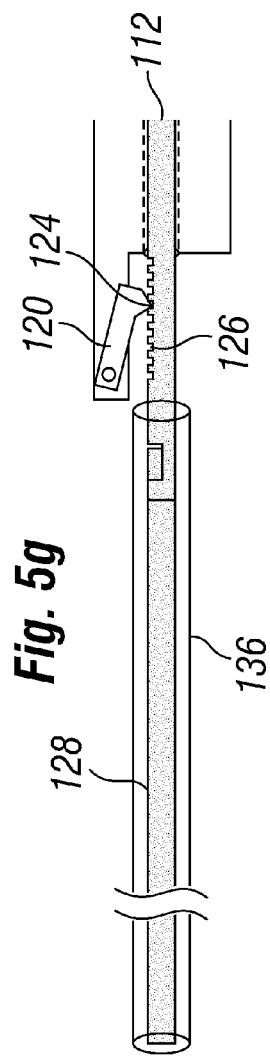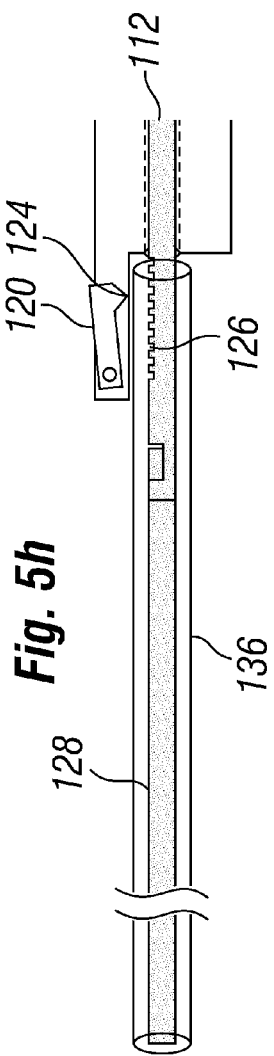

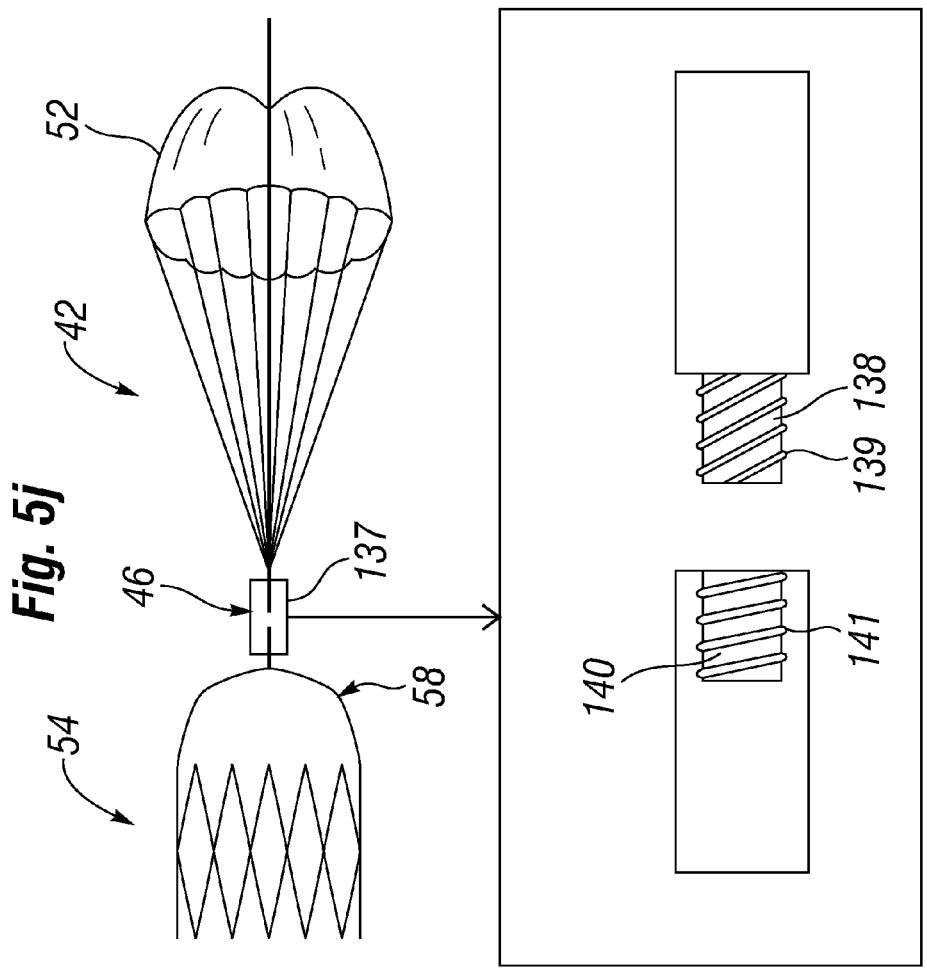

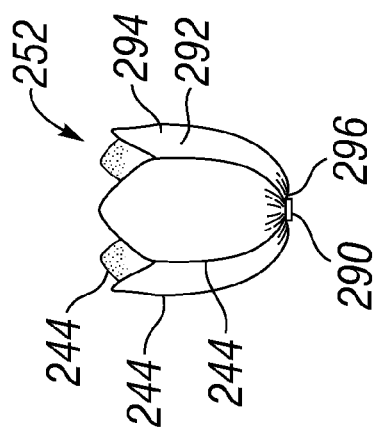
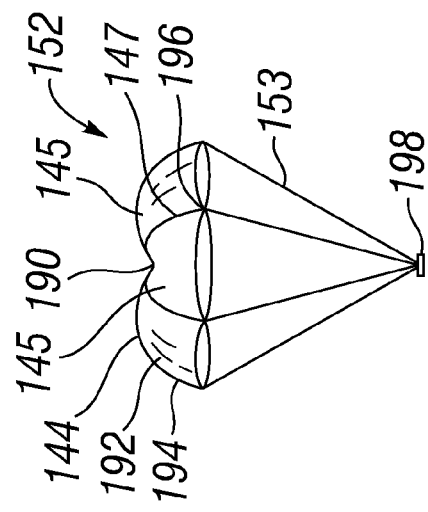
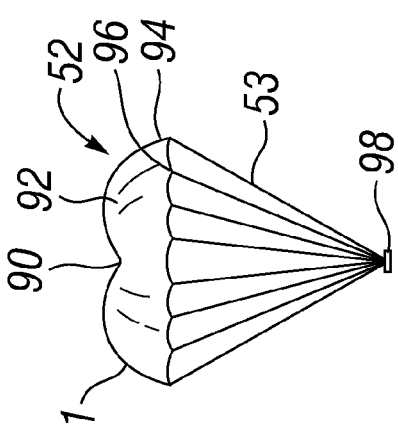

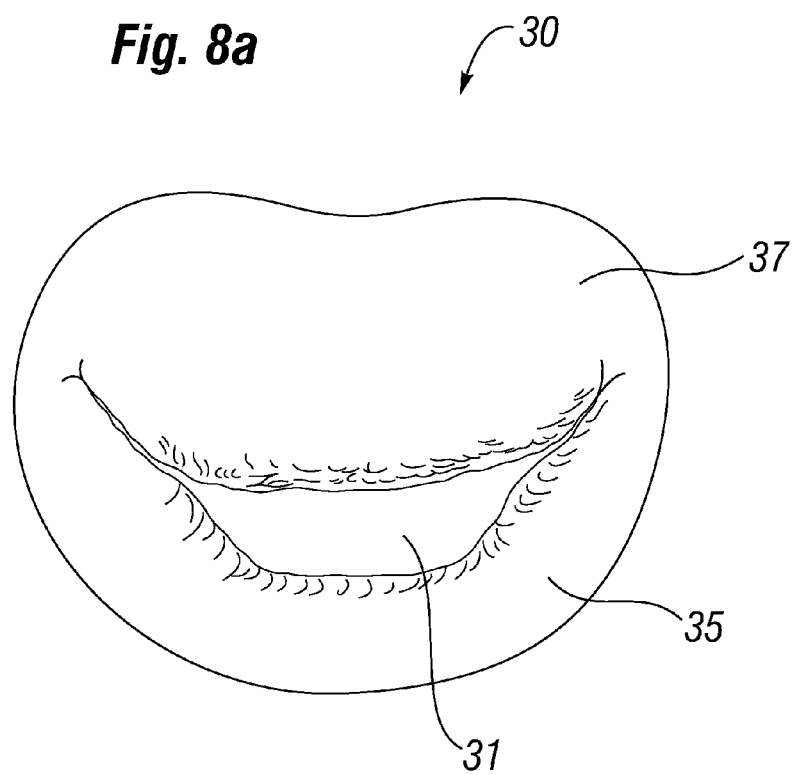

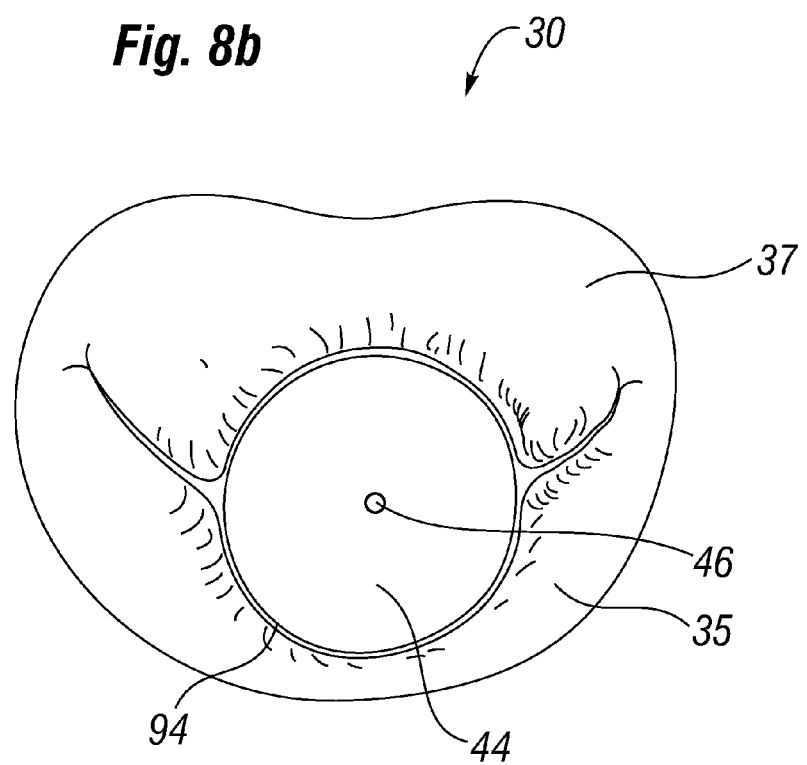

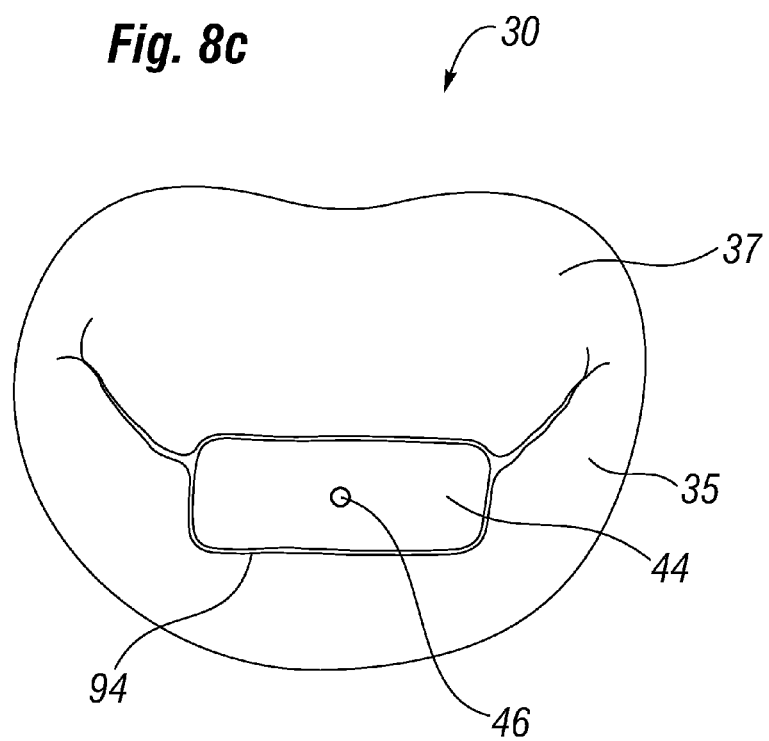

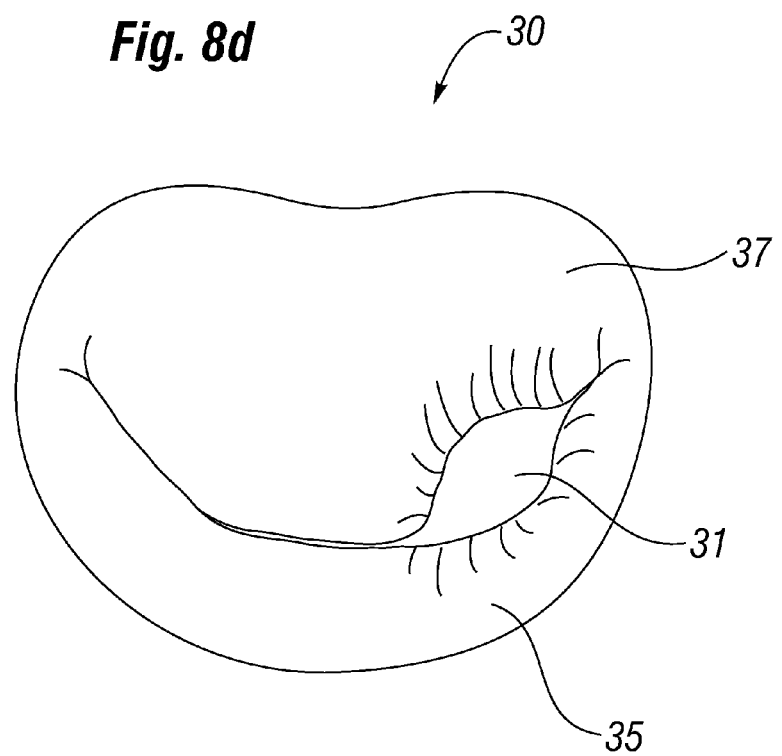

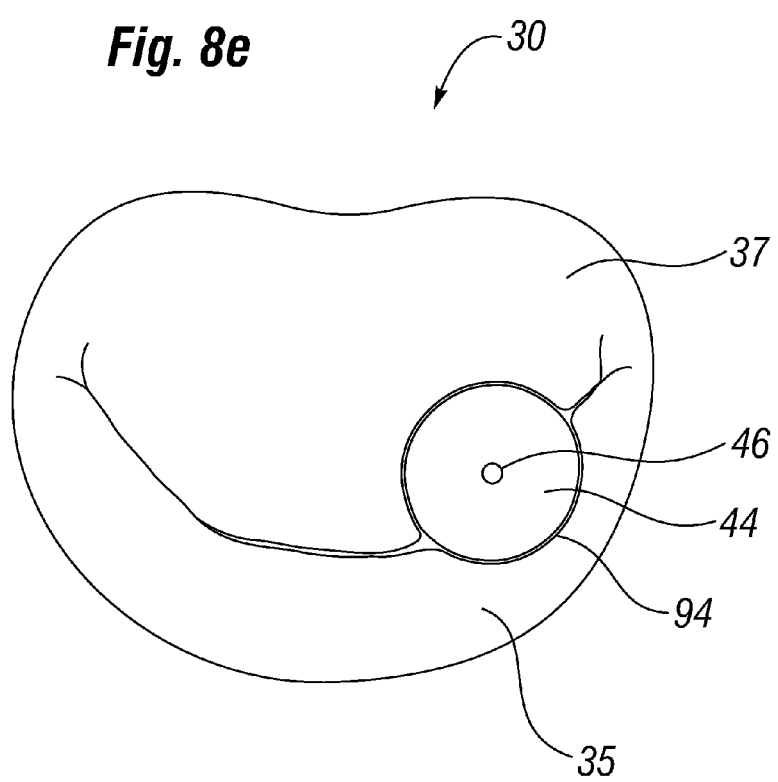

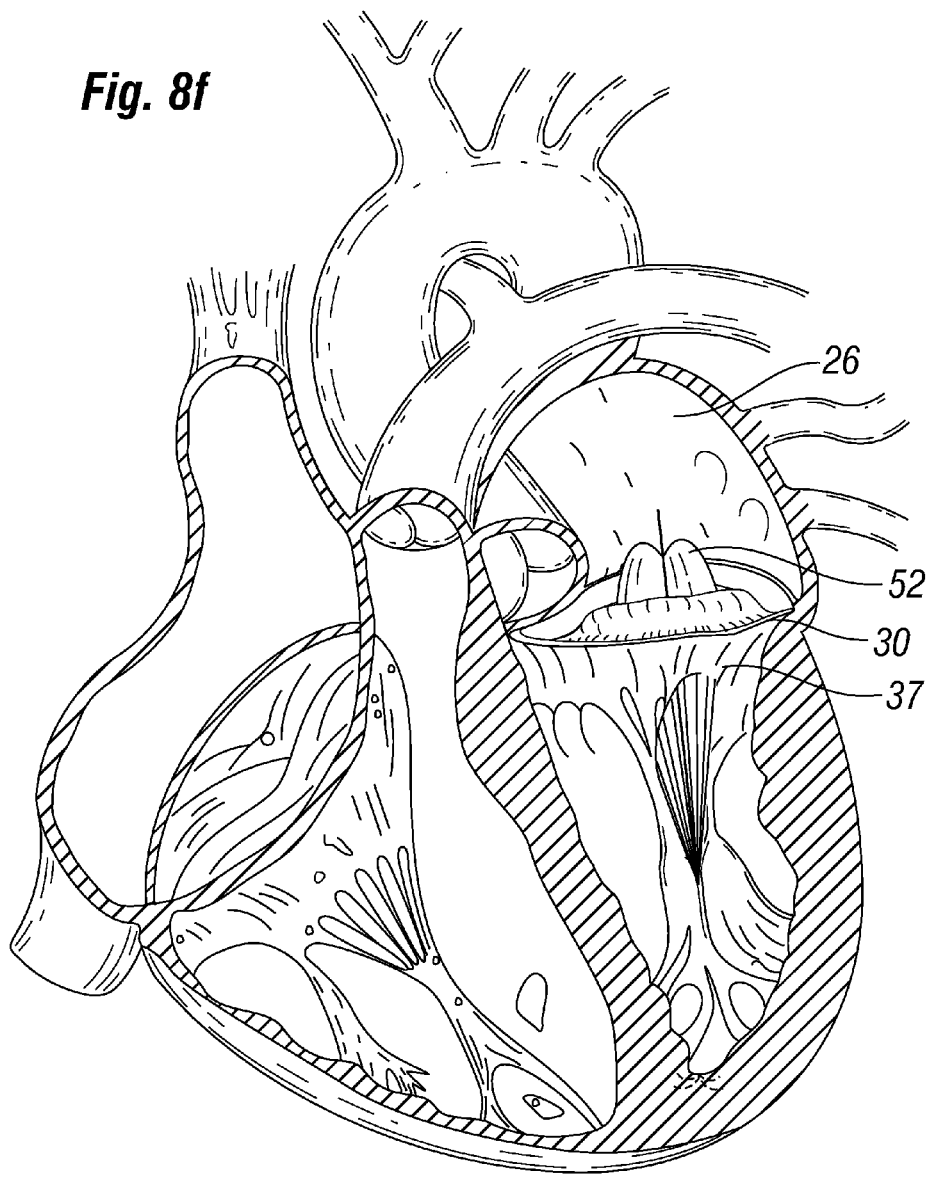

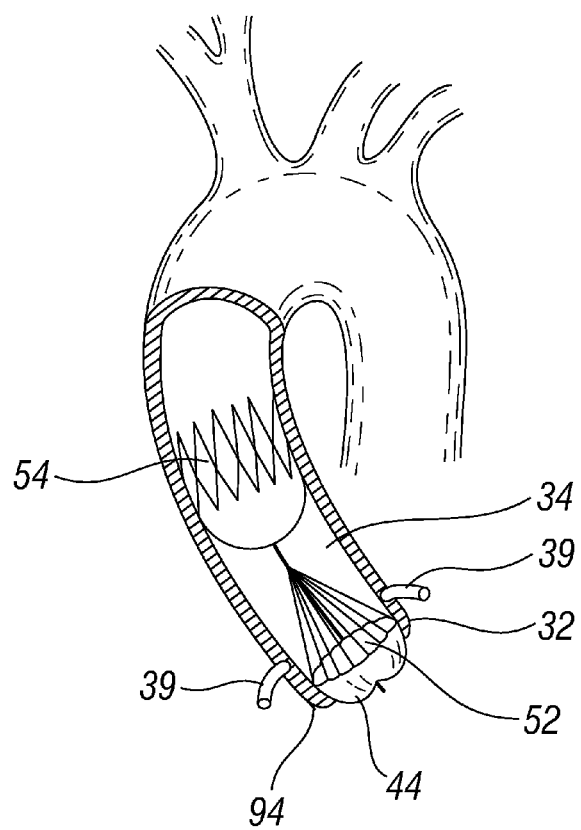

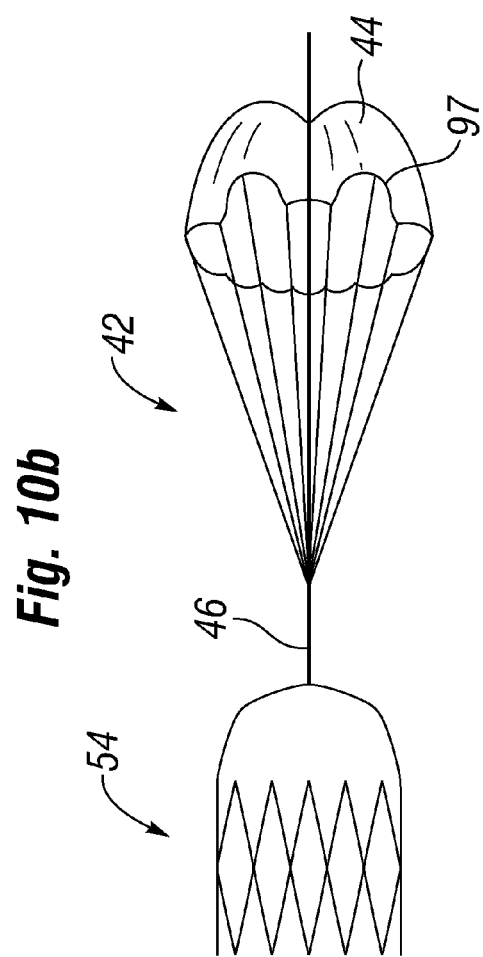

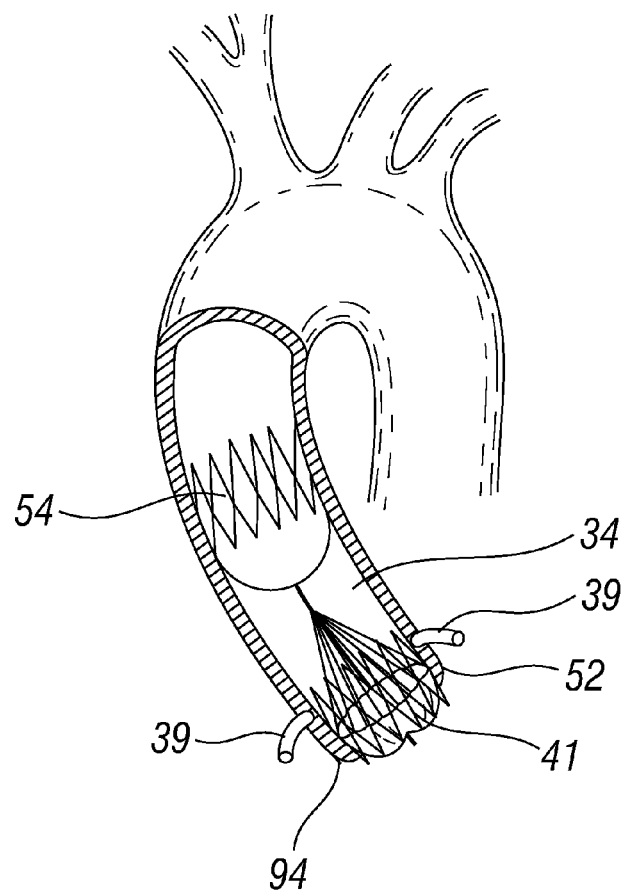

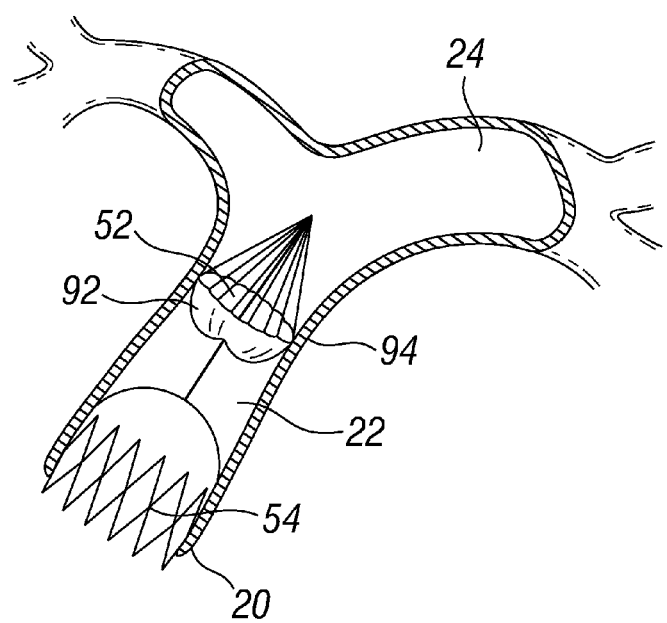

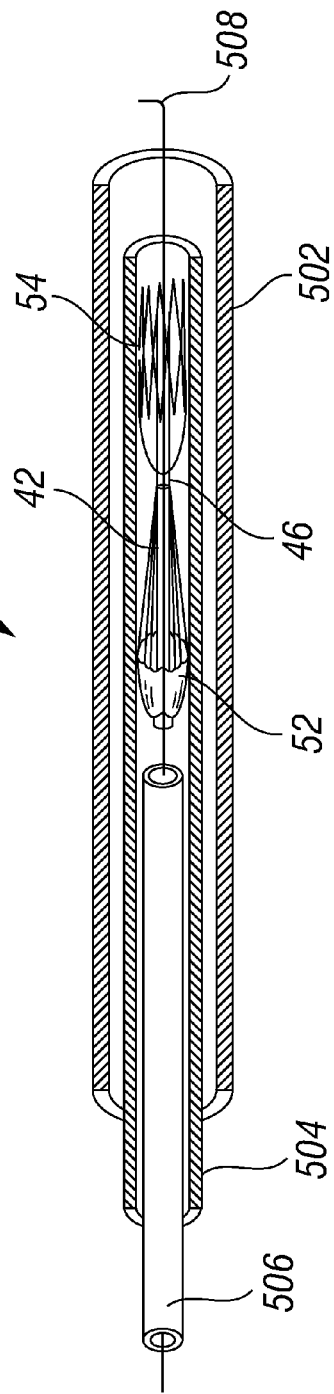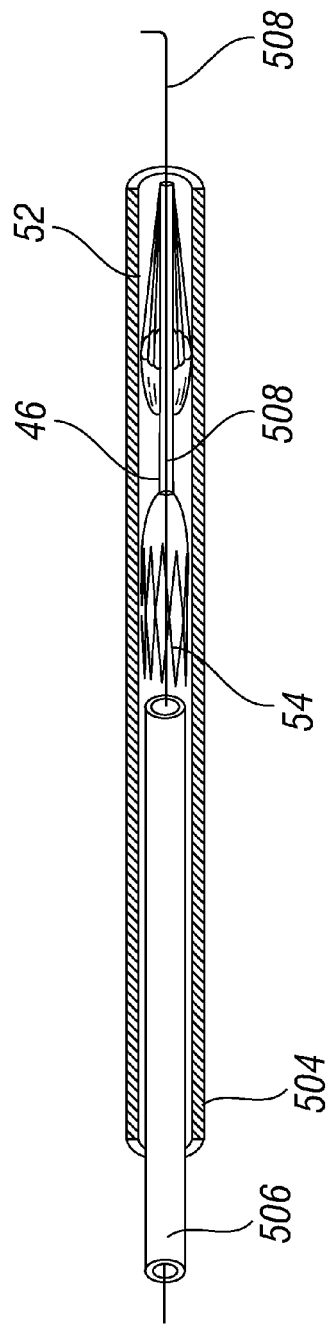

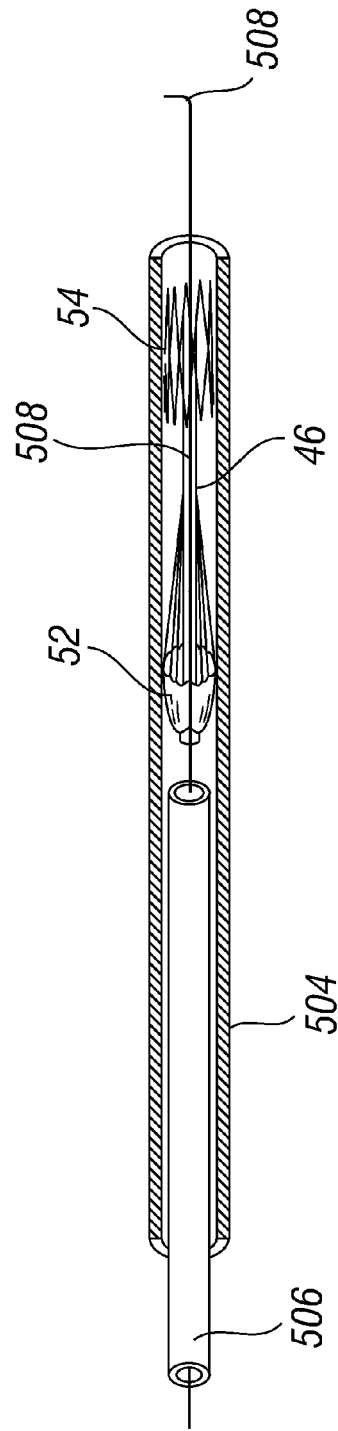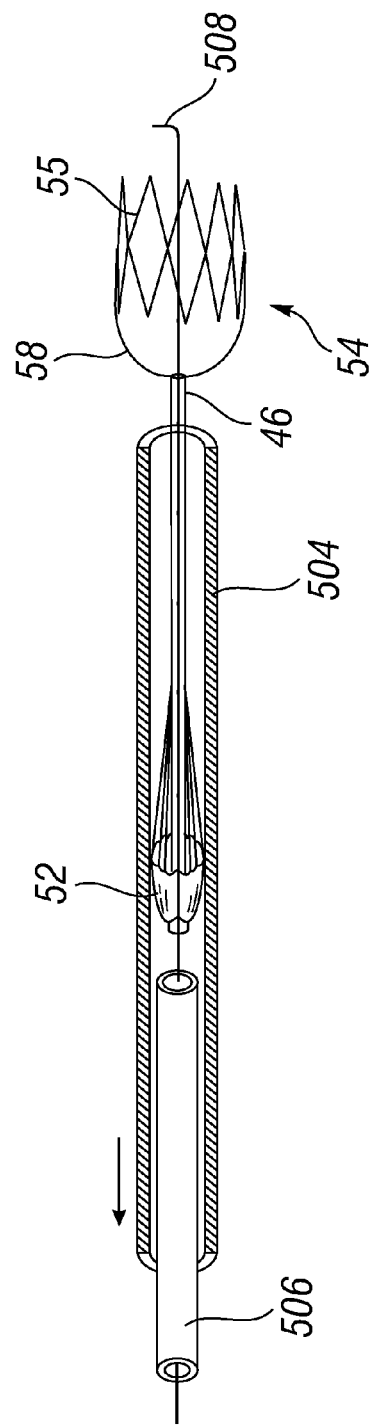

BLOOD FLOW CONTROLLING APPARATUS

CROSS REFERENCE TO A RELATED PATENT APPLICATION

This application is a continuation of U.S. application Ser. No. 11/407,582, filed Apr. 19, 2006, which claims priority to Swedish Patent Application No. 0500891-7, filed on Apr. 21, 2005, the disclosures all of which are incorporated by reference herein in their entireties.

TECHNICAL FIELD

The present invention relates to a blood flow controlling apparatus, which is configured to be implanted into a blood circulatory system of a patient, and to a method for treatment of leaking heart valves.

BACKGROUND OF THE INVENTION

Heart valve disease is a very common problem. Each year, half a million people in the world develop heart valve disease. 200,000 are too sick to be treated, but the rest are treated. At present, the treatment of heart valve disease consists of either heart valve repair or valve replacements. Both methods require open-heart surgery, by the use of total cardiopulmonary by-pass, aortic cross-clamping and arrest of the heart. To certain groups of patients, open-heart surgery is particularly hazardous. However, a less invasive method for repair of heart valves is considered generally advantageous.

Heart valve insufficiency may arise from a dilation of the valve annulus, whereby the leaflets of the heart valve are moved away from each other such that the area of coaptation is minimized or vanished. The area of coaptation is the area where the leaflets of heart valves lean against each other, thereby closing the valve opening sufficiently. Thus, an existing gap or incomplete area of coaptation between the leaflets creates a leak in the valve.

In U.S. Pat. No. 6,210,432, a less invasive method is proposed for treating heart valve insufficiency. Here, a method is described for treatment of mitral insufficiency without the need for cardiopulmonary by-pass and opening of the chest and heart. The method uses a device comprising an elongate body having such dimensions as to be insertable into the coronary sinus, which is a vein that substantially encircles the mitral orifice and annulus and drains blood from the myocardium to the right atrium. The elongate body has two states, in a first of which the elongate body has a shape that is adaptable to the shape of the coronary sinus, and to the second of which the elongate body is transferable from said first state assuming a reduced radius of curvature. Consequently, the radius of curvature of the coronary sinus is reduced. Due to the coronary sinus encircling the mitral annulus, the radius of the coronary sinus curvature as well as the circumference of the mitral annulus are reduced by the reduction of the radius of the coronary sinus. Thus, the described method takes advantage of the position of the coronary sinus being close to the mitral annulus, which makes repair possible by the use of current catheter-guided techniques. However, the described method is only useful in diseased valves where the reason for a valvular leak is caused by a dilation of the valve annulus.

For prolapsing leaflets, catheter-based methods have been presented where the two leaflets of the mitral valve are attached to each other by means of a thread (Percutaneous Edge-to-Edge provided by Edwards Lifesciences Corporation of Irvine, USA) or a clip (Evalve System provided by Evalve, Inc. of USA) creating a double opening with a shape like a bow-tie in the valve.

In cases where these methods are not useful, the valve may need to be replaced. Percutaneous replacement of heart valves are being developed for the aortic and pulmonary valves by Percutaneous Valve Technologies, Inc., now owned by Edwards Lifesciences Corporation and by CoreValve S.A. of Paris, France. NuMED, Inc. of New York, USA deliver a valve designed by Dr. Bonhoeffer for sole use in the pulmonary valve position. In all these devices, copies of normal human valves with three cusps are sewn from Glutaraldehyde-treated calf or horse pericardium tissue or bovine jugular vein tissue and mounted inside a stent. The stents from Edwards Lifesciences and NuMED are made of stainless steel and need to be dilated by a balloon, whereas the valve from CoreValve is mounted inside a self expanding stent of Nitinol. These devices from Edwards Lifesciences, NuMED and CoreValve will hereinafter be denoted stented valves. The stented valve is placed in the position of the valve it is supposed to replace and dilated, thereby pushing the leaflets and any calcified tissue away and thereby completely eliminating the remaining function of the valve leaflets. However, the stented valves are only useful in circular orifices such as the pulmonary and the aortic valves.

For the mitral valve and the tricuspid valve, no artificial valve has so far been presented for percutaneous placement. The main reason for not having access to percutaneously implantable valves in the tricuspid and in the mitral valve position is that the valve annulus is oval and the valve opening has a slit-like shape in case of a diseased mitral valve and triangular shape in case of a diseased tricuspid valve. The known stented valves are fixed to the valve annulus by means of friction caused by pressure from the stents towards the surrounding tissue in the valve opening. If the known stented valves with round circumference are introduced into the oval mitral annulus with a leaking area of slit-like shape, there will be wide open areas causing a severe leak, so called paravalvular leak, between the implanted device and the annulus. In addition, the tissue is too weak to allow a good fixation in the tricuspid and mitral orifices. Further, if a known stented valve is introduced in the mitral valve orifice, it would also create a block in the outflow of the aortic valve.

The known stented valves also have limitations in use for the pulmonary valve. The known stented valves are not suited to be implanted in children or growing juveniles, since they do not permit growths of the valve annulus. However, the most severe drawback with the known stented valves is the size of the device when mounted in delivery systems before implant. Mounting the valve inside a stent creates a huge diameter of the device catheter. The present devices are 7 to 9 mm in diameter, which is a huge diameter considering that the catheter is to be introduced through puncture holes in vessels through the skin and guided through sometimes severely calcified vessels, most of them having the same size as the device, to the target area. The diameter of such devices is half and half caused by the stent and the valve, which each is 3-4 mm thick.

SUMMARY OF THE INVENTION

It is an object of the invention to provide a device and method for treatment of leaking heart valves, wherein the treatment may be performed on any heart valve. It is a further object of the invention to provide a device and method that may be used without the need for open heart surgery or stopping the heart.

These and other objects of the invention are accomplished by a blood flow controlling apparatus and a method according to the independent claims.

Thus, the invention provides a blood flow controlling apparatus, which is configured to be implanted into a blood circulatory system of a patient. The apparatus comprises an anchoring means, which is arranged to fix the position of the apparatus in the blood circulatory system, and a valve means being connected to the anchoring means. The valve means is configured to be arranged within the blood circulatory system and is configured to be extendable in a direction transverse to blood flow in order to make contact with native tissue when inserted in the blood circulatory system. The valve means is further configured to release said contact as a result of being exposed to blood flow in a permitted direction.

The blood flow controlling apparatus according to the invention may advantageously be used for treating a leaking heart valve. The valve means of the apparatus is arranged to make contact with surrounding tissue for closing the valve and to release the contact for opening of the valve. The valve means may be arranged for making contact with heart valve tissue, such as leaflet tissue. While having contact with the leaflet, an area of coaptation between the valve means and the native leaflet is established. In the area of coaptation, backflow through the valve may be prohibited. The introduction of the valve means in an orifice of a heart valve therefore introduces a further leaflet which cooperates with the native valve leaflets. Thereby, the apparatus is arranged according to an entirely new concept conserving and utilizing the remaining function of the leaflets of the diseased native valve.

The valve means may be configured to contact tissue in the area of coaptation such that the valve means seals against native tissue to prevent blood flow past the valve means when the valve means extends in the direction transverse to blood flow.

The feature that the valve means is configured to be extendable in a direction transverse to blood flow should be construed as the valve means being movable to increase its extension in the direction transverse to blood flow and not necessarily that the valve means will extend entirely in this direction. Thus, the valve means is able to move between a closed state, wherein it extends sufficiently in the direction transverse to blood flow for preventing blood flow past the valve means, and an open state, wherein it extends primarily in a direction along the blood flow.

Further, the valve means may be oversized such that the valve means is arranged to overlap with native tissue when extending in the direction transverse to blood flow. This strengthens the seal between the valve means and the tissue.

Since the valve means is arranged to close the leak in a regurgitating heart valve by contacting and overlapping native valve tissue, the apparatus may be applied to a valve of any size and shape. As a matter of fact, the valve means of the apparatus can be oversized to such a degree that it will compensate for continuous deteriorations and shrinking of the native leaflets that is probable to occur especially in rheumatic heart disease. In the same way, an oversized valve means will allow growth of the native vessel or valve when implanted in children or still growing juveniles.

Although the apparatus has been described above as cooperating with valve tissue, it is contemplated that the apparatus may alternatively be arranged such that the valve means makes contact with an inner wall of a vessel in which it is inserted, such as to introduce a valve function within a vessel.

The apparatus may appropriately be inserted through the vascular system into a body and advanced to the heart or the great vessels close to the heart and to be subsequently deployed in or adjacent to the native heart valve in order to treat any leak in a heart valve. Thus, there is no need for opening the chest, stopping the heart or cutting or treating of the native valve tissue with advanced or demanding methods.

The valve means may present a contact surface comprising a contact area to make contact with native tissue, wherein the contact surface is arranged to extend such as to face blood flow from the permitted direction. Thus, blood flow from the permitted direction will hit the contact surface, providing a force on the valve means. This will press the valve means to release contact with tissue and allow blood flow past it.

The apparatus may further comprise a spacer for providing a distance between the anchoring means and the valve means. The spacer may be arranged in the form of an elongate connecting means which connects the anchoring means to the valve means and provides an axial spacing between the anchoring means and the valve means. Consequently, the apparatus separates the valve means from the anchoring means, providing a small diameter of the apparatus, since the diameter of the anchoring means is not superposed on the diameter of the valve means. The diameter of the apparatus may typically be 3-4 millimeters. This is very useful for introduction of the apparatus, since it may be introduced through a small puncture hole into the body. This makes the surgical procedure less invasive. Further, the anchoring means will not be arranged in the orifice of the native valve, whereby a much larger valve opening is permitted and blood flow is facilitated through the valve.

The valve means may be attached to the connecting means as to strive towards extending in the transverse direction to the connecting means. This implies that the valve means has an inherent strive towards making contact with a valve leaflet or a vessel wall when implanted in the patient. The valve means will then need to be exposed to a force to prevent extending in the transverse direction. Such force may be provided by blood flow in the allowed direction. As a result, the function of the valve means to allow blood flow in a forward direction and prevent blood flow in a backwards direction may be accomplished by the inherent strive. Thus, no outside control of the valve means will be needed to achieve this function. In fact, the valve means may be arranged such that blood flow in the backwards direction pushes the valve means towards the native heart valve leaflets or a vessel wall to make contact with the valve leaflets or vessel wall. Thus, backflow may initially aid in extending the valve means in the transverse direction.

The valve means may be arranged on the connecting means. According to one embodiment, the valve means is arranged symmetrically around the connecting means. This implies that the valve means will act identically around the circumference of the connecting means in order to close against the native valve leaflet or the vessel wall. As a result, the placement of the connecting means and the anchoring means is not very critical for ensuring that the valve means will completely seal blood flow through the valve or the vessel by making contact with the native valve leaflet or the vessel wall over its entire circumference. Further, as mentioned above, the valve means may be over-sized such that the diameter of the valve means, when extending transversely to the connecting means, is larger than the jet of leaking blood or larger than the diameter of the vessel in which it is placed. This ensures that the valve means will seal the vessel properly when making contact with the vessel wall, even when the connecting means is not exactly centrally positioned in the valve or the vessel. However, the apparatus may be designed such that at least part of the connecting means is flexible allowing the valve means to center itself to the center of the blood flow.

The valve means may in its open state be configured to have a larger extension along the direction of blood flow than a native valve in its open state. This implies that the valve means may be arranged to reach and make contact with native valve leaflets that are extending to abnormal positions. This ensures that a coaptation will be achieved also to areas of the native valve that are prolapsing towards the atria, a situation that often occurs in diseases with redundant native valve material. Also, coaptation will be achieved with leaflets restrained by shortened chordae tendinae.

The valve means may comprise a flap, which is movable between an open position where it extends along the connecting means and a closed position where it extends in a transverse direction to the connecting means.

The flap may comprise an attachment end, which forms an attachment of the flap to the connecting means in a longitudinal position of the connecting means. The flap may further comprise a contact end, which is arranged to make contact with native tissue. The flap may be hingedly movable around the attachment position between its open position and closed position, where the contact end makes contact with tissue.

The contact end may be connected to the connecting means by means of control strings. The control strings may prevent the flap from turning over to extend along the connecting means in the opposite longitudinal direction. If the flap would turn over, no contact with the native valve or the vessel wall would occur, and consequently blood may regurgitate through the valve means.

The flap may form an attachment to the connecting means extending along a longitudinal direction of the connecting means. The flap will then have a secure attachment to the connecting means to avoid the need of control strings for preventing the flap to be turned over.

The sealing of the valve means to the native valve leaflet or the vessel wall may be accomplished by various embodiments. In one embodiment, the flap extends around the entire circumference of the connecting means. The flap may be homogenous or comprise several subsections, which may form an umbrella- or parachute-like shape.

In another embodiment, the valve means comprises several flaps. The flaps may overlap each other to properly seal the valve or vessel when extending to make contact with the native valve leaflet or the vessel wall. Thus, no backflow is allowed between the flaps. As an alternative, adjacent flaps may tightly contact each other to prevent leakage between the flaps.

The flaps may be strengthened at an end which is attached to the connecting means. The strengthened base may act to prevent the flaps from turning over.

The flap or flaps may preferably be made of biological tissue, such as animal tissue treated with Glutaraldehyde or similar solutions. The animal tissue may originate from heart valve, blood vessels or pericardial tissue, which is normally used for producing artificial biological heart valves. However, the flaps may also or alternatively be made of a synthetic material, such as polyurethane, polyvinyl or polytetrafluoroethylene (PTFE), or a shape memory material, such as Nitinol or shape memory polymers.

One advantageous feature of the blood flow controlling apparatus is the anchoring means for fixing the position of the apparatus in the blood circulatory system. The anchoring means prevents migration of the valve means away from a correct position inside a heart valve or a vessel. During systole of the heart rhythm, there is a high pressure gradient between ventricle and atrium and, during diastole of the heart rhythm, there is a high pressure gradient between the aorta and left ventricle and between the pulmonary artery and the right ventricle. Therefore, a strong fixation of the apparatus is needed to avoid migration of the valve means.

Depending on the fixation site for the anchoring means, the valve means may be arranged on either side of the anchoring means such that the allowed blood flow may be directed from the anchoring means to the valve means or vice versa.

Further, depending on the fixation site in the blood circulation system of the patient, there are a number of embodiments for the anchoring means. The valve means may be arranged to be placed at a mitral valve, a tricuspid valve, a pulmonary valve or an aortic valve. The apparatus may therefore be used to treat a leak in any of these valves. Alternatively, the valve means may be arranged in an arterial vessel or a venous vessel for introducing a valve function in the artery or the vein, which may replace the function of a diseased heart valve. The anchoring means may be arranged to engage an arterial vessel wall, a venous vessel wall, the atrial septum, the interventricular muscular septum, a muscular ventricular wall, or an atrial wall. The anchoring means is fixed in a position that is suitable for the placement of the valve means.

The anchoring means may comprise an expandable element for engaging wall tissue. This implies that the anchoring means fixes the position of the apparatus by securing the apparatus to wall tissue. The expandable element may be tube-shaped. The anchoring means may then be used to fix the position of the apparatus to a wall of a vessel by engaging the vessel wall along the entire circumference of the tube-shaped element. The anchoring means may be arranged to fix the position of the apparatus to a vessel in or adjacent to the heart where the valve means is to be arranged in a regurgitating heart valve. The expandable element may be a stent forming a tube from a mesh of struts. The expandable element may be a conventional vascular stent, which is normally used for supporting vessel walls during dilation treatment of vascular disease.

The connecting means is attached to the anchoring means for connecting the valve means to the anchoring means. The connecting means may e.g. be connected to either end of the anchoring means, such as to extend through the anchoring means towards the valve means or as an extension from the anchoring means towards the valve means. The connecting means may be attached to one or more, preferably two, stent struts. Preferably, the attachment is a seamless continuation of the strut material into the connecting means. Such attachment could be achieved if the anchoring means and the connecting means are constructed out of the same piece of material, for instance by laser cutting. Otherwise, the attachment could be made by means of welding.

The expandable element may alternatively comprise a plurality of springs arranged to engage with opposite sides of a wall of a heart atrium. The anchoring means may thus fix a position inside a heart atrium by engaging opposite walls of the heart atrium.

In an alternative embodiment, the anchoring means comprises a disk-shaped element, which is arranged for engaging a tissue wall. In this embodiment, the valve means and the disk-shaped element of the anchoring means are arranged on opposite sides of the tissue wall and the connecting means extends through the tissue wall. The position is fixed by the disk-shaped element abutting and engaging the tissue wall.

The anchoring means may comprise another disk-shaped element and wherein the disk-shaped elements are connected by a penetration part for engaging opposite sides of a tissue wall. In this embodiment, the disk-shaped elements fix the position of the apparatus by abutting and engaging opposite sides of the tissue wall.

The anchoring means comprising one or more disk-shaped elements may be used for fixation to e.g. the interatrial septum or another heart wall, where the valve means is to be arranged in the mitral or tricuspid valve.

According to a further alternative embodiment, the anchoring means comprises hooks arranged for penetrating wall tissue. Such an anchoring means may also be used for fixation to e.g. the interatrial septum or another heart wall, where the valve means is to be arranged in the mitral or tricuspid valve.

According to another alternative embodiment, the anchoring means comprises a plurality of arms arranged for engaging chordae tendinae. According to yet another alternative embodiment, the anchoring means comprises clips arranged for engaging papillary muscles. These embodiments of the anchoring means may also be used for fixation to e.g. the interatrial septum or another heart wall, where the valve means is to be arranged in the mitral or tricuspid valve.

The anchoring means may be made of a shape memory material, such as Nitinol or a shape memory polymer. This implies that the anchoring means may be self-expandable to assume its pre-programmed shape. However, ordinary stainless steel, stainless spring steel or any other metal might be used. The connecting means would preferably be made of similar material as the anchoring means.

The apparatus may comprise two connecting means extending from the anchoring means in different directions, wherein valve means are attached on each connecting means. The apparatus may then be used for treating two malfunctions in the body simultaneously. For example, the apparatus may be arranged such that one valve means is placed in the mitral valve and one valve means is placed in the tricuspid valve for simultaneous treatment of these valves. The anchoring means may comprise two disk-shaped elements arranged to engage opposite sides of the interatrial septum or the interventricular septum and connecting means may extend in opposite directions from the anchoring means towards the mitral and tricuspid valves, respectively.

The connecting means may be arranged to assume a programmed shape within the blood circulatory system. In this case, the connecting means may be made of a shape memory material, e.g. Nitinol, allowing the connecting means to be straight during insertion and to resume a pre-programmed, curved shape exactly fitting the calculated track from the fixation point to the correct position of the valve means. This facilitates insertion and placing of the apparatus in the blood circulatory system.

In an alternative embodiment, the connecting means comprises a plurality of segments arranged in sequence, wherein the interrelationship between adjacent segments is controllable. This implies that the connecting means may be designed in a very flexible manner by the segments being able to flexibly move in relation to each other. The connecting means may thus e.g. allow an operator to manipulate it for centering the valve means in a stream of blood created by the leak in the native valve.

The connecting means may further comprise a locking mechanism for locking the position of adjacent segments to each other. Thus, when placed in an appropriate position, each segment may then be locked to each other for fixating the shape of the connecting means and thus the position of the valve means. The locking mechanism may comprise a tension wire arranged extending through the sequential segments. The wire may be locked under tension for fixating the shape of the connecting means. The locking mechanism may further comprise a tap for engaging the tension wire to lock the form of the tension wire through the sequential segments. Thus, the tap locks the wire under tension to fix the shape of the connecting means.

The connecting means may have a longitudinal groove or channel for receiving a guide wire. The connecting means may e.g. be tubular or U-shaped for allowing a guide wire to pass through the connecting means. This implies that the connecting means may be introduced into the patient by sliding over a guide wire.

The connecting means may further comprise a disengaging means for releasing the valve means from the anchoring means. This implies that a valve means, which may have lost its treating function over time, may be replaced without the need to replace the entire apparatus.

According to another aspect of the invention, there is provided a kit for controlling blood flow in a blood circulatory system of a patient. The kit comprises a blood flow controlling apparatus as described above and a delivery system for carrying the blood flow controlling apparatus to a desired position in the blood circulatory system.

The kit may provide a package to a surgeon who is about to introduce a blood flow controlling apparatus into a patient. Thus, the kit provides both an implant which may be used for treating the patient and a delivery system which may be used for inserting the implant.

The anchoring means of the blood flow controlling apparatus may be mounted in the delivery system during storage, whereas the valve means of the blood flow controlling apparatus may be mounted in a container with appropriate storage fluid. Where the valve means is made of biological material, it will need to be stored in a storage fluid in order not to be destroyed during storage. The valve means may be arranged such that the operator may pull the valve means inside the delivery system just prior to insertion into the patient.

The valve means may be disconnected from the anchoring means during storage. This implies that the valve means is stored in a separate container and may be attached to the rest of the blood flow controlling apparatus just prior to insertion into the patient.

The kit may further comprise a guide wire for guiding insertion of the delivery system to the desired position through the vascular system of the patient. The delivery system may also comprise a guiding catheter which is arranged to be pushed over the guide wire to the desired position. Thus, the blood flow controlling apparatus may be inserted to the desired position through the vascular system of the patient.

According to a further aspect of the invention, there is provided a method for controlling blood flow in a blood circulatory system of a patient. The method comprises inserting an artificial valve means to a desired position in the blood circulatory system; arranging the artificial valve means in the desired position such that the valve means extends in a direction transverse to blood flow for making contact with heart valve tissue or vessel wall tissue and the valve means releases said contact when being exposed to blood flow in a permitted direction; and fixing the position of the artificial valve means by attaching an anchoring means in the blood circulatory system, said anchoring means being connected to the artificial valve means at an axial distance therefrom. The implanted artificial valve means may thus block backflow in a leaking heart valve and allow only forward flow in the valve. The anchoring means may be arranged at an axial distance from the valve means provided by an elongate spacer. Consequently, the valve means is spaced from the anchoring means, enabling insertion into the blood circulatory system through a small diameter, since the diameter of the anchoring means is not superposed on the diameter of the valve means.

The inserting may be performed through the vascular system by means of a catheter. According to this method, the valve means may be inserted and fixated by means of an instrument being inserted through the vascular system of a patient providing a low-invasive treatment method that only requires a needle puncture of the skin, thereby getting access to the vascular system, without the need of any surgery or anaesthesia. The access to the vascular system may be achieved through the venous or arterial system of the patient.

As an alternative, the valve means may be inserted and fixated through a small surgical access from outside the chest, entering the pericardial space and inserting the apparatus through the ventricular or atrial wall by guidance of direct vision and/or x-ray and ultrasound imaging.

As another alternative, the valve means may be inserted and fixated thoracoscopically, by means of an endoscope or a surgical robot, using an access from outside the chest, entering the pericardial space and inserting the device through the ventricular or atrial wall by guidance of vision through the endoscope or the robot equipment.

BRIEF DESCRIPTION OF THE DRAWINGS

The invention will now be described in further detail by way of example under reference to the accompanying drawings.

FIG. 2a is a schematic view of a blood flow controlling apparatus according to a first embodiment of the invention with a valve means of the apparatus being in an open state allowing blood flow.

FIG. 2b is a schematic view of a blood flow controlling apparatus according to a first embodiment of the invention with a valve means of the apparatus being in a closed state preventing blood flow.

FIG. 2c shows different cross-sections of the blood flow controlling apparatus in expanded and compressed states.

FIGS. 3a-3d are schematic views of the blood flow controlling apparatus showing different embodiments of an expanding element for anchoring the apparatus.

FIGS. 4a-4f are schematic views of the blood flow controlling apparatus showing other embodiments of an anchoring means.

FIG. 4g is a schematic view of a blood flow controlling apparatus comprising two anchoring means.

FIGS. 5a-i are schematic views of a connecting means of the blood flow controlling apparatus.

FIG. 5j is a schematic view of a connecting means providing detachment of the valve means from the anchoring means.

FIGS. 6a-c are schematic views of different embodiments of a valve means of the blood flow controlling apparatus.

FIGS. 8a-f are schematic views of a mitral valve indicating a valve means of a blood flow controlling apparatus according to the invention being inserted for treating a leak in the mitral valve.

FIGS. 10a-c show a blood flow controlling apparatus being inserted in the aorta for treatment of a leaking aortic valve.

FIGS. 11a-d show different embodiments of a blood flow controlling apparatus being inserted in the pulmonary artery.

FIGS. 14a-h are schematic views showing a delivery system carrying and releasing the blood flow controlling apparatus.

DETAILED DESCRIPTION OF A PREFERRED EMBODIMENT

Figure 1:
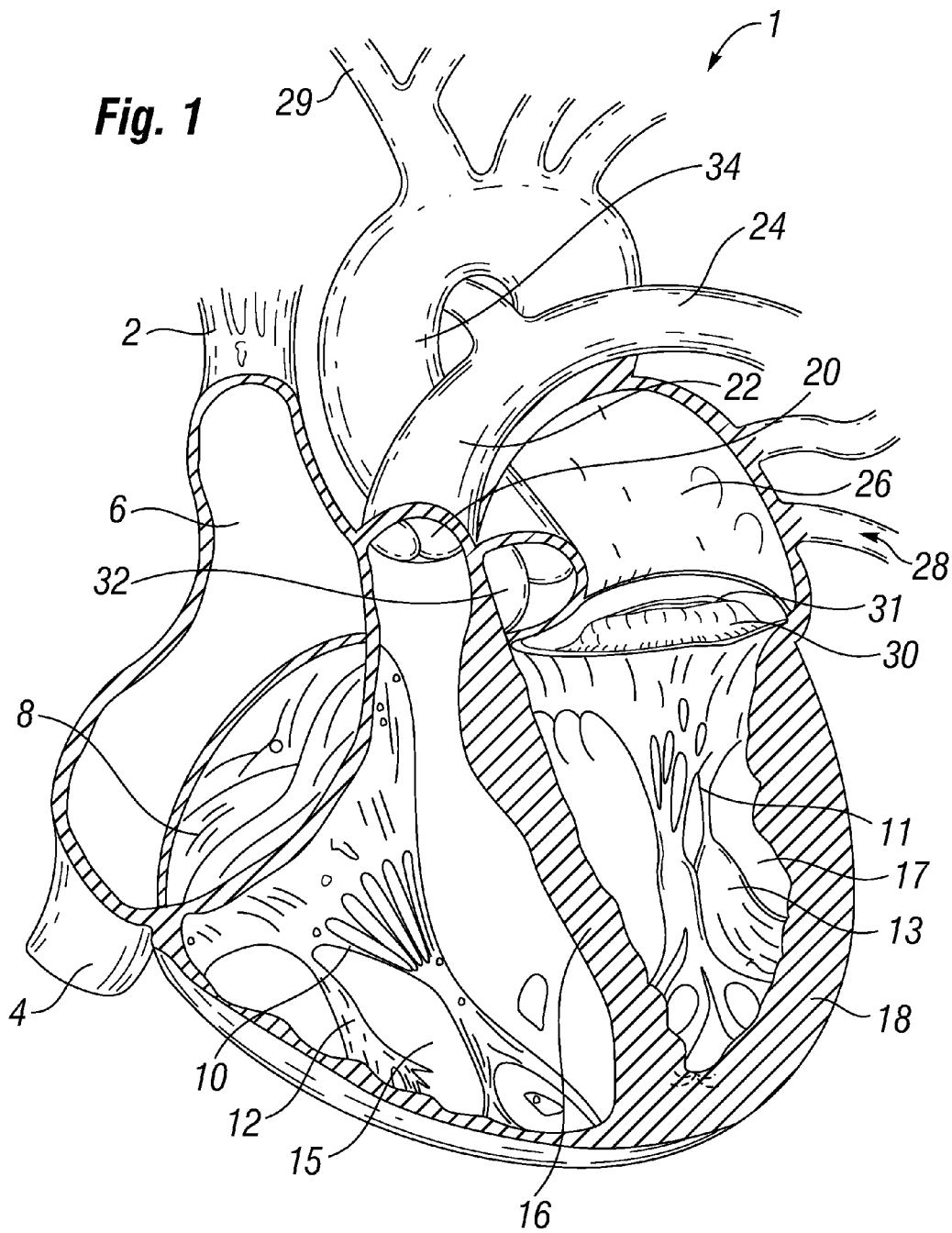
FIG. 1 is a schematic view of a partial cross-section of the heart indicating its general anatomy.

Referring to FIG. 1, the general anatomy of a heart 1 will be described. Blood is lead through the superior vena cava 2 and the inferior vena cava 4 into the right atrium 6 of the heart 1. The tricuspid valve 8 controls blood flow between the right atrium 6 and the right ventricle 15. The tricuspid valve 8 is closed when blood is pumped out from the right ventricle 15 to the lungs. During this period, blood is filled into the right atrium 6. Thereafter, the tricuspid valve 8 is opened to fill the right ventricle 15 with blood from the right atrium 6. Free edges of leaflets of the tricuspid valve 8 are connected via chordae tendinae 10 to papillary muscles 12 for controlling the movements of the tricuspid valve 8. Blood from the right ventricle 15 is pumped through the pulmonary valve 20 to the pulmonary artery 22 which branches into arteries leading to each lung. Blood from the lungs are lead through pulmonary veins 28 into the left atrium 26 of the heart 1. The mitral valve 30 controls blood flow between the left atrium 26 and the left ventricle 17. The mitral valve 30 is closed when blood is pumped out from the left ventricle 17 to the aorta 34 and the arteries of the body. During this period, blood is filled into the left atrium 26. Thereafter, the mitral valve 30 is opened to fill the left ventricle 17 with blood from the left atrium 26. Free edges of leaflets of the mitral valve 30 are connected via chordae tendinae 11 to papillary muscles 13 for controlling the movements of the mitral valve 30. Blood from the left ventricle 17 is pumped through the aortic valve 32 into the aorta 34 which branches into arteries leading to all parts of the body.

The function of the heart 1 may be impaired by any of the heart valves not functioning properly. The heart valves may lose their ability to close properly due to e.g. dilation of an annulus around the valve or a leaflet being flaccid causing a prolapsing leaflet. The leaflets may also have shrunk due to disease, e.g. rheumatic disease, and thereby leave a gap in the valve between the leaflets. The inability of the heart valve to close will cause a leak backwards, so called regurgitation, through the valve, whereby the function of the heart 1 will be impaired since more blood will have to be pumped through the regurgitating valve.

Referring now to FIGS. 2a-2c, an apparatus 42, which may be used in treatment of a regurgitating heart valve, will be generally described. The apparatus 42 is arranged to be implanted into a patient for providing a permanent or at least long-term treatment. The apparatus 42 comprises a valve means 52, which is transferable between an open state, as shown in FIG. 2a, allowing blood flow past the valve means 52, and a closed state, as shown in FIG. 2b, preventing blood flow past the valve means 52. The valve means 52 is arranged to make contact with surrounding tissue in its closed state for sealing a blood flow path. As illustrated in FIGS. 2a-b, the valve means 52 has a greater radial extension in the closed state than in the open state for making contact with tissue. The valve means 52 will release the contact in its open state to allow blood flow, wherein the valve means 52 in its open state will be arranged within the path of the blood flow. Different embodiments of the valve means 52 will be described in further detail below with reference to FIGS. 6-7.

The apparatus 42 further comprises an anchoring means 54. The anchoring means 54 is arranged to fix the position of the apparatus 42 in a patient. The anchoring means 54 is arranged to engage with tissue for fixing the position of the apparatus 42. Different embodiments of the anchoring means 54 will be described in further detail below with reference to FIGS. 3-4.

The apparatus further comprises a connecting means 46, which connects the valve means 52 with the anchoring means 54. The connecting means 46 provides a spacing between the anchoring means 54 and the valve means 52. This implies that the apparatus 42 may be arranged in an elongate form and may be arranged in a small diameter. This facilitates insertion of the apparatus 42 into the patient, since the apparatus 42 may be inserted through a small incision. In FIG. 2c, the cross-section of the apparatus 42 at the anchoring means 54 and at two positions in the valve means 52 are shown below a side view of the apparatus 42. The cross-section of the apparatus 42 when implanted is shown immediately below the view of the apparatus 42. Further below, the cross-section of the apparatus 42 when compressed during insertion is shown. The valve means 52 and the anchoring means 54 are inserted in sequence and therefore the diameter of the device will not be an accumulation of the diameters of the valve means 52 and the anchoring means 54. Instead, the apparatus 42 may be compressed to a very small diameter as shown in FIG. 2c. Further, the connecting means 46 provides a possibility to fix the position of the valve means 52 by the anchoring means 54 engaging an appropriate site in the vicinity of the desired position of the valve means 52. The anchoring means 54 is not intended to engage tissue at the exact positioning of the valve means 52. The connecting means 46 also provides a surface or position, to which the valve means 52 is attached.

The apparatus 42 is arranged to be inserted in a minimally invasive manner into the patient. The apparatus 42 may be inserted endoscopically through a small diameter or be guided through the vascular system of the patient by means of a catheter-based technique. In the latter case, the apparatus 42 may be introduced into the vascular system through a puncture in e.g. the groin or the neck of the patient. The apparatus 42 may be held in a compressed state during insertion for providing as small diameter as possible of the apparatus 42. Further, the apparatus 42 may comprise a channel or groove for receiving a guide wire through the apparatus 42, such that the apparatus 42 may be guided to the correct position sliding on the guide wire.

Referring now to FIGS. 3-4, different embodiments of the anchoring means will be described. The anchoring means may be realised in any manner providing engagement with tissue for fixing the position of the apparatus. The anchoring means may thus comprise hooks, barbs, spikes or any other means for engaging with or partially or wholly penetrating a tissue portion. The anchoring means may also or alternatively comprise an element which is arranged for contacting a tissue portion for fixing the position. This element may be accomplished in a tubular or ring-like form for engaging an inner wall of a structure in the blood circulatory system, such as a vessel wall or an atrium wall. The element engages the inner wall to create contact along a circumference of the element. Preferably, the element is pushed towards the inner wall by an internal strive to expand its radius. The anchoring means may, as a further alternative, be arranged to contact a tissue portion at an opposite side of a tissue wall to the position of the valve means. The anchoring means may thus form a contact surface with the tissue portion which is larger than a penetration hole through the tissue portion for fixing the position of the apparatus.

As shown in FIG. 3a-c, the anchoring means 54 may comprise a tubular expandable element 55, which is arranged to make contact with a blood vessel wall along its circumference. The tubular element 55 may be a stent. The stent 55 may be self-expandable having an internal strive to expand into contact with the vessel wall. Alternatively, the stent 55 may be expanded by means of an external force, such as an inflation of a balloon from inside the stent 55. The stent 55 may be formed of threads or struts that constitute a zig-zag pattern. The stent 55 may be inserted into the patient in a compressed shape having a small radius and be expanded when placed in the desired position. As shown in FIG. 3a, the connecting means 46 branches into two arms 58 which are attached to diametrically opposite positions of the stent 55. As shown in FIG. 3b, the connecting means 146 may alternatively branch into two arms 158 which are attached to struts of the stent 55 which are close to each other or immediately adjacent each other. Further, as shown in FIG. 3c, the connecting means 246 may be arranged to assume a prebent shape such as to provide a connection between an anchoring means 54 and a valve means 52, which are not to be placed in line with each other within the patient. The connecting means 246 may alternatively be flexible such that it may be forced to a desired shape within the patient by using e.g. a preshaped catheter. As a further alternative, the connecting means 246 may be flexible such that it centers itself within the blood flow in which it is located.

As shown in FIG. 3d, the anchoring means 154 may alternatively comprise a plurality of threads or struts 155 that are resilient or spring-like such that they have an inherent strive towards assuming a shape having contact with an inner wall of an atrium over a substantial length of the thread 155. The thread 155 may be elliptic or circular for contacting the atrium wall. The anchoring means 154 may comprise a plurality of threads 155 such that a large contact area is created with the atrium wall. The threads 155 may be symmetrically distributed such that contact is symmetrically achieved with the atrium wall.

In FIGS. 3a-d, the anchoring means is arranged on an "inflow" side of the valve means, that is the valve means permits blood flow from the direction of the anchoring means past the valve means. This is suitable when the valve means is to be arranged in the mitral or tricuspid valve and the anchoring means is to be arranged in a blood vessel or a heart atrium for fixing the position of the apparatus. The embodiments of the anchoring means shown in FIGS. 4a-f, which will be described further below, are arranged on an "outflow" side of the valve means, that is the valve means permits blood flow past the valve means towards the anchoring means. This is suitable e.g. when the valve means is to be arranged in the mitral or tricuspid valve and the anchoring means is arranged to fix the position of the apparatus by engaging ventricular tissue.

Figure 4A:
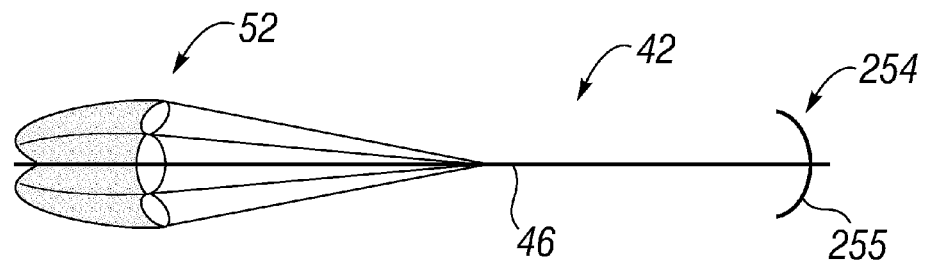

As shown in FIG. 4a, the anchoring means 254 may comprise a disk-shaped element 255 to be arranged in contact with a heart wall portion, such as a ventricular wall or interventricular septum. The connecting means 46 will extend through the heart wall and the disk-shaped element 255 will prevent the anchoring means 254 from migrating through the heart wall. The anchoring means 254 may further comprise a hook, barb or the like for engaging the heart wall. The disk-shaped element 255 may be compressed for insertion through the heart wall and may assume its disk-shape when a compressing force is released.

Figure 4B:
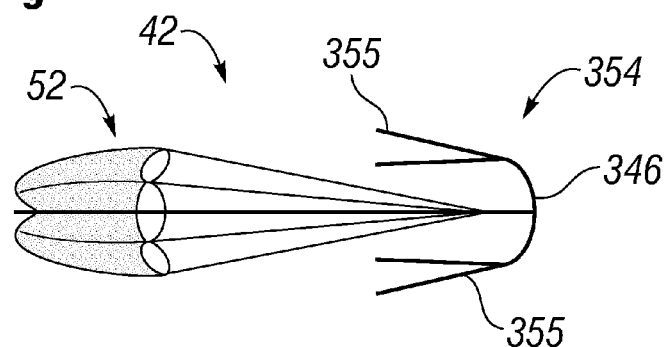

As shown in FIG. 4b, the anchoring means 354 may comprise two or more hooks 355 for engaging chordae tendinae. The connecting means 346 branches off into essentially transversal branches extending to the respective hooks 355. The hooks 355 are arranged to capture chordae tendinae within the hooks 355 for fixing the position of the apparatus 42.

Figure 4C:
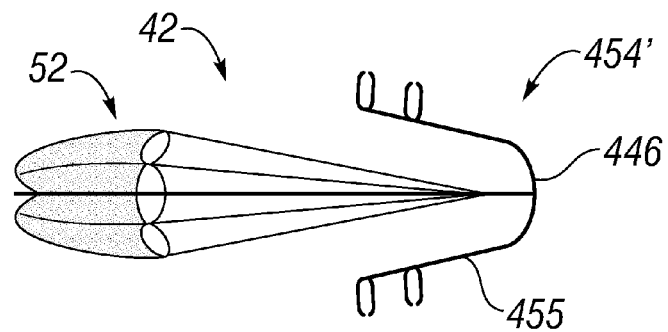

As shown in FIG. 4c, the anchoring means 454 may comprise a plurality of clips 455 for engaging papillary muscles. The clips 455 are arranged to grab around the papillary muscles for fixing the position of the apparatus 42. Again, the connecting means 446 branches off into branches extending transversally and even backwards to one or more clips 455, respectively.

Figure 4D:
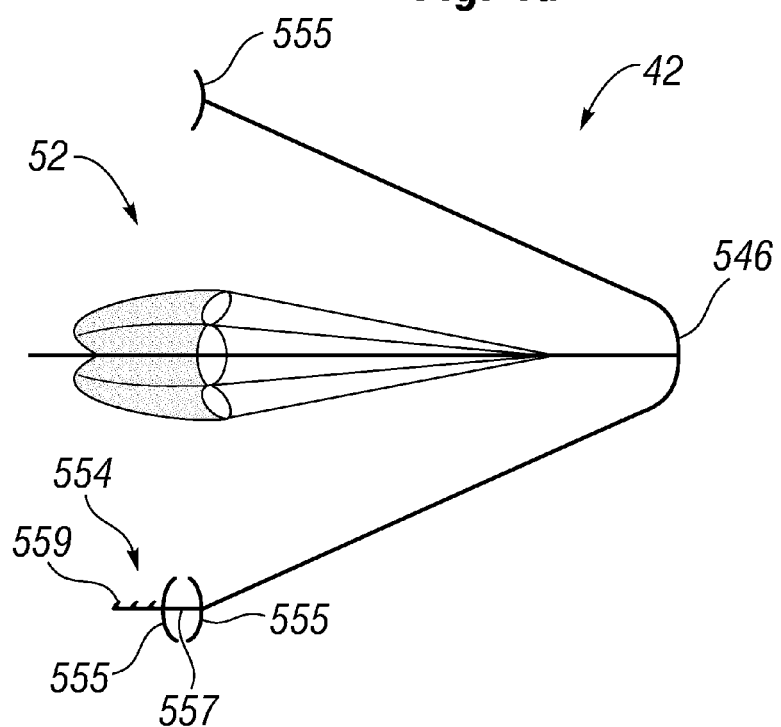

As shown in FIG. 4d, the anchoring means 554 may comprise a plurality of disk-shaped or bar-shaped elements 555 arranged to engage a valve annulus. The connecting means 546 branches off into branches extending backwards such that the anchoring means 554 may be arranged in engagement with a valve annulus where the valve means 52 is arranged in the valve. The engagement with the valve annulus may be accomplished by two disk-shaped or bar-shaped elements 555 engaging opposite sides of the annulus. The anchoring means 554 may then further comprise a connection 557 between the disk-shaped elements 555, wherein the connection 557 is arranged to extend through the valve annulus. The connection 557 may further comprise projections 559, which may be used for fixing the position of one of the disk-shaped elements 555 along the connection 557. The disk-shaped element 555 may then be pushed or forced over the projection 559 and be held in this position. Thus, the distance between the two disk-shaped elements 555 is adjustable to fit the thickness of the valve annulus and to thereby attach the apparatus to the valve annulus.

Figure 4E:
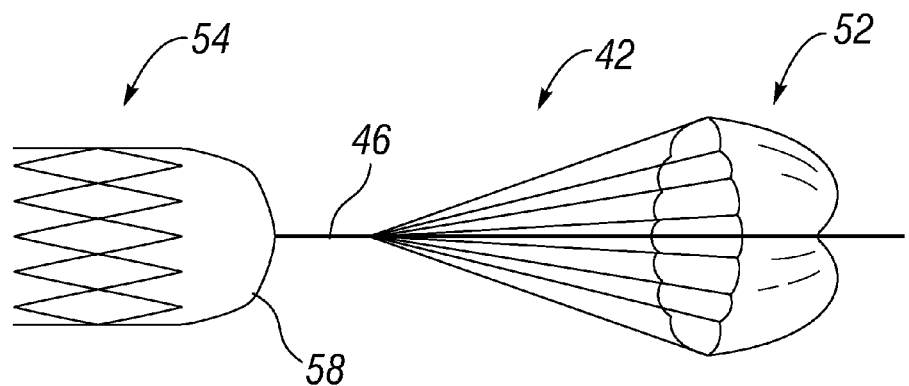

As shown in FIGS. 4e-f, the anchoring means arranged on an "outflow" side of the valve means may comprise a stent 55 as described above with reference to FIGS. 3a-c. As shown in FIG. 4e, the connecting means 46 may branch into two arms 58 which are attached to diametrically opposite positions of the stent 55 and are attached to an end of the stent 55 which is closest to the valve means 52. As shown in FIG. 4f, the two arms 58 of the connecting means 46 may alternatively be attached to an end of the stent 55 which is farthest away from the valve means 52. This embodiment may be arranged in a very compact form with the valve means 52 being arranged close to the anchoring means 54.

As shown in FIG. 4g, the apparatus 42 may comprise two anchoring means 54, 254, which are arranged on an "inflow" and "outflow" side of the valve means 52, respectively. The two anchoring means 54, 254 may cooperate to securely fix the position of the apparatus 42 within the patient.

The anchoring means may be made of a shape memory material, such as Nitinol or a shape memory polymer. This implies that the anchoring means may be self-expandable to assume its pre-programmed shape. This is especially suitable where the anchoring means comprises an element to be expanded within the patient. However, ordinary stainless steel, stainless spring steel or any other metal might be used. The connecting means could be made of similar material as the anchoring means. The connecting means may then be an extension of the anchoring means without the need of any welding or attachment point between the connecting means and the anchoring means.

The connecting means may be realised as an elongate body providing a spacer and connection between the valve means and the anchoring means. The connecting means may have branches for extending to different parts of an anchoring means in order to provide a more secure connection between the anchoring means and the connecting means or in order to create a connection between separate anchoring means. The connecting means may e.g. have a round or flat cross-section. The connecting means may be tubular or have a groove, e.g. U- or C-shaped, for receiving a guide wire during insertion of the apparatus 42. The connecting means may alternatively be formed from a solid material. The connecting means may as a further alternative be made of threads or struts forming a grid of zig-zag or scissor-shaped thin material. The connecting means may still be hollow or present a groove while being shaped as a grid. The connecting means may be arranged in a flexible material or in a shape memory material such that the connecting means may be fitted to a specific track after being inserted in the body. As a further alternative, the connecting means may be formed from a plurality of sequentially arranged segments, whose mutual relationship may be controlled or adjusted.

Figure 5I:
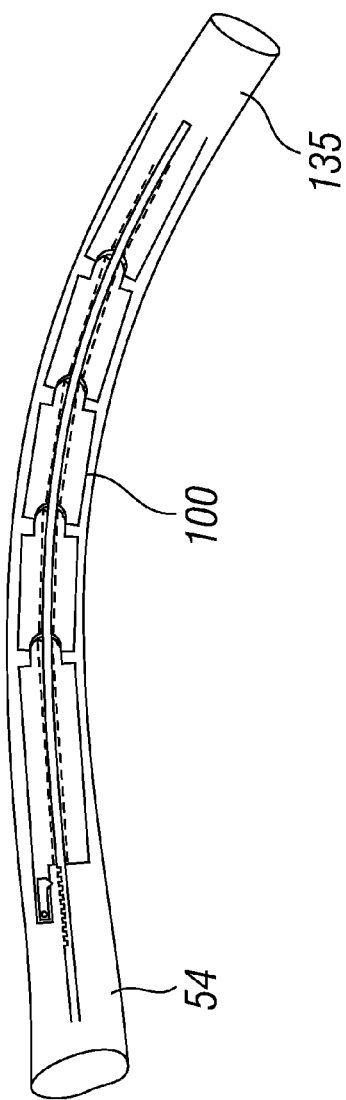

Referring now to FIGS. 5a-i, a segment-based embodiment of the connecting means will be described. In FIG. 5a, an apparatus 42 is shown with a connecting means 46 being arranged between the anchoring means 54 and the valve means 52. In FIG. 5b, a portion of the connecting means 46 marked with circle B in FIG. 5a, is shown in greater detail. The connecting means 46 comprises sequential connecting segments 100. In FIG. 5c, two connecting segments 100 are indicated in even greater detail. The connecting segments 100 comprise a head 102, which may e.g. be spherically shaped, and an end 104 with a recess 105 corresponding to the shape of the head 102, such that the recess 105 may receive a head 102. The recess 105 is slightly larger than the head 102 to allow the head 102 to be rotated within the recess for adjusting the mutual relationship of adjacent segments 100. The head 102 comprises a small protrusion or knob 106 and the end 104 comprises a small notch 108 for receiving the protrusion 106. When the protrusion 106 is positioned in the notch 108, the segments 100 are aligned. The protrusion 106 may be pushed out of the notch 108 by applying a small force to the connecting means 46. There may be multiple protrusions 106 and notches 108 on the head 102 and end 104, respectively, so that the head 102 and end 104 may engage in multiple different relationships in order to lock the connecting segments 100 in different desired angles. The segments 100 further comprise a channel 110 for receiving a locking wire. By locking the shape of the locking wire when extending through the segments 100, the mutual relationships of the segments 100 is locked, as will be further described below. In FIG. 5d, a front segment 113 of the connecting means 46 is shown. The front segment 113 comprises an end 104 similar to the ends 104 of the other segments 100. The front segment 113 comprises a blind bore 114 in its end 104. The locking wire 112 is received in the blind bore 114 and attached to the front segment 113 within the bore 114. The front segment 113 provides a non-flexible part of the connecting means 46 and may have a longer longitudinal extension than the other segments 100. The front segment 113 is arranged at the end of the connecting means 46 closest to the valve means 52.

In FIG. 5e, a rear segment 116 of the connecting means 46 is shown. The rear segment 116 comprises a head 102 similar to the heads 102 of the other segments 100. The rear segment 116 also comprises a channel 110 for receiving the locking wire 112. The rear segment 116 also comprises at its end a locking mechanism 101 for locking the shape of the locking wire 112. The rear segment 116 also comprises welding or fixation points 118 for attaching the rear segment 116 to the anchoring means 54 or to arms 58, 158 or branches of the connecting means 46, which in turn are attached to the anchoring means 54.

The locking mechanism 101 will now be further described with reference to FIGS. 5f-h. In FIG. 5f, the parts of the locking mechanism 101 are shown. The locking mechanism comprises an arm 120, which is a rotatably attached to the end segment 116 in a rotation point 122. The arm 120 may be attached to the end segment 116 by means of a pin extending through a hole in the arm 120 and engaging the end segment 116. The arm 120 has a protrusion 124, which may be rotated into engagement with grooves 126 in the locking wire 112. The protrusion 124 may be e.g. wedge-shaped as shown in FIG. 5f. An adjustment wire 128 may be attached and detached to the locking wire 112. The adjustment wire 128 may be arranged to extend outside the patient for providing control of the position of the locking wire 112 from outside the patient during insertion of the apparatus 42. The locking wire 112 and the adjustment wire 128 may comprise corresponding notches 133, 134 and grooves 130, 132 for providing an attachment between the wires. Operation of the locking mechanism 101 is shown in FIGS. 5g-h. The adjustment wire 128 is arranged in a fixation tube 136, which covers the attachment between the adjustment wire 128 and the locking wire 112 for preventing detachment of the wires. When the fixation tube 136 is pulled backwards or withdrawn from the patient, the adjustment wire 128 can be detached from the locking wire 112. In FIG. 5g, the locking arm 120 is shown in engagement with the locking wire 112 locking the shape of the locking wire 112. As shown in FIG. 5h, the fixation tube 136 can also be moved forward to rotate the locking arm 120, so that the wedge-shaped protrusion 124 is forced out of the groove 126 and thereby the lock is opened. The mutual relationships of the segments 100 of the connecting means 46 can then be adjusted again. When the locking wire 112 is stretched and locked instead, the friction between the spherical-shaped recess 105 in a segment and the head 102 of the adjacent segment will fix the segments in a certain position relative to each other.

Orientation of the segments 100 in relation to each other may in one embodiment, as shown in FIG. 5i, be made by means of a preshaped catheter 135 that force the segments 100 to line up according to the shape of the catheter 135 before the segments 100 are locked relative to each other. The catheter 135 may have any shape to mimic the desired track of the connecting means 46. The catheter 135 may have a shape memory such that the catheter 135 may be activated to assume its shape when the apparatus 42 has been fixed in the body.

Another embodiment for orientating the segments 100 in relation to each other is to attach threads 135' to the segments 100. By pulling in the threads 135', at least one segment 100 can be steered to the correct position. When all segments 100 have been correctly placed, the segments 100 may be locked relative to each other. The thread 135' may be double forming a loop that engages a hook or loop on the segment 100. When the steering is completed, the thread 135' may be pulled out.

As shown in FIG. 5j, the connecting means 46 may provide a possibility to disengage the valve means 52 from the anchoring means 54. The valve means 52 may in time suffer structural damage or calcification and may therefore need to be replaced. By disengaging the implanted valve means 52, there is only a need to replace the valve means 52. The connecting means 46 may therefore comprise a lock 137 for enabling detachment of the valve means 52 from the anchoring means 54. Where an embodiment of the connecting means 46 as shown in FIGS. 5a-j is used, the lock 137 may e.g. be provided in the front segment 103. In FIG. 5j, the lock 137 is enlarged showing one possible embodiment. The lock 137 has a male portion 138 with a threaded winding 139, which is fitted into a female portion 140 with a threaded groove 141. Thus, the male portion 138 may be screwed on or off the female portion 140 for engaging or releasing the lock. It should be appreciated that numerous other embodiments of the lock are possible. For example, the lock may be formed from a hook engaging a loop or a pin engaging a bore.

Referring now to FIGS. 6-7, different embodiments of the valve means will be described. Generally, the valve means is arranged to seal the native heart valve or blood vessel in which it is placed in order to prevent backflow in the valve or the vessel. The valve means is therefore oversized so that it will certainly contact and seal against the leaflets of the native valve or against the wall of the vessel. The valve means will further provide a surface facing forward flow in the native heart valve or the vessel, wherein the surface is arranged in such a manner that when exposed to blood flow in the forward direction, the blood flow will force the valve means to open.

According to a first embodiment shown in FIG. 6a, the valve means 52 comprises a flap 44 which symmetrically encircles the connecting means 46. The flap 44 is attached to the connecting means 46 around its entire circumference in a longitudinal attachment point 90 forming a fluidtight attachment around the connecting means 46. The flap 44 is hinged in the attachment point 90 such that it is movable between an open position where it extends mainly along the connecting means 46 and a closed position, as shown in FIG. 6a, where it extends in a mainly transverse direction to the connecting means 46. The flap 44 has a contact surface 92 which faces the forward flow in the native heart valve or the vessel and which is arranged to contact the leaflets of the native heart valve or the vessel wall in the closed position of the flap 44. When moving into the closed position, the flap 44 will move towards increasingly extending in a transverse direction to the connecting means 46. The contact surface 92 will then come into contact with the leaflets of the native heart valve or the vessel wall before the flap 44 extends in a fully transverse direction to the connecting means 46. The flap 44 will therefore contact the leaflets of the native heart valve or the vessel wall in a coaptation area 94 of the contact surface 92 corresponding to a short distance along the leaflets of the native heart valve or the vessel and the boundary of the coaptation area 94 forming a closed circumferential shape such that coaptation is achieved around the entire valve means 52. This oversizing of the flap 44 also implies that the connecting means 46 will not need to be precisely centrally positioned in the native heart valve or the vessel.

The contact surface 92 has a rim 96 at the end which comes in contact with the leaflets of the native heart valve or the vessel wall. The rim 96 is strengthened by enforcement strings 53 connecting the rim 96 with a fixation point 98 on the connecting means 46. The enforcement strings 53 stabilize the shape of the flap 44 in the closed position. The enforcement strings 53 may be an integrated part of the flap 44 or they may be attached to the flap 44 by e.g. gluing or a knot. The enforcement strings 53 also prevent the flap 44 from turning over, i.e. to extend in the opposite direction along the connecting means 46 from the attachment point 90. If the flap 44 would turn over it would no longer function to allow forward flow nor preventing backflow past the valve means 52.

The flap 44 of the valve means 52 has an internal strive to assume the shape of the closed position. When inserted and released from a restraining cover, the valve means 52 will open like a parachute, make contact with the leaflets of the native heart valve or the vessel wall and form a valve that only allows flow in one direction.

The second embodiment of the valve means is shown in FIG. 6b. This valve means 152 comprises a flap 144, which is divided into subsections 145 by means of flap enforcement parts 147. This gives the flap 144 a more stable umbrella-like or parachute-like shape and therefore fewer enforcement strings 153 are needed. In fact, the enforcement strings 153 may be completely omitted if the flap enforcement parts 147 are sufficiently strong or rigid to prohibit a turning over of the flap 144. The enforcement strings 153 are attached to the flap 144 at the interface between two adjacent subsections 145 and connect the flap 144 to a fixation point 198. As for the first embodiment, the flap 144 is attached symmetrically around an attachment point 190 of the connecting means 46 and provides a contact surface 192 with a coaptation area 194.

In the third embodiment shown in FIG. 6c, the valve means 252 comprises several flaps 244. The flaps 244 are attached to a common attachment position 290 around the connecting means 46. Each flap 244 has a contact surface 292 with a coaptation area 294 and the flap 244 is movable to put the coaptation area 294 of the contact surface 292 in contact with the leaflets of the native heart valve or the vessel wall. The flaps 244 are broadening towards the coaptation area 294. Further, the flaps 244 are overlapping and arranged as the leaves of a hibiscus flower so as to form a tight seal between them when extending to make contact with the heart valve or the vessel wall. The flaps 244 further have a strengthened base 296 close to the attachment position 290. The strengthened base 296 will prevent the flap 244 from turning over due to backflow in the heart valve or the vessel.

Figure 7A:
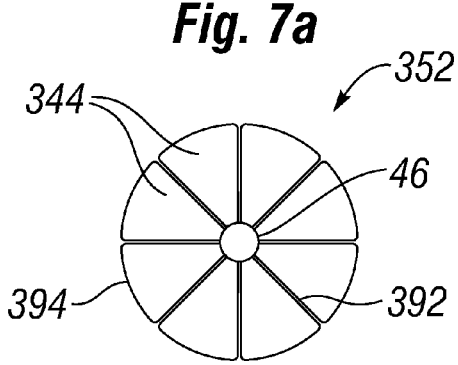
FIGS. 7a-f are views of a further embodiment of the valve means.
Figure 7B:
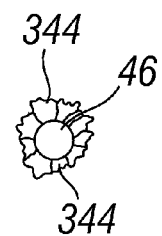
Figure 7C:
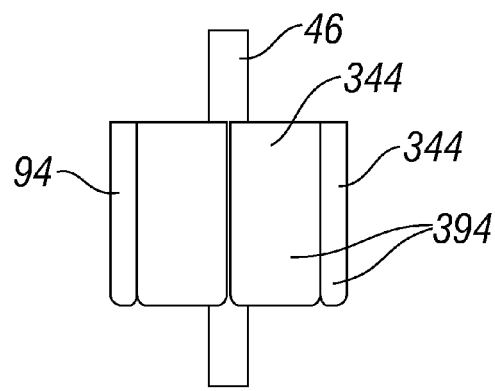

In the fourth embodiment shown in FIGS. 7a-d, the valve means 352 comprises several flaps 344 which are arranged side-by-side encircling the connecting means 46. As indicated in FIG. 7c showing a perspective view of the valve means 352, each flap 344 comprises a contact surface 392 with a coaptation area 394. The flaps 344 are wedge-formed with the narrow end towards the connecting means 46 and the broad end arranged to make contact with the native heart valve or the vessel wall. As indicated in FIG. 7a showing a cross section of the valve means 352 when inserted in a native heart valve or a vessel, adjacent flaps 344 extend along each other and are arranged close together such that adjacent surfaces present respective coaptation areas 392, which will be in close contact with each other to prevent leakage between the flaps 344. In FIG. 7a the valve means 352 is depicted in the closed position in which it is arranged to make contact with the native heart valve or a vessel wall. When blood flows forward through the open valve means 352 it will take the shape depicted in FIGS. 7b and 7d. Now the wedge-shaped flaps 344 are pressed against the connecting means 46 by the force of the blood stream and the valve means 352 is open. This embodiment of the valve means 352 would be especially effective in irregular shaped orifices, as for instance in severe calcified native heart valves.

Figure 7D:
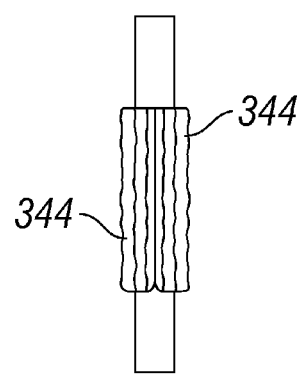
Figure 7E:
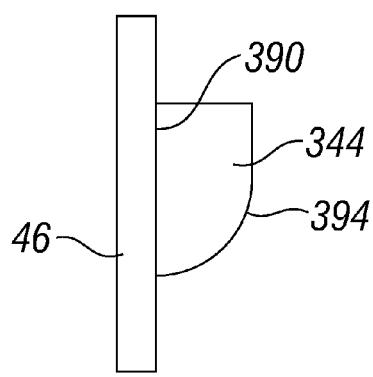
Figure 7F:
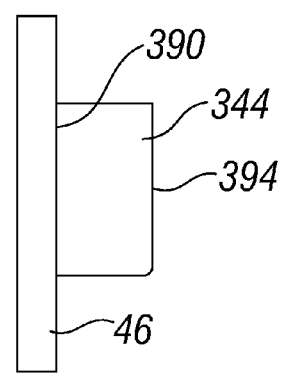

In FIGS. 7e and 7f, attachment of the flaps 344 to the connecting means 46 is shown. The flaps 344 are attached to the connecting means 46 in an attachment line 390 along a longitudinal direction of the connecting means 46. The flap 344 may be attached to the connecting means 46 over the entire length of the flap 344 (see FIG. 7e) or over a part of the length of the flap 344 (see FIG. 7f). The longer attachment line 390 makes enforcement strings unnecessary.

As shown in FIGS. 7b and 7d, the flaps 344 will collapse towards the connecting means 46 when exposed to blood flow in the forward direction. The flap material is very thin to allow the flap 344 to contract towards the connecting means 46 when exposed to the blood flow.

The flap or flaps of the valve means according to any embodiment are preferably made of biological tissue, which has been treated with glutaraldehyde or any tanning or fixation medium. The biological tissue may e.g. be tissue from pericardium or heart valve of an animal.

The valve means may alternatively be made of polymers, such as polyurethane, polyvinyl, polyethylene, polyethylene terephthalate (PET), polytetrafluoroethylene (PTFE), or rayon. However, the flap or flaps may also be made of a shape memory material, such as Nitinol or shape memory polymers, whereby an ultrathin flap having a thickness of 3-4 µm may be formed.

The valve means may be covered with active drugs. One such drug would be heparin, for prevention of clot formation in the blood circulation system of the patient. Another drug would be nitric oxide, which also prevents clot formation, and also a combination of heparin and nitric oxide is possible.

Figure 11A:
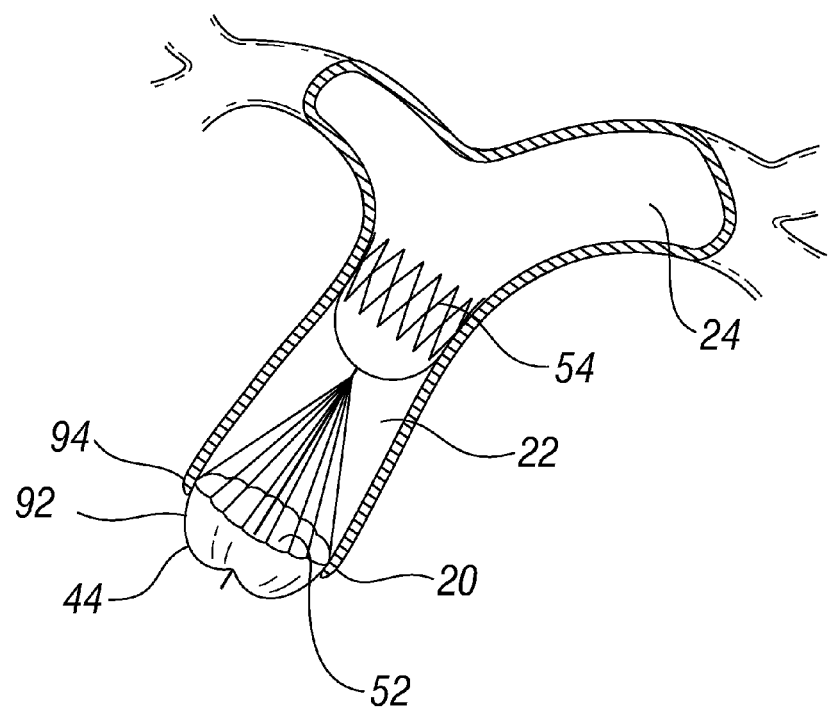
Figure 11B:
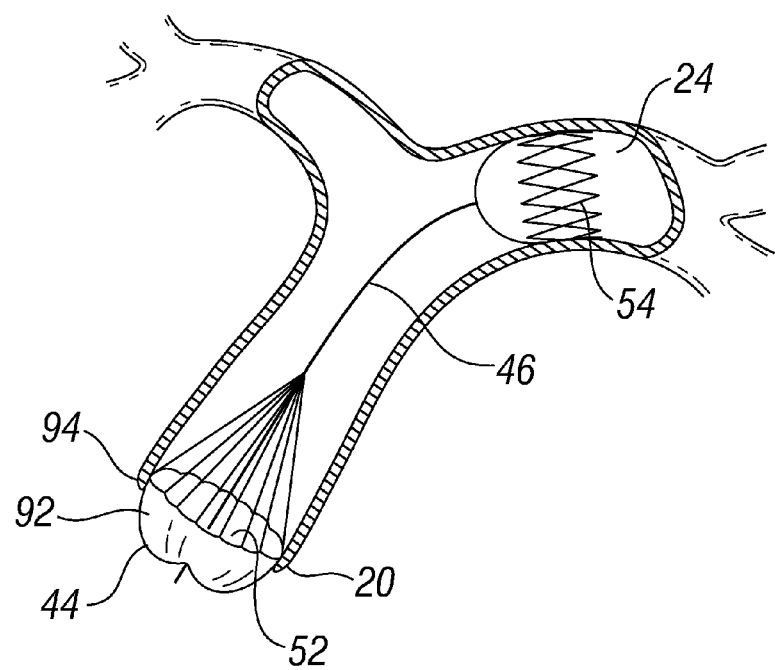
Figure 11D:
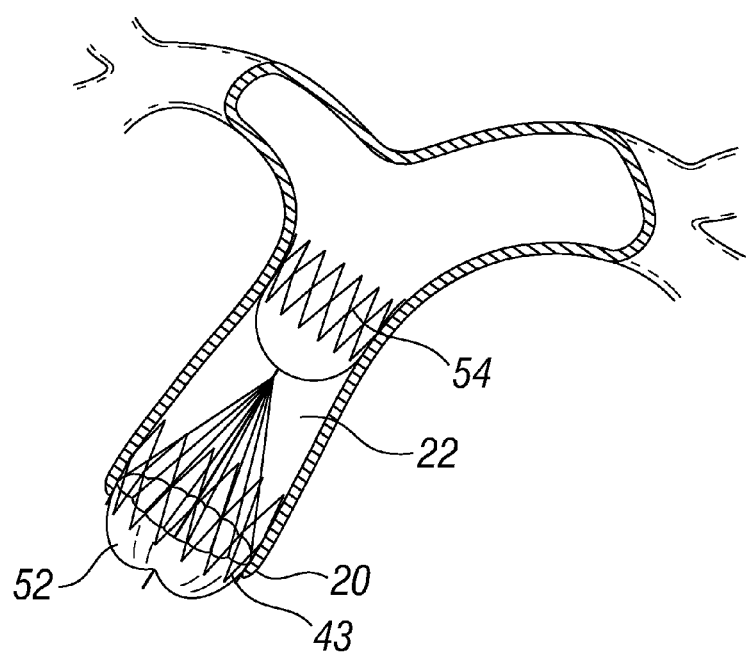
Figure 12:
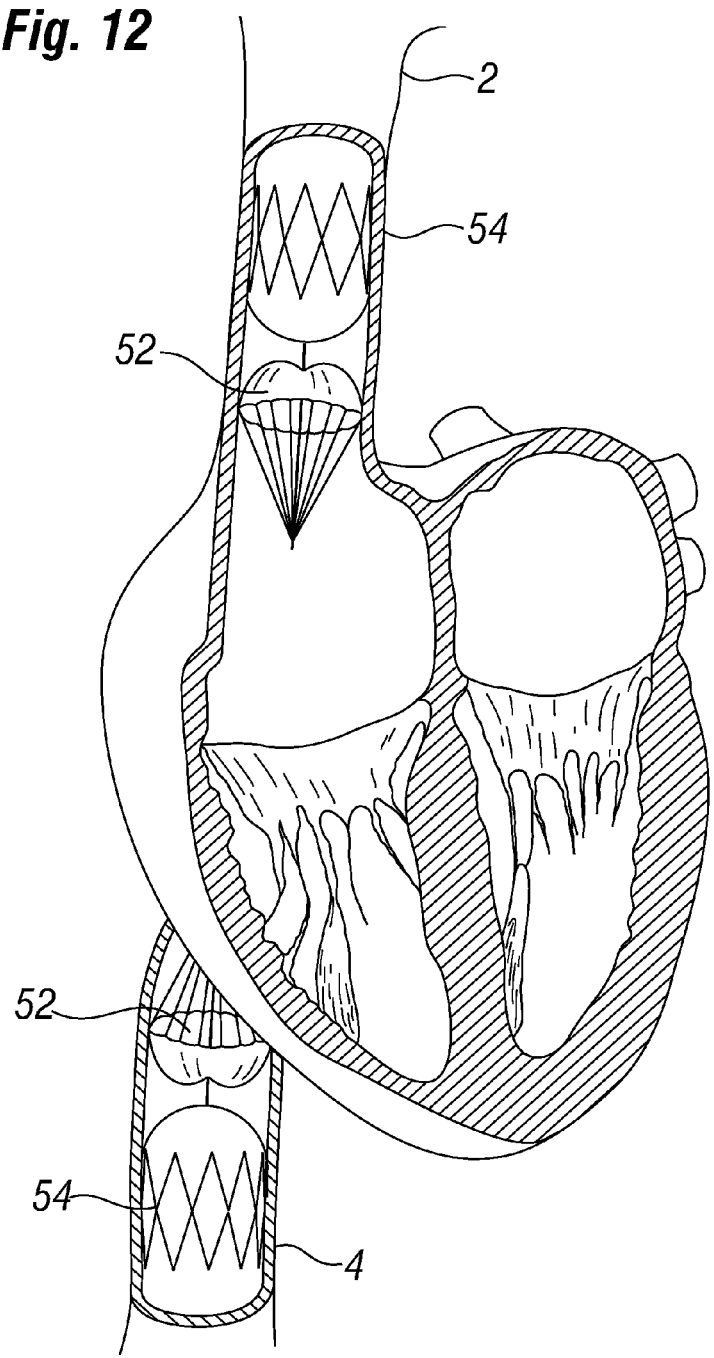
FIG. 12 shows blood flow controlling apparatuses being inserted in the superior vena cava and the inferior vena cava.

Referring now to FIGS. 8-12, the use of an apparatus 42 for controlling blood flow in a patient will be generally described. The apparatus 42 may be used for treating a regurgitating heart valve, as illustrated in FIGS. 8-9, or for controlling blood flow through an artery or a vein, as illustrated in FIGS. 10-12.

FIGS. 8a-f illustrate the treatment of a regurgitating mitral valve 30. The mitral valve 30 comprises a posterior leaflet 35 and an anterior leaflet 37. The leaflets 35, 37 move for opening and closing the mitral valve 30.

In FIG. 8a, a regurgitating mitral valve 30 is shown, where the posterior and anterior leaflets 35, 37 are not able to close the valve properly. The valve 30 has a leak 31 in a central position of the valve 30. In FIG. 8b, the mitral valve 30 with an implanted apparatus 42 is shown. The valve means 52 of the apparatus 42 is placed in the leak 31 such that a coaptation area 94 between the valve means 52 and the leaflets 35, 37 is created for closing the leak 31. The valve means 52 in its closed state makes contact with the leaflets in a short distance along the contact surface 92 such that a cylindrical surface constitutes the coaptation area 94 such that a tight seal is created. In FIG. 8c, another shape of the valve means 52 is shown for treatment of the leak 31. In this case, the valve means 52 has a rectangular or an oval shape in its closed state, which may also effectively form a coaptation area 94 for tightly sealing the leak 31. In FIGS. 8d and 8e, a mitral valve 30 having a leak 31 positioned asymmetrically in the valve 30 is shown. The apparatus 42 is implanted such that the valve means 52 is centrally positioned within the leak 31 for forming a coaptation area 94 in order to tightly seal the leak 31. In FIG. 8f, a schematic cross-section of the heart 1 is shown illustrating the placement of the valve means 52 within the mitral valve 30. The valve means 52 has a greater extension along the blood flow between the left atrium 26 and the left ventricle 17 than the native mitral valve 30. This implies that the valve means 52 may effectively contact prolapsing leaflets that extend into the left atrium 26 and that the valve means 52 may form a tight coaptation area 94 to many different shapes of leaks in the mitral valve 30. Such a great extension of the valve means 52 along the blood flow also implies that the valve means 52 effectively may contact leaflets restrained by shortened chordae tendinae 11 inside the left ventricle 17.

Figure 9A:
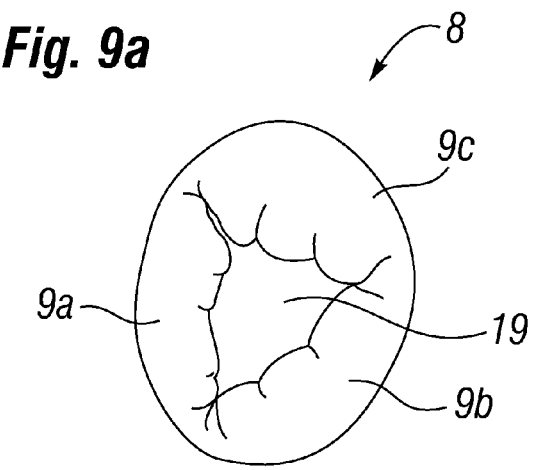
FIGS. 9a-c are schematic views of a tricuspid valve indicating a valve means of a blood flow controlling apparatus according to the invention being inserted for treating a leak in the tricuspid valve.
Figure 9B:
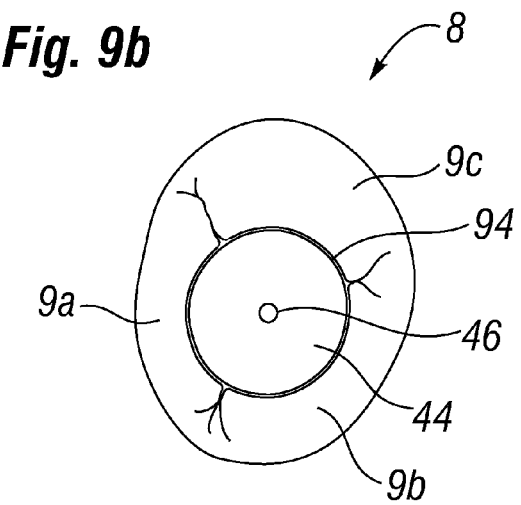
Figure 9C:
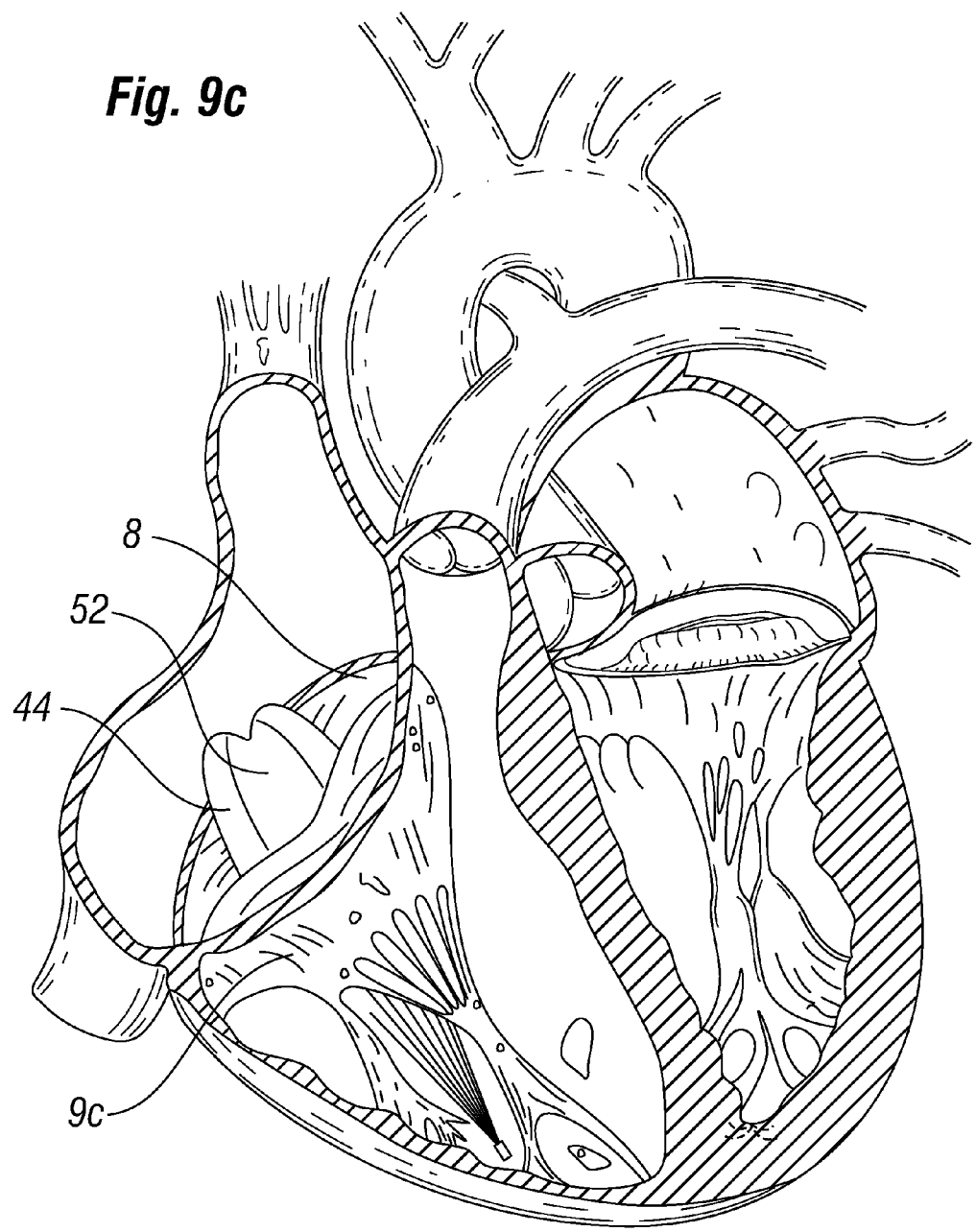

FIGS. 9a-c illustrate the treatment of a regurgitating tricuspid valve 8. The tricuspid valve 8 comprises a medial leaflet 9a, a posterior leaflet 9b and an anterior leaflet 9c. The leaflets 9a, 9b, 9c move for opening and closing the tricuspid valve 8.

In FIG. 9a, a regurgitating tricuspid valve 8 is shown, where the leaflets 9a, 9b, 9c are not able to close the valve properly. The valve 8 has a leak 19 in a central position of the valve 8. In FIG. 9b, the tricuspid valve 8 with an implanted apparatus 42 is shown. The valve means 52 of the apparatus 42 is placed in the leak 19 such that a coaptation area 94 between the valve means 52 and the leaflets 9a, 9b, 9c is created for closing the leak 19. The valve means 52 in its closed state makes contact with the leaflets in a short distance along the contact surface 92 such that a cylindrical surface constitutes the coaptation area 94 such that a tight seal is created. In FIG. 9c, a schematic cross-section of the heart 1 is shown illustrating the placement of the valve means 52 within the tricuspid valve 8. The valve means 52 has a greater extension along the blood flow between the right atrium 6 and the right ventricle 15 than the native tricuspid valve 8. This implies that the valve means 52 may effectively contact prolapsing leaflets that extend into the right atrium 6 and that the valve means 52 may form a tight coaptation area 94 to many different shapes of leaks in the tricuspid valve 8. Such a great extension of the valve means 52 along the blood flow also implies that the valve means 52 effectively may contact leaflets restrained by shortened chordae tendinae 10 inside the right ventricle 15.

FIGS. 10a-c illustrate use of the apparatus 42 for controlling blood flow through the aorta, which may be used for treatment of a regurgitating aortic valve 32. The apparatus 42 may replace the function of the aortic valve 32.

As shown in FIG. 10a, the anchoring means 54 of the apparatus 42 may be placed in the aorta 34 for fixing the position of the apparatus 42. The anchoring means 54 comprises a stent 55, which is expanded in contact with the aorta 34 for fixing the position of the apparatus 42. The anchoring means 54 is preferably arranged on the "outflow" side of the valve means 52 such that the valve means 52 may be arranged close to the position of the aortic valve 32. The valve means 52 is placed upstream to a position where coronary arteries 39 branches off from the aorta 34. Thus, the valve means 52 may effectively control blood flow from the left ventricle 17 to all parts of the body. The valve means 52 is arranged to make contact with the walls of the aorta 34 in a coaptation area 94 for preventing blood flow past the valve means 52. The valve means 52 releases the contact and opens when exposed to blood flow from the left ventricle 17. In FIG. 10b, a specific embodiment of the valve means 52 is illustrated. The valve means 52 comprises recesses 97 corresponding to the openings of the coronary arteries 39 to the aorta. Thus, the valve means 52 may be arranged at least partly overlapping the position in the aorta where the coronary arteries 39 branches off from the aorta. The valve means 52 will prevent blood flow between the aorta 34 and the left ventricle 17 when the valve means 52 is closed, leaving the coronary arteries 39 open to the aorta 34 in order to permit blood flow to the heart muscle. Instead of having recesses 97 in the flap 44, the valve means 52 may be positioned with the rim 96 arranged just below the coronary artery opening in the aorta 34. Thus, blood flow to the coronary arteries during diastole may occur undisturbed even when the valve means 52 is in the closed position. As a matter of fact, the valve means 52 may be positioned partly inside the left ventricle 17 such that the flap 44 is leaning on the anterior leaflet 37 of the mitral valve 30. As shown in FIG. 10c, a further stent 41 may be arranged in the aorta 34 at the position of the aortic valve 32. This stent 41 may press the malfunctioning aortic valve 32 and any calcification thereof against the wall of the aorta 34, such that the blood flow control of the valve means 52 of the apparatus 42 is not disturbed by the native aortic valve 32 if this is calcified. This stent 41 may be a covered or at least partially covered stent 41. The covered stent 41 may be positioned partly inside the left ventricle 17 in order to be arranged upstream of the coronary arteries 39. The covered stent 41 thereby provides a channel from inside the left ventricle 17 into the aorta 34.

FIGS. 11a-d illustrate use of the apparatus 42 for controlling blood flow through the pulmonary artery 22, which may be used for treatment of a regurgitating pulmonary valve 20. The apparatus 42 may replace the function of the pulmonary valve 20.

As shown in FIG. 11a, the anchoring means 54 of the apparatus 42 may be placed in the pulmonary artery 22 for fixing the position of the apparatus 42. The anchoring means 54 comprises a stent 55, which is expanded in contact with the pulmonary artery 22 for fixing the position of the apparatus 42. The anchoring means 54 is arranged on the "outflow" side of the valve means 52 such that the valve means 52 may be arranged close to the position of the pulmonary valve. The valve means 52 is placed to effectively control blood flow from the right ventricle 15 to the lungs. The valve means 52 is arranged to make contact with the walls of the pulmonary artery 22 in a coaptation area 94 for preventing blood flow past the valve means 52. The valve means 52 releases the contact and opens when exposed to blood flow from the right ventricle 15. In FIG. 11b, another positioning of the anchoring means 54 is illustrated. The anchoring means 54 is placed in the main left branch 24 of the pulmonary artery 22. The connecting means 46 may in this embodiment have a preprogrammed shape to adapt to the curve of the artery between the position of the valve means 52 and the anchoring means 54. As shown in FIG. 11c, the anchoring means 54 may alternatively be arranged on the "inflow" side of the valve means 52. The anchoring means 54 fixes the position of the apparatus 42 in a position of the pulmonary artery 22 close to the right ventricle 15. The valve means 52 may then be placed in a position in the pulmonary artery 22 upstream of a position where the pulmonary artery 22 branches into the left and right pulmonary arteries. Thus, the valve means 52 is still placed to effectively control the blood flow from the right ventricle to the lungs. As shown in FIG. 11d, a further stent 43 may be arranged in the pulmonary artery 22 at the position of the pulmonary valve 20. This stent 43 may press the malfunctioning pulmonary valve and any calcification thereof against the wall of the pulmonary artery 22, such that the blood flow control of the valve means 52 of the apparatus 42 is not disturbed by the native pulmonary valve 20. As for the stent 41, the stent 43 may also be a covered or at least partially covered stent 43.

In FIG. 12, there is shown a blood flow controlling apparatus 42 being positioned in the superior vena cava 2 and another blood flow controlling apparatus 42 being positioned in the inferior vena cava 4. The valve means 52 is arranged to make and release contact with the wall of the superior vena cava 2 and the inferior vena cava 4, respectively, for opening and closing blood flow through the vessel. A valve means 52 in the superior vena cava 2 or inferior vena cava 4 may be useful in cases of congenital defects where it is impossible to place a valve means 52 in the pulmonary artery 22. Then, the valve means 52 may instead be placed upstream in the blood circulation system, such as shown in FIG. 12.

Referring now to FIGS. 13a-k, the positioning and anchoring of different embodiments of the apparatus for placing the valve means in the mitral or tricuspid valve will be described. The valve means is arranged in the mitral or tricuspid valve for improving the valve function as described above with reference to FIGS. 8-9. The apparatus may be anchored in a number of different ways, as is shown in FIGS. 13a-k.

Depending on how the apparatus is anchored, the anchoring means is designed in different ways. It will be appreciated by those skilled in the art, that the apparatus may be designed in many other alternative ways for appropriately placing the valve means in a heart valve or within a blood vessel.

Figure 13A:
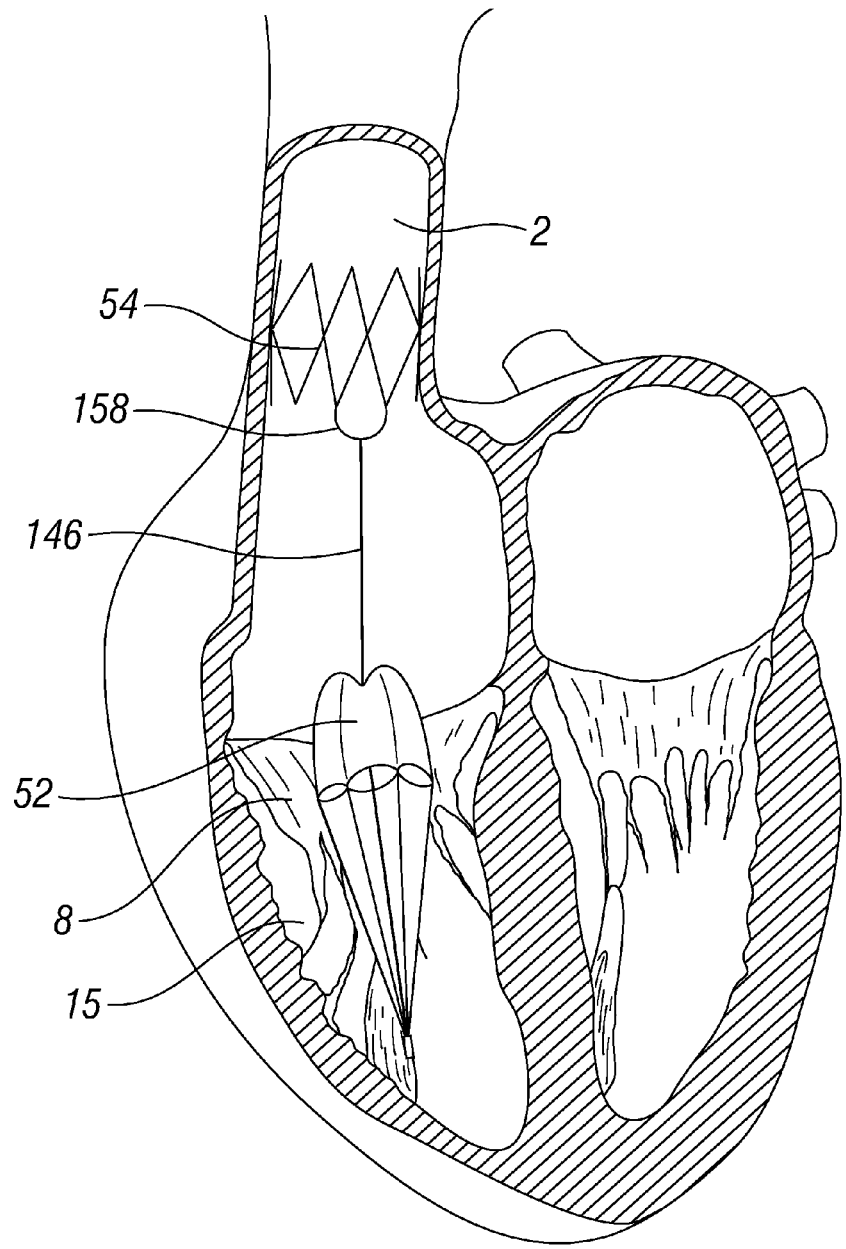
FIGS. 13a-k are schematic views of a heart showing different embodiments of the blood flow controlling apparatus being inserted in the mitral valve and tricuspid valve, respectively.
Figure 13B:
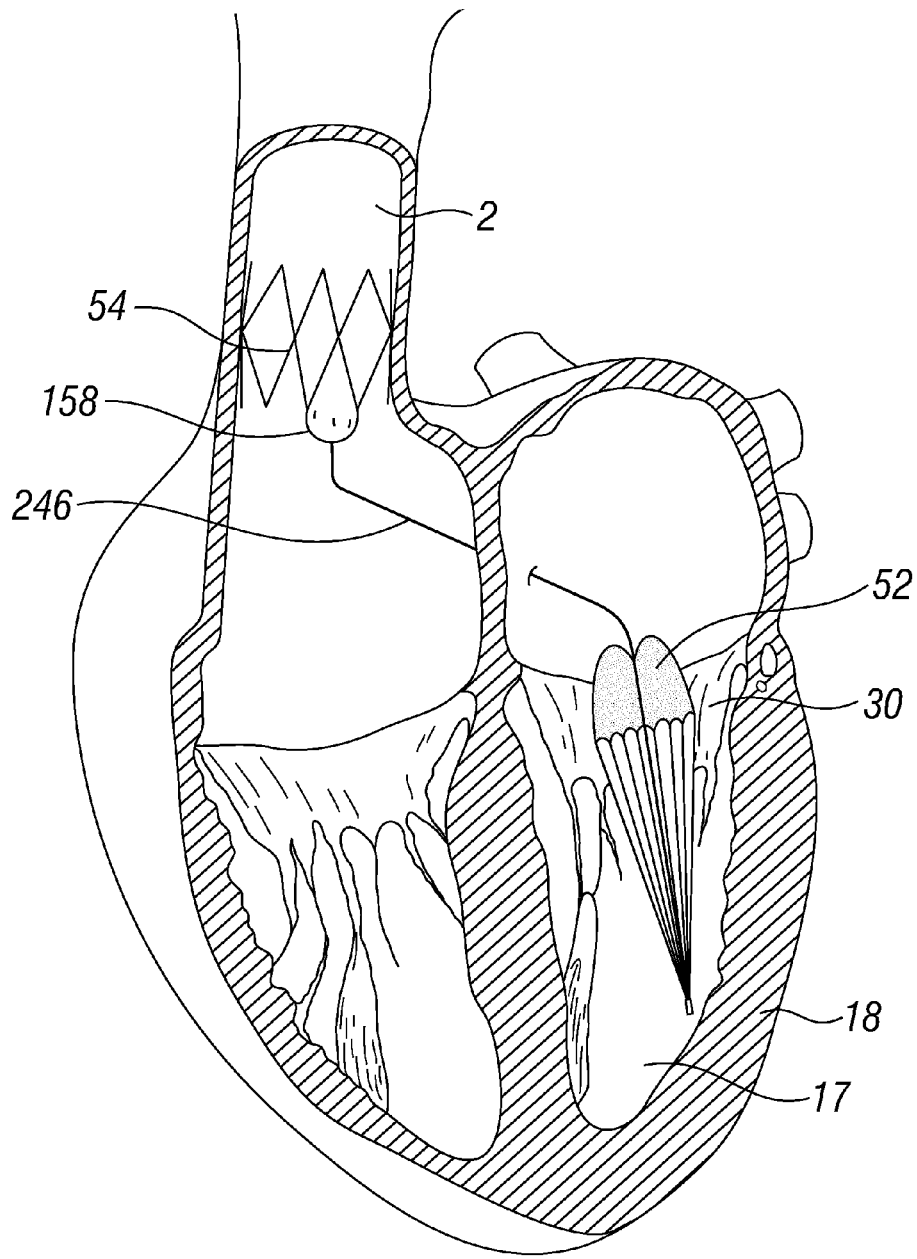

In FIG. 13a, the apparatus 42 is arranged such that the valve means 52 is placed in the tricuspid valve 8. The position of the apparatus 42 is fixed in the body by the anchoring means 54 being placed in the superior vena cava 2 for engaging the wall of the vessel. An embodiment of the anchoring means 54 as shown in FIG. 3b is used. The connecting means 146 extends through the right atrium 6 between the superior vena cava 2 and the tricuspid valve 8 for connecting the valve means 52 to the anchoring means 54. In FIG. 13b, the apparatus 42 is arranged such that the valve means 52 is placed in the mitral valve 8. Now, an anchoring means 54 as shown in FIG. 3c is used for engaging the wall of the superior vena cava 2. The connecting means 246 extends from the superior vena cava 2, through the right atrium 6, penetrating the interatrial septum 14 and through the left atrium 26 to the valve means 52 placed in the mitral valve 30. The connecting means 46 may have a pre-programmed shape adapted to its extension between the superior vena cava 2 and the mitral valve 30. Alternatively, the connecting means 46 may be flexible for allowing it to be appropriately shaped and thereafter locked in the appropriate shape.

Figure 13C:
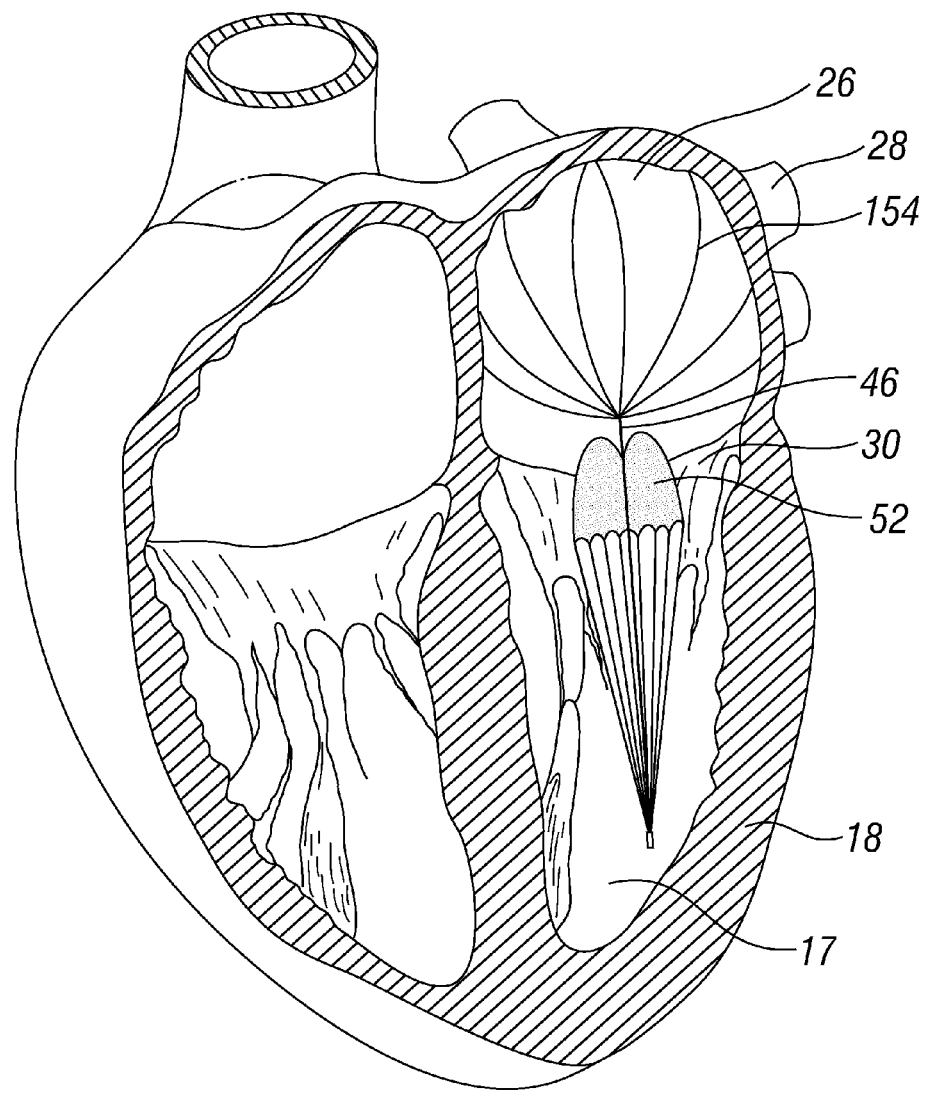
Figure 13D:
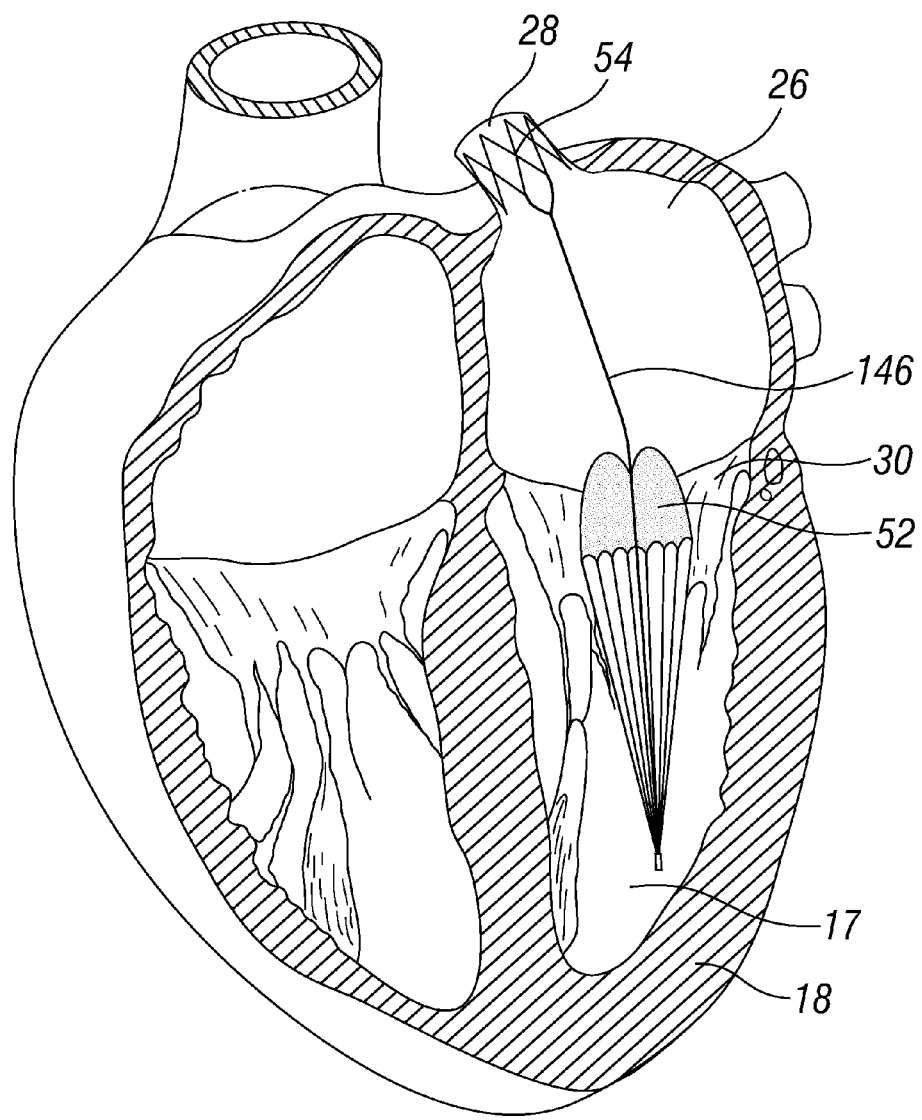

In FIG. 13c, an apparatus 42 as shown in FIG. 3d is used for treating a mitral valve 30. The anchoring means 154 is expanded to contact the inner wall of the left atrium 26 for fixing the position of the apparatus 42, while the valve means 52 is arranged in the mitral valve 30. In FIG. 13d, another way of using the apparatus 42 shown in FIG. 3b is shown. The anchoring means 54 is now arranged to make contact with a vessel wall in a pulmonary vein 28 and the connecting means 46 is arranged extending through the left atrium 26 to the valve means 52 which is arranged in the mitral valve 30.

Figure 13E:
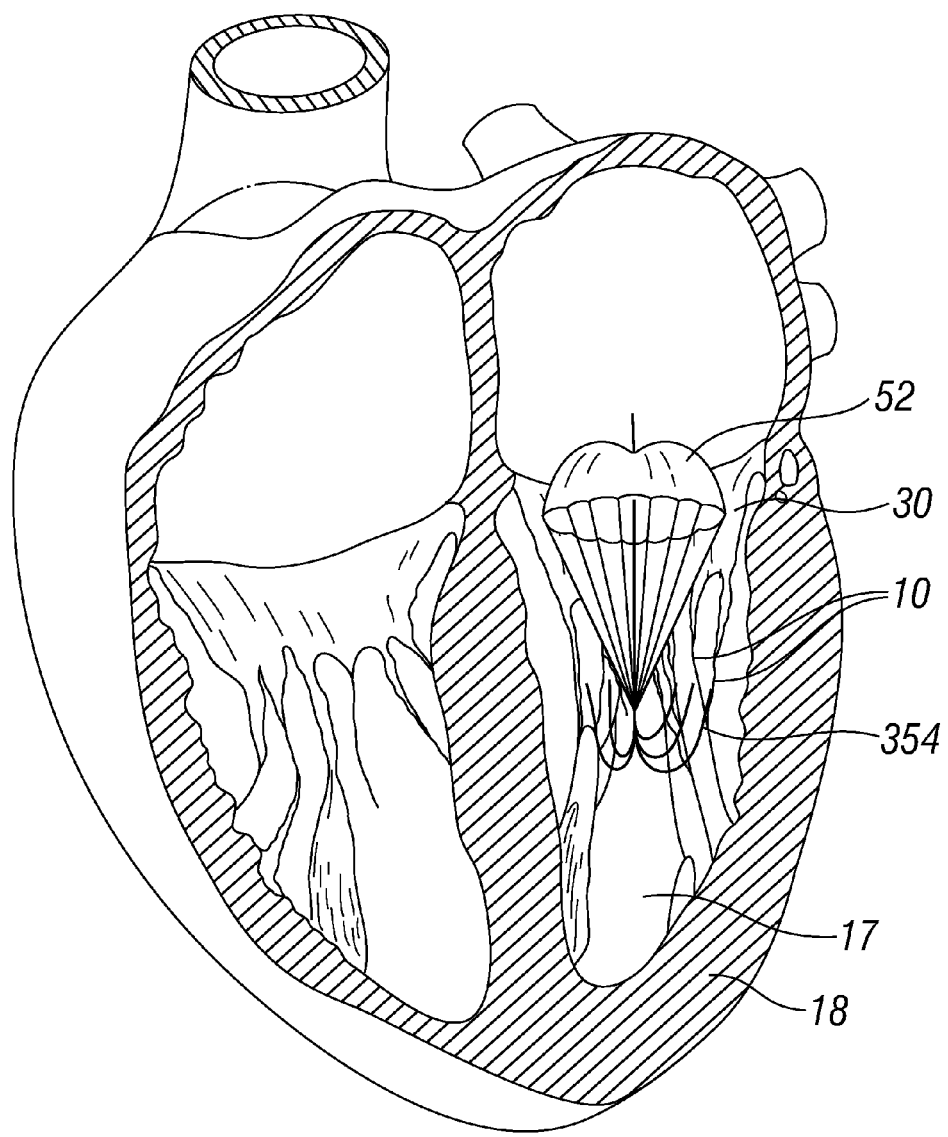
Figure 13F:
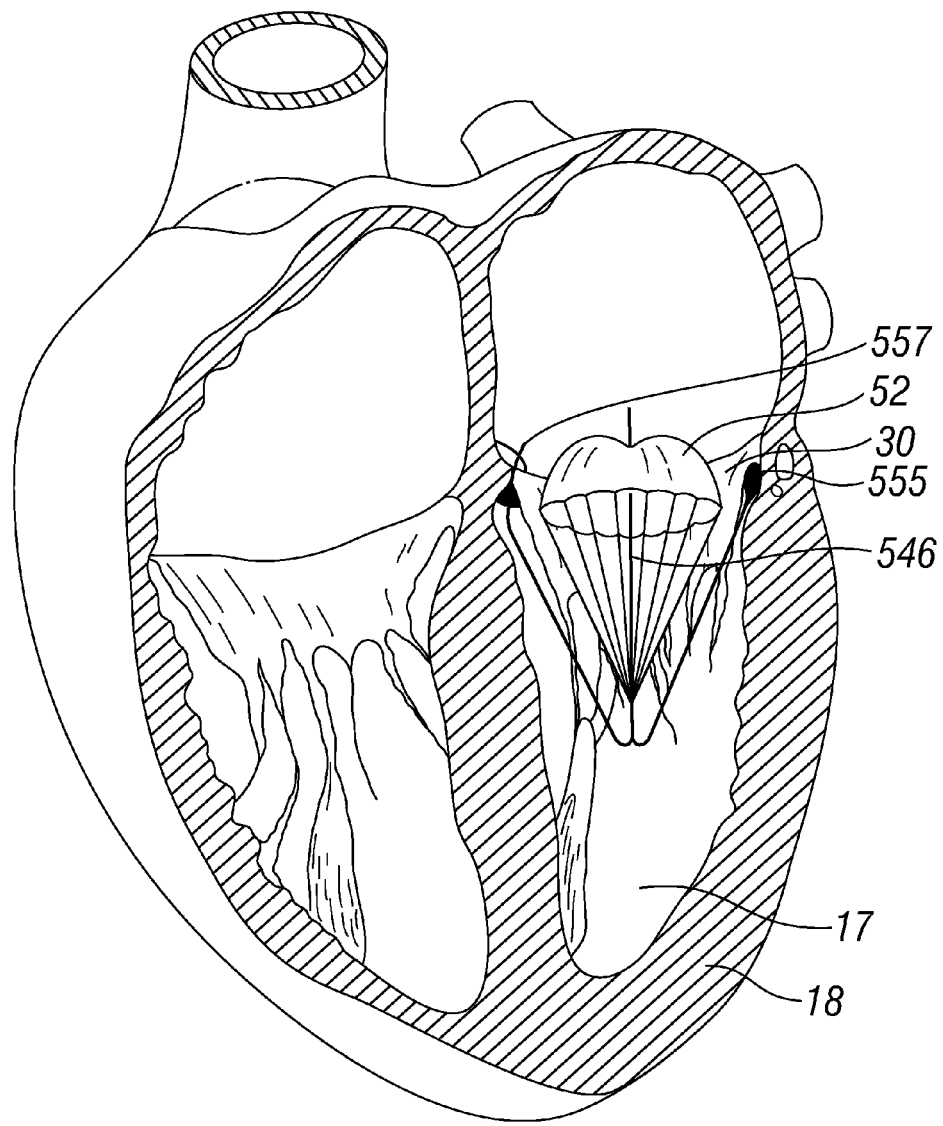
Figure 13G:
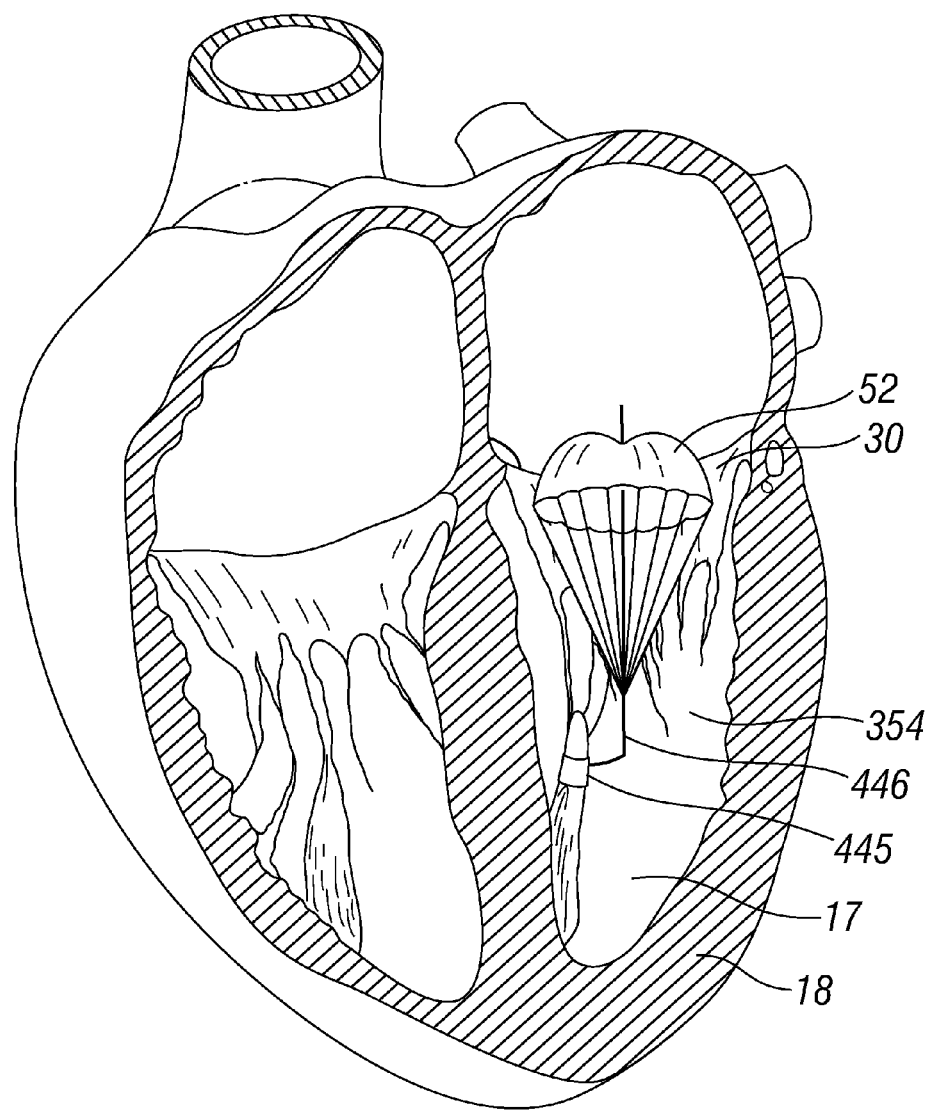
Figure 13H:
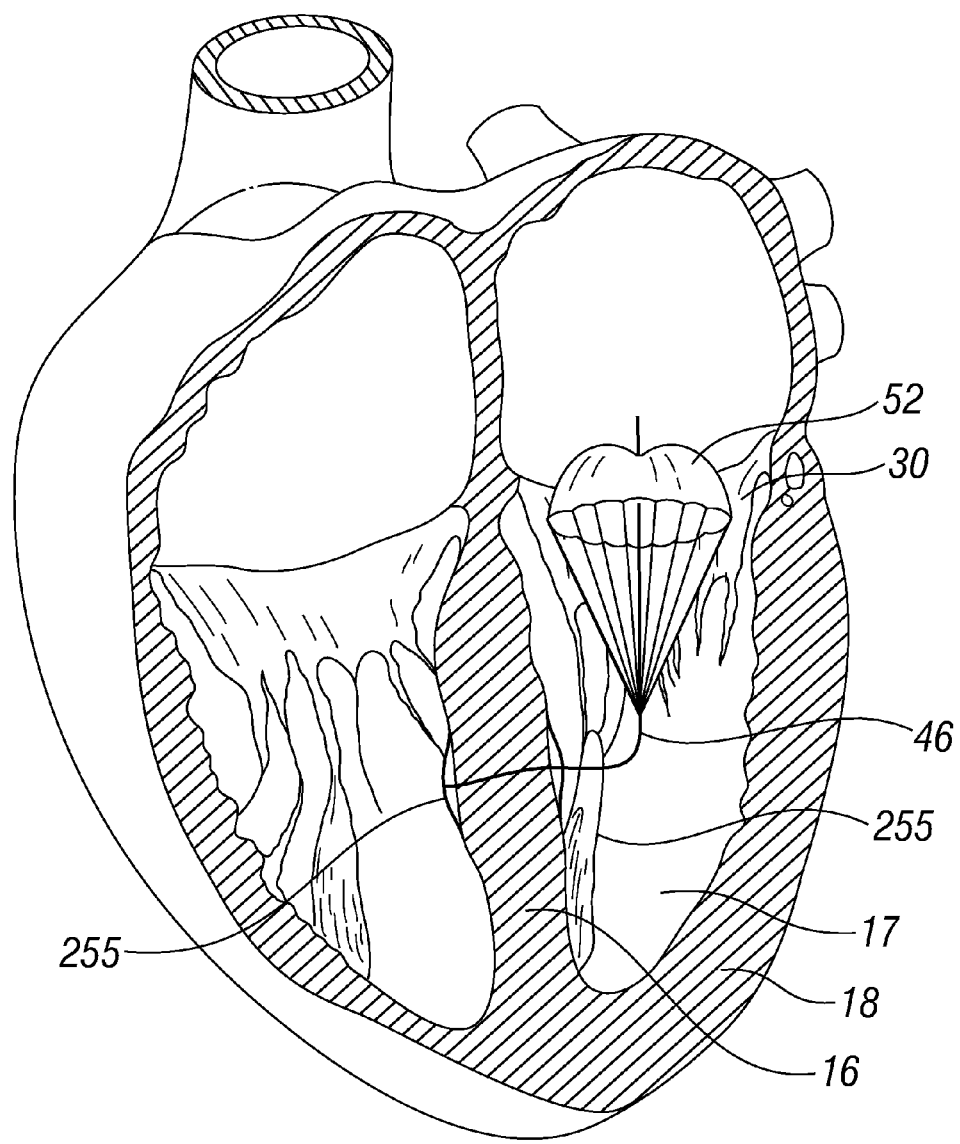
Figure 13I:
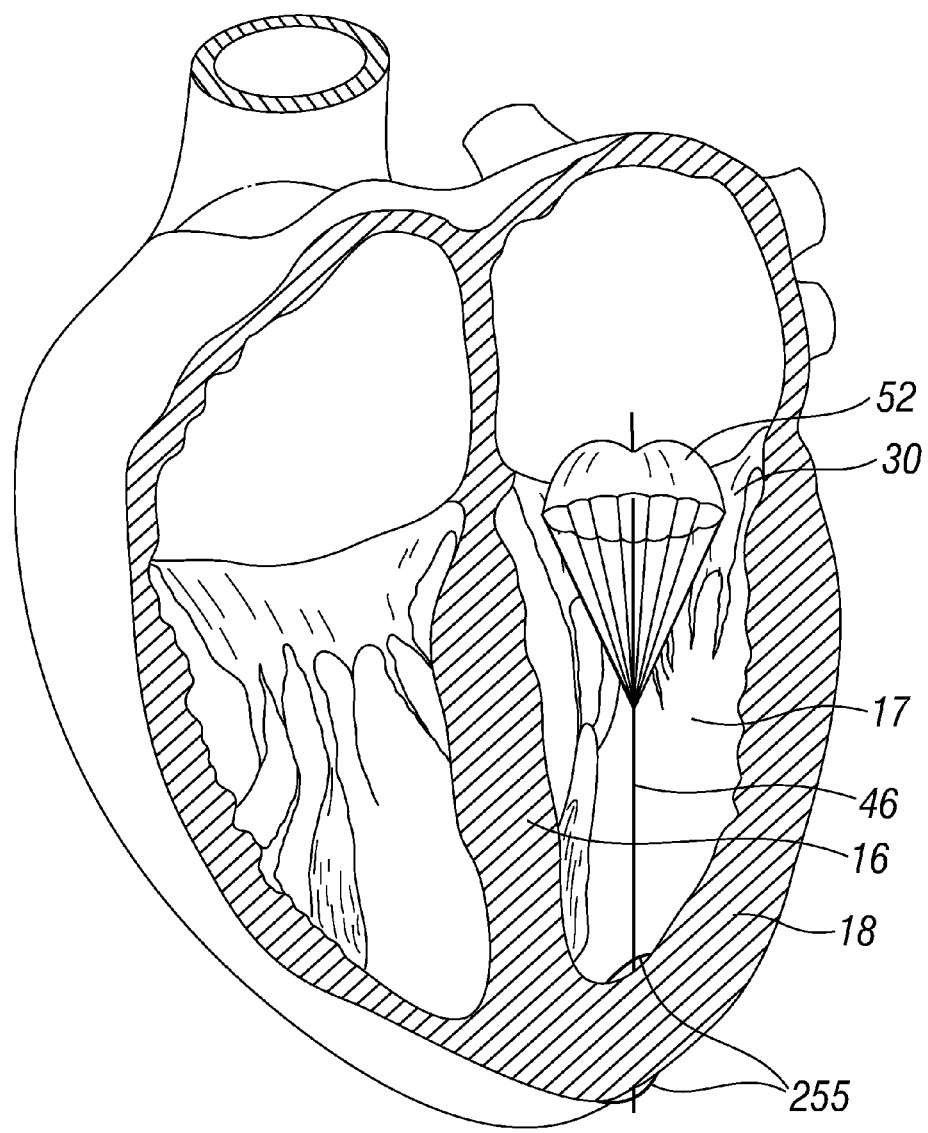

FIGS. 13e-i illustrate different embodiments of the anchoring means 54 for use when the valve means 52 is arranged in the mitral valve 30. It will be appreciated by those skilled in the art that these embodiments may be used instead for placing the valve means 52 in the tricuspid valve 8. In FIG. 13e, an apparatus as shown in FIG. 4b is used. The anchoring means 354 is arranged to engage the chordae tendinae 11 such that the chordae tendinae 11 are captured within the hooks 355 of the anchoring means 354 for fixing the position of the apparatus 42. In FIG. 13f, an apparatus as shown in FIG. 4d is used. The anchoring means 554 is arranged to engage the mitral valve annulus. The anchoring means 554 is shown penetrating the valve annulus with disk-shaped elements 555 engaging opposite sides of the valve annulus for fixing the position of the apparatus 42. Further, another disk-shaped element 555 is arranged in contact with a ventricular side of the valve annulus for stabilizing the apparatus 42 within the left ventricle 17. In FIG. 13g, an apparatus 42 as shown in FIG. 4c is used. The anchoring means 454 has clips 455 which are arranged engaging the papillary muscles 13 for fixing the position of the apparatus 42. In FIGS. 13h and 13i, an apparatus 42 as outlined in FIG. 4a is used. The anchoring means 254 has a disk-shaped element 255 which is arranged in contact with a tissue wall. The valve means 52 and the anchoring means 254 are arranged on opposite sides of the tissue wall and the connecting means 46 penetrates the tissue wall. The anchoring means 254 in contact with the tissue wall therefore fixes the position of the apparatus 42. However, in FIGS. 13h and 13i, the anchoring means 254 comprises another disk-shaped element 255 such that the disk-shaped elements 255 engage opposite sides of the tissue wall for securely fixing the position of the apparatus 42. In FIG. 13h, the anchoring means 254 is arranged to engage the interventricular septum 16 and in FIG. 13i, the anchoring means 254 is arranged to engage the left ventricle muscle wall 18.

Figure 13J:
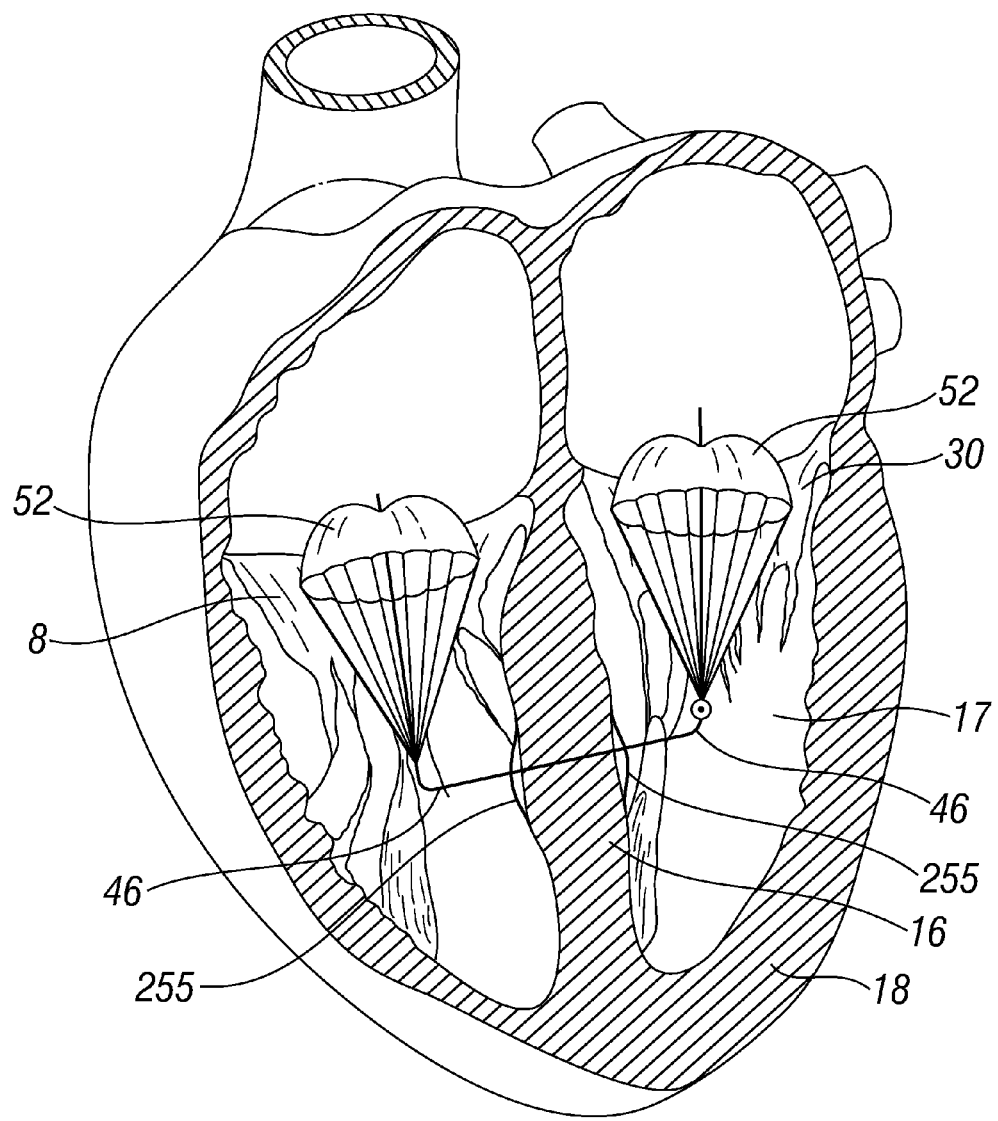
Figure 13K:
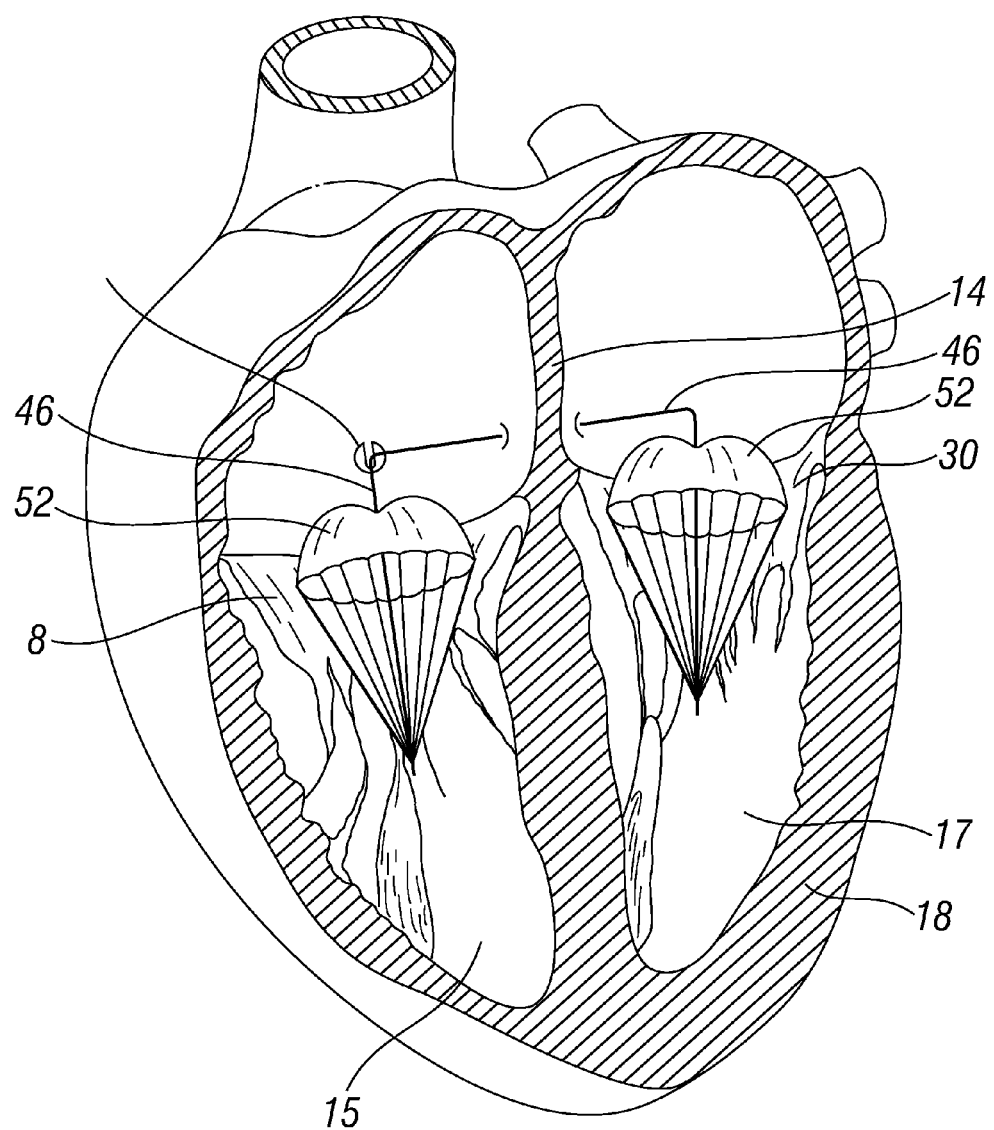

FIGS. 13j and 13k illustrate an apparatus 42 being used for simultaneously treating the mitral valve 30 and the tricuspid valve 8. The apparatus 42 comprises two valve means 52 being positioned in the respective native valves. The apparatus 42 comprises a connecting means 46 connecting the two valve means 52. The connecting means 46 is arranged extending between the valves through the interventricular septum 16 (as shown in FIG. 13j) or the interatrial septum 14 (as shown in FIG. 13k), respectively. Further, the apparatus 42 comprises anchoring means 254 having disk-shaped elements 255 which are arranged on opposite sides of the interventricular septum 16 or interatrial septum 14, respectively, in order to engage tissue and fix the position of the apparatus 42.

Figure 14C:
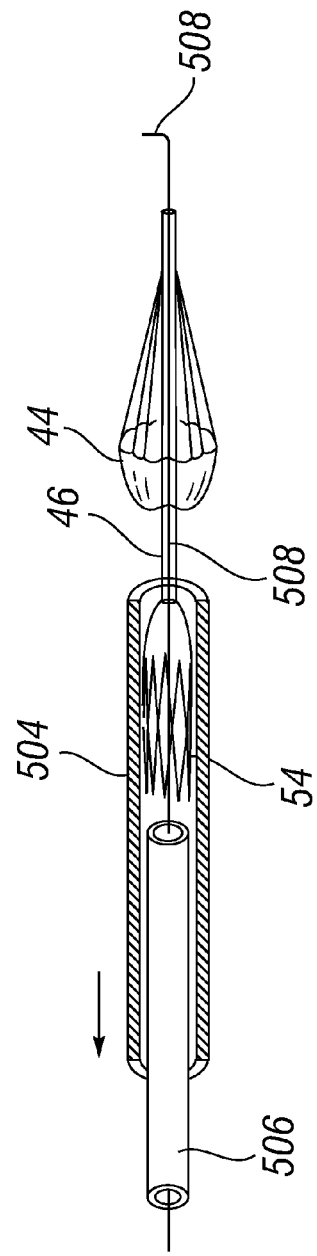

Referring now to FIGS. 14a-h, a delivery system 500 for inserting the apparatus 42 into a patient will be described. As shown in FIG. 14a, the delivery system 500 comprises a guide wire 508, which is first introduced into the patient extending to the position where the apparatus 42 is to be placed. The guide wire 508 thereafter provides a guiding path to the desired position within the patient. The delivery system 500 further comprises a delivery catheter 502, which is the outermost part of the delivery system 500 within the vascular system of the patient. For the sake of clarity, the delivery catheter 502 is not shown in the following figures of the delivery system 500. The apparatus 42 is guided to the position inside the delivery catheter 502. The delivery system 500 further comprises a restraining catheter 504. This catheter 504 keeps the apparatus 42 in a compressed state during delivery. The delivery system 500 further comprises an hula tube 506 which is arranged to slide on the guide wire to the desired position and push the apparatus 42 in front of it.

Figure 14D:
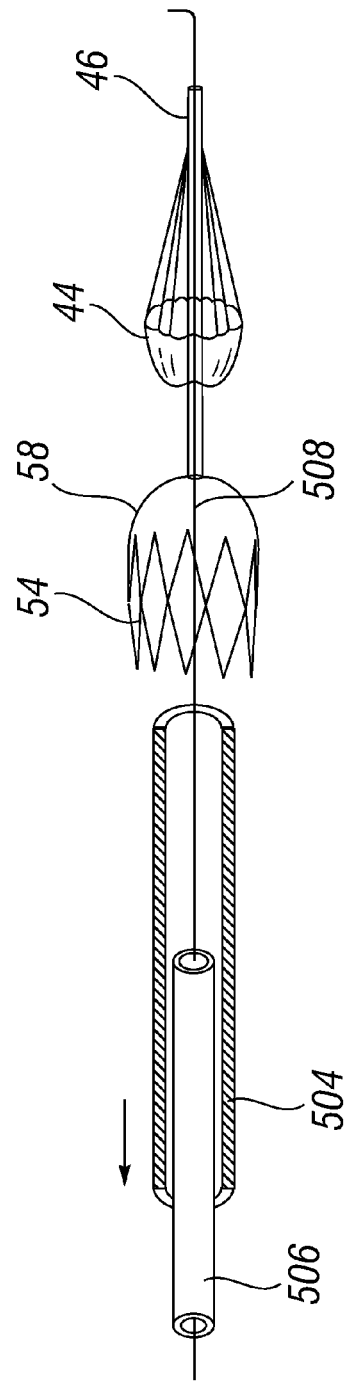

Referring to FIGS. 14b-d, deployment of an apparatus 42 will be indicated. In FIG. 14b, the entire apparatus 42 is inside the restraining catheter 504. The valve means 52 is arranged distal to the anchoring means 54 in the restraining catheter 504, that is the valve means 52 is introduced into the patient in front of the anchoring means 54. The restraining catheter 504 is retracted to release the restrain on the valve means 52, as shown in FIG. 14c. Thus, the valve means 52 is expanded, while the anchoring means 54 is kept in a compressed state. The restraining catheter 504 is then further retracted, releasing the anchoring means 54, as shown in FIG. 14d. Now, the entire apparatus 42 is deployed.

Figure 14G:
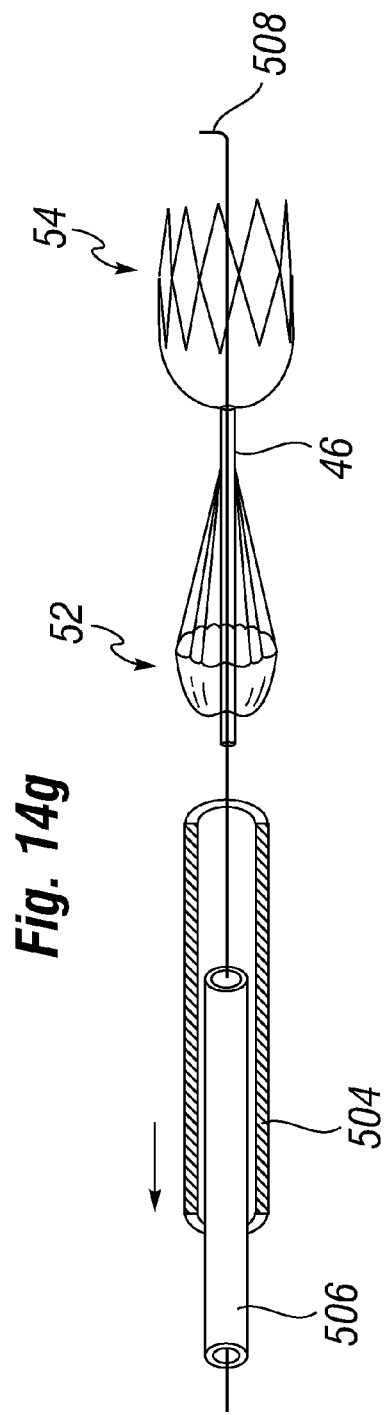

Referring to FIGS. 14e-g, another deployment of an apparatus 42 will be described. In FIG. 14e, the entire apparatus 42 is inside the restraining catheter 504. Now, the valve means 54 is arranged distal to the anchoring means 52 in the restraining catheter 504. Again, the restraining catheter 504 is retracted to release the restrain on the anchoring means 54, as shown in FIG. 14f. Thus, the anchoring means 54 is expanded for fixing the position of the apparatus 42, while the valve means 52 is kept in a compressed state. The restraining catheter 504 is then further retracted, releasing the valve means 52, as shown in FIG. 14g. Now, the entire apparatus 42 is deployed.

Figure 14H:
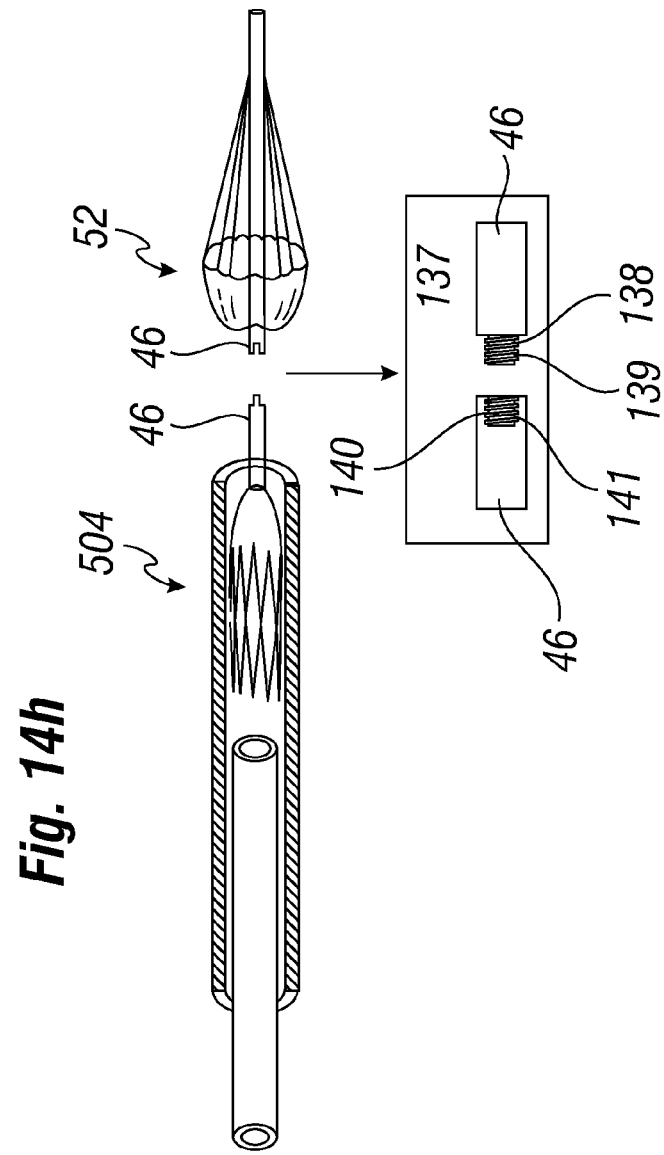

In FIG. 14h, the delivery system 500 is shown in connection to an apparatus 42 having a connecting means 46 with a lock 137 for providing a possibility to detach the valve means 52 from the anchoring means 54. The detachment mechanism can be utilized for storage purposes. When the valve means 52 are made of glutaraldehyde-treated biological tissue, the valve means 52 can be stored in a liquid fluid while the rest of the apparatus 42 and delivery system 500 may be stored under dry conditions. When making ready for use, the valve means 52 that has been stored in liquid may be rinsed and thereafter connected to the anchoring means 54 by attaching the male portion 138 of the lock 137 to the female portion 140 of the lock 137. Thereafter the valve means 52 may be folded and retracted or pushed inside the restraining catheter 504 to make the entire apparatus 42 ready for insertion into a patient.

Referring now to FIGS. 15-20, methods for inserting an apparatus 42 into a patient will be described.

Figure 15A:
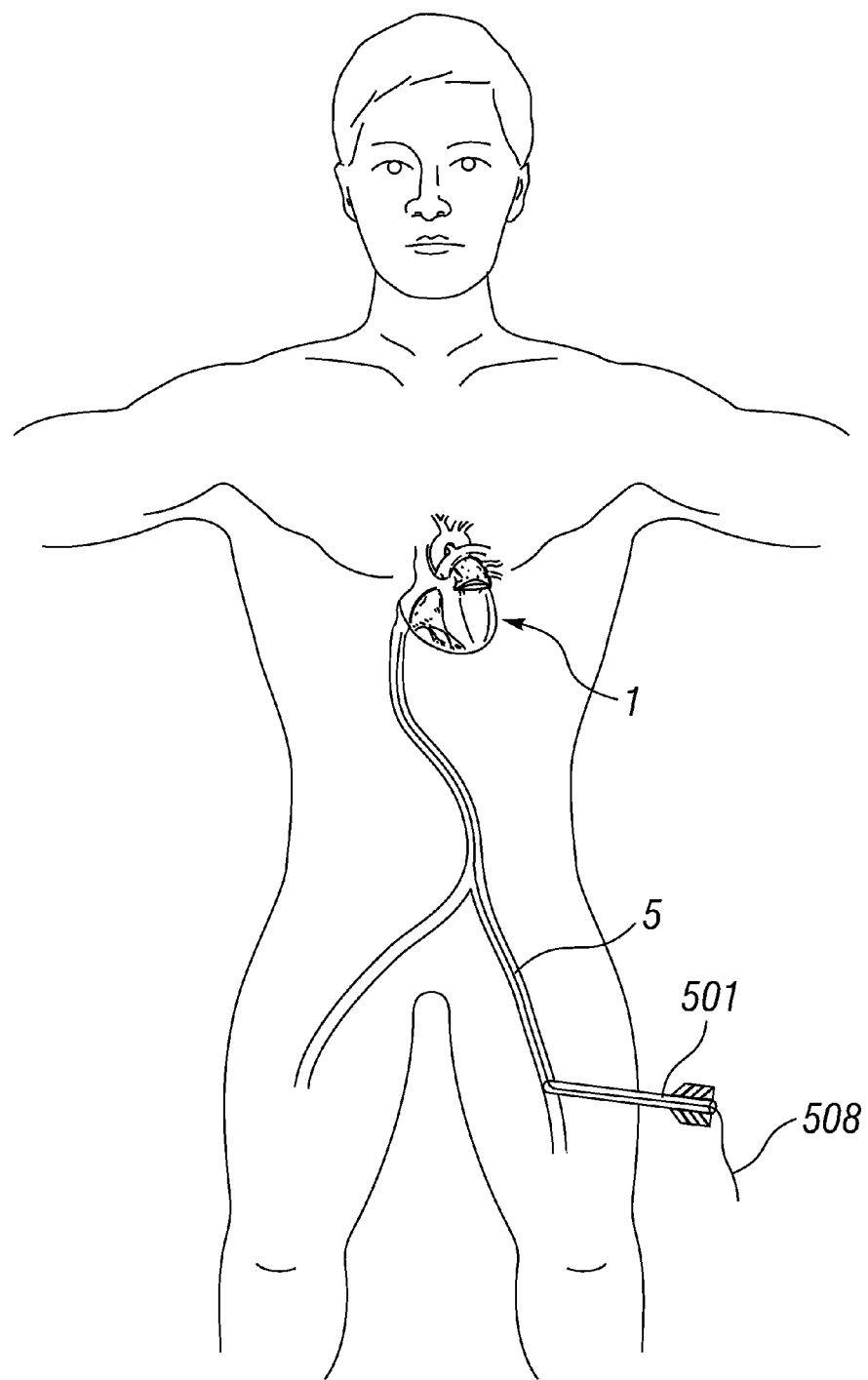
FIGS. 15a-20e are schematic views illustrating methods for inserting the blood flow controlling apparatus into a patient.
Figure 15B:
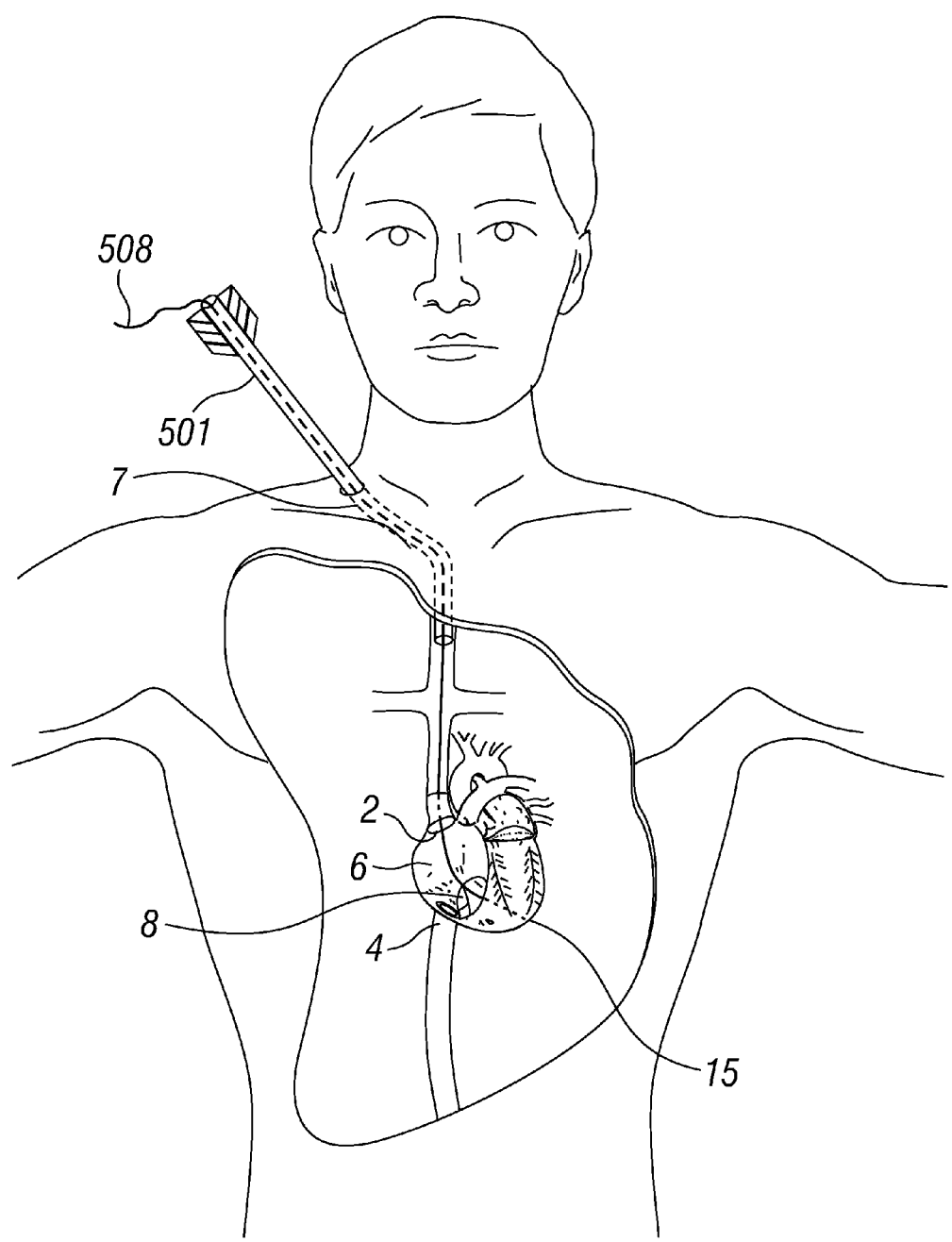
Figure 15C:
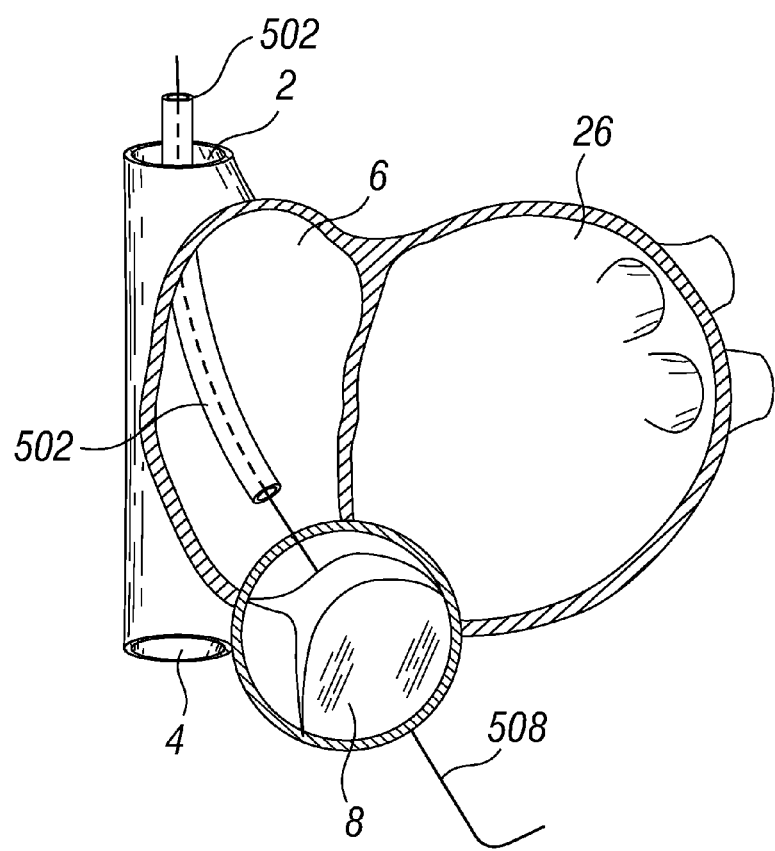
Figure 15D:
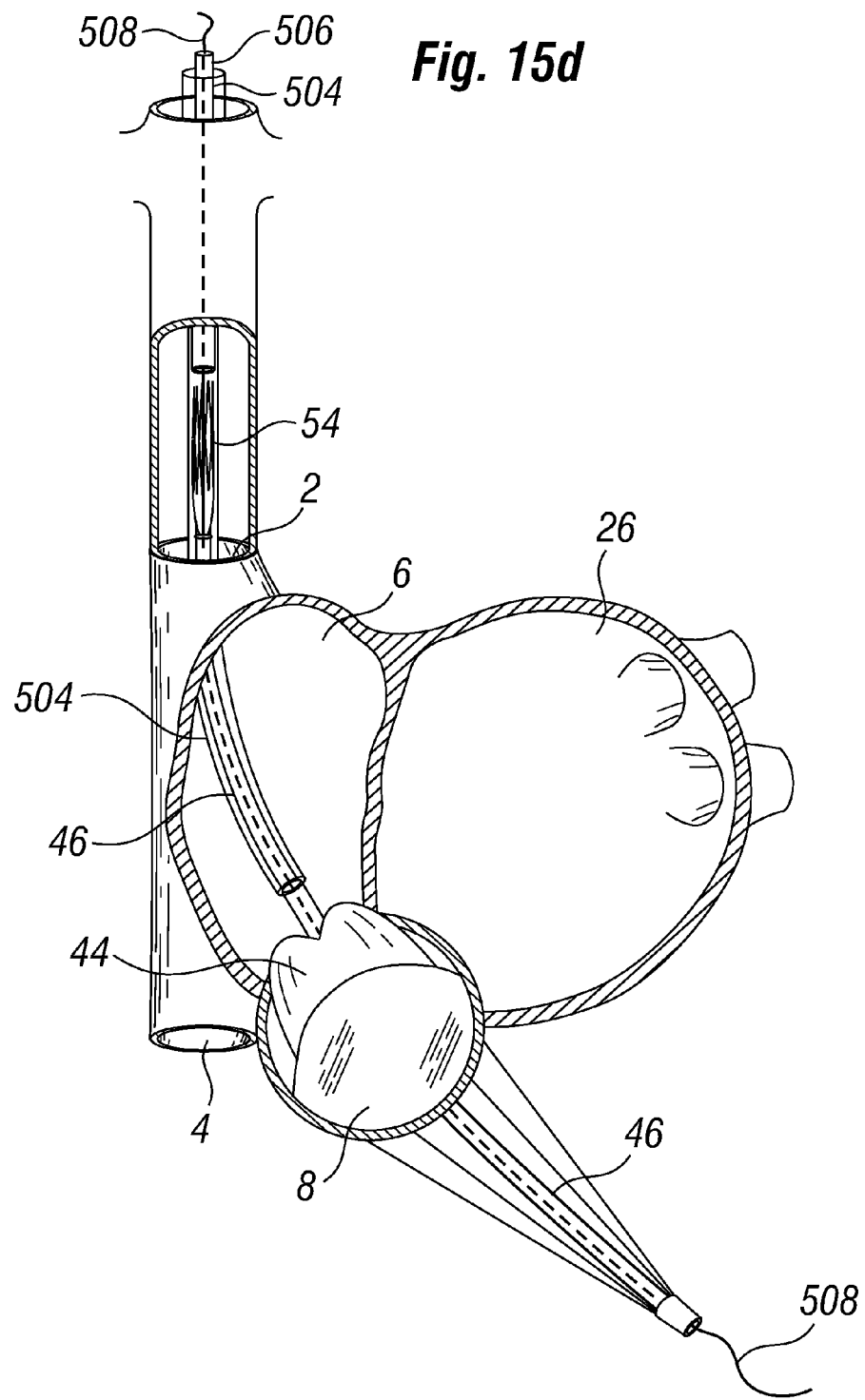
Figure 15E:
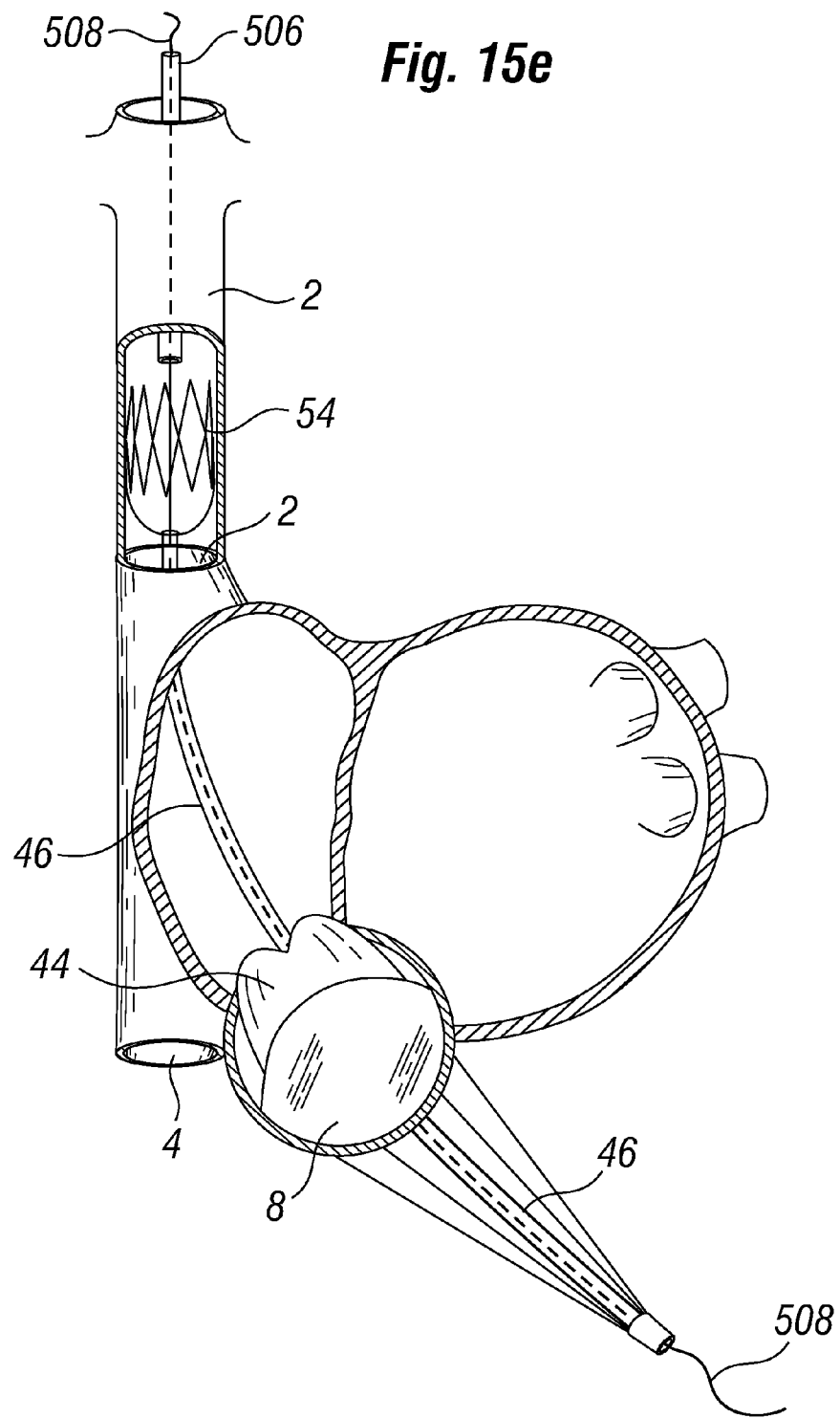

Referring first to FIGS. 15a-e, a method for inserting an apparatus 42 for treatment of the tricuspid valve 8 will be described. In FIG. 15a, a body of a patient is shown, indicating the heart 1 and access to the heart 1 via the vascular system. A puncture is made in the groin of the patient for accessing the femoral vein 5, which leads to the inferior vena cava 4 and further to the right atrium 6 of the heart 1. An introducer sheath 501 of the delivery system 500 is applied in the puncture for providing an access tube into the femoral vein 5. The guide wire 508 of the delivery system 500 is lead into the right atrium 6 for providing guidance of the apparatus 42 to the desired position. In FIG. 15b, another access route to the right atrium 6 is indicated. A puncture is made in the neck of the patient for accessing the internal jugular vein 7 of the patient. The guide wire 508 is lead through the internal jugular vein 7 to the superior vena cava 2 and into the right atrium 6. The guide wire 508 is further introduced extending through the tricuspid valve 8 into the right ventricle 15. As shown in FIG. 15c, the delivery catheter 502 is now introduced extending to the orifice of the tricuspid valve 8. For the sake of clarity, the delivery catheter 502 will not be shown in the following FIGS. 15d-e. Now, the restraining catheter 504 and the apparatus 42 is introduced over the guide wire 508 to the tricuspid valve 8. As shown in FIG. 15d, the restraining catheter 504 is retracted so far that the valve means 52 is released inside the orifice of the tricuspid valve 8. The entire delivery system 500 with the apparatus 42 may still be moved in the axial direction to find the optimal position of the valve means 52 in the orifice of the tricuspid valve 8. During this positioning, the effect of the introduced valve means 52 may be controlled simultaneously by means of ultrasound. The restraining means 504 is thereafter withdrawn further and finally from the body, as shown in FIG. 15e. Hereby, the anchoring means 54 is deployed inside the superior vena cava 2 and the apparatus 42 is completely deployed. The apparatus 42 has now been implanted for providing permanent treatment of the tricuspid valve 8. The inner tube 506, the delivery catheter 502 and the guide wire 508 may now also be withdrawn.

Figure 16A:
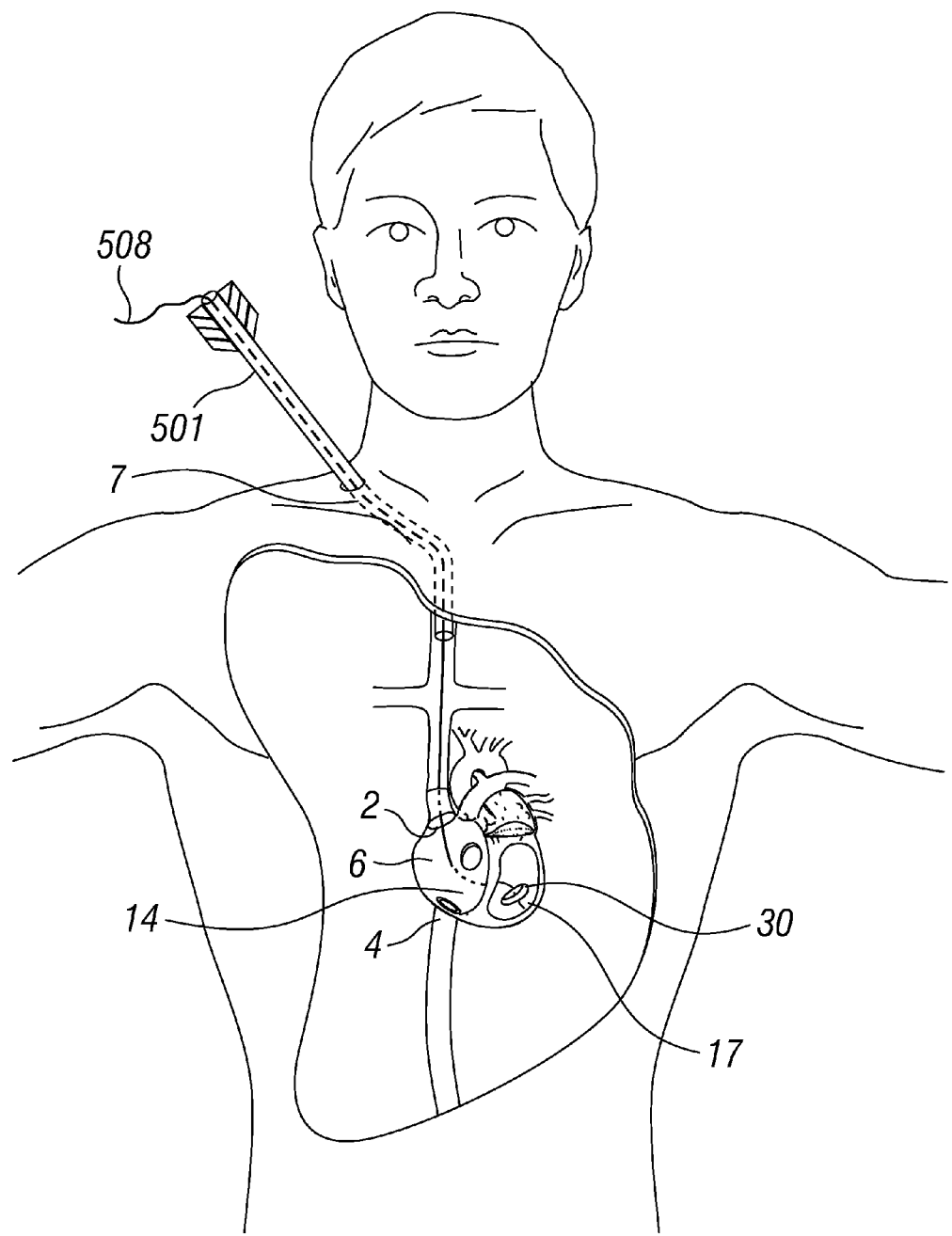
Figure 16B:
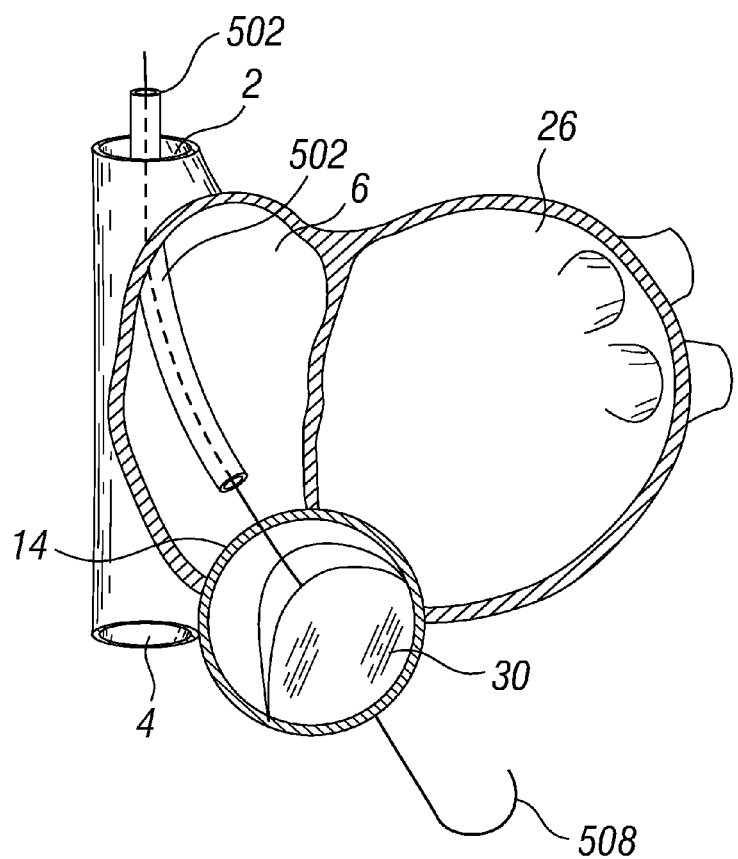
Figure 16C:
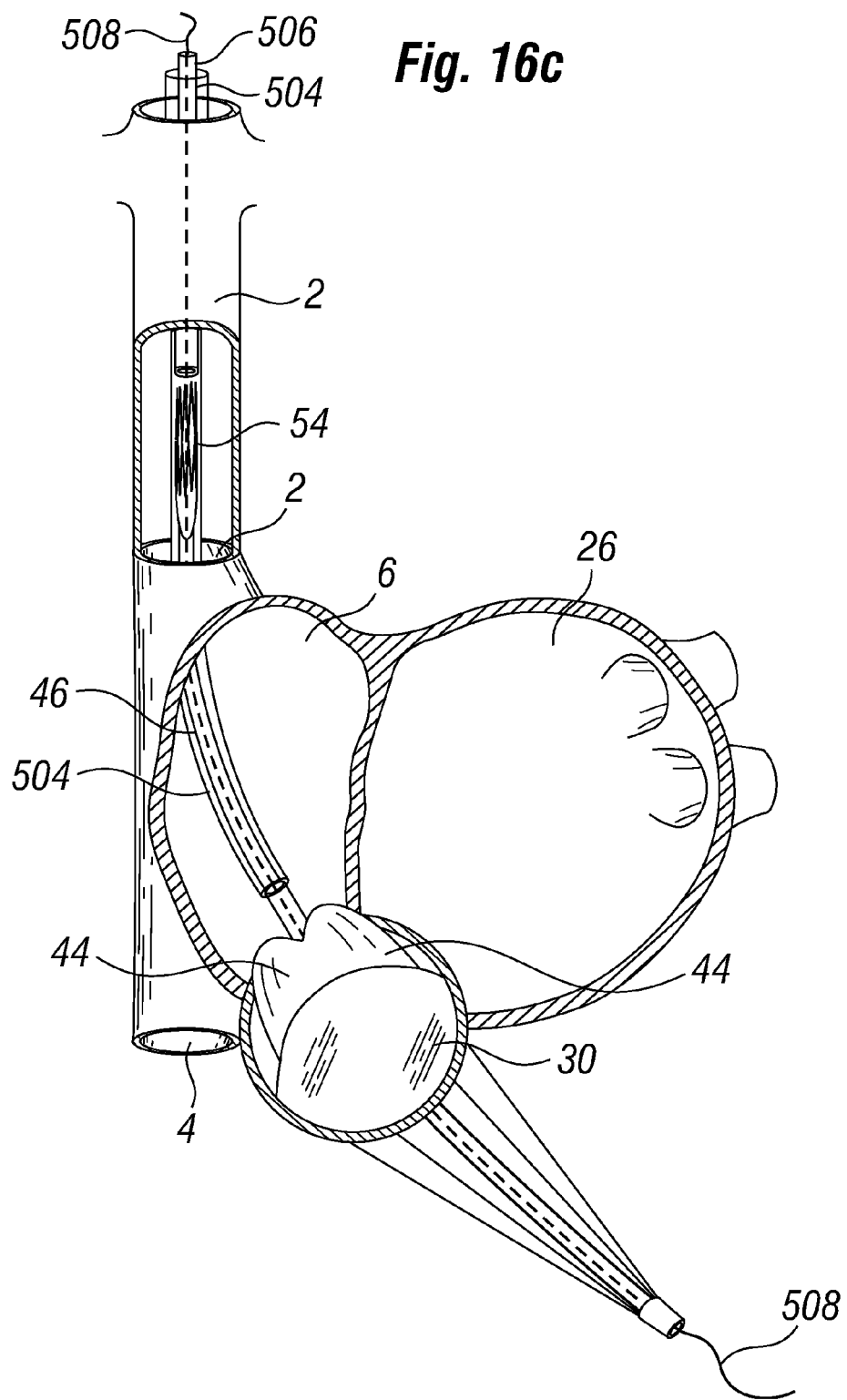
Figure 16D:
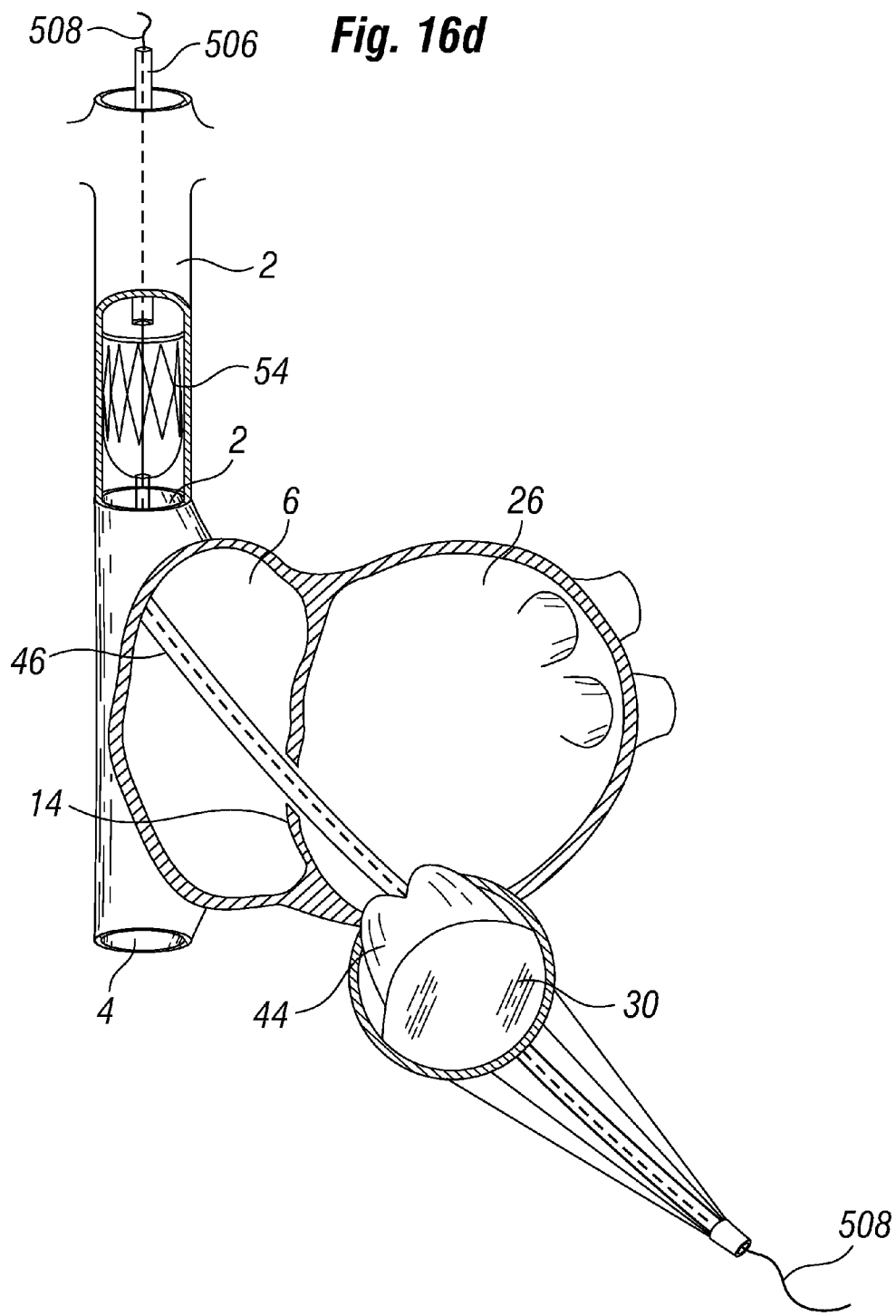

Referring now to FIGS. 16a-d, a method for inserting an apparatus 42 for treatment of the mitral valve 30 will be described. In FIG. 16a, an access route to the left atrium 26 is indicated. A puncture is made in the neck of the patient for accessing the internal jugular vein 7 of the patient. The guide wire 508 is lead through the internal jugular vein 7 to the superior vena cava 2 and into the right atrium 6. The guide wire 508 is further introduced through the interatrial septum 14 into the left atrium 26 and further through the mitral valve 30 into the left ventricle 17. If the patient has a persistent foramen ovale, the guide wire 508 may instead be lead from the right atrium 6 through the foramen ovale into the left atrium 26. As shown in FIG. 16b, the delivery catheter 502 is thereafter introduced over the guide wire 508 extending to the orifice of the mitral valve 30. Again, the delivery catheter 502 will not be shown in the following FIGS. 16c-d. The restraining catheter 504 with the apparatus 42 is now introduced over the guide wire 508 extending to the mitral valve 30. Thereafter, the restraining catheter 504 is retracted, as shown in FIG. 16c, so that the valve means 52 is released inside the orifice of the mitral valve 30. Again, the entire delivery system 500 with the apparatus 42 may still be moved in the axial direction to find the optimal position of the valve means 52 in the orifice of the mitral valve 30. The restraining catheter 504 is thereafter withdrawn to release the anchoring means 54 and finally withdrawn from the patient. As shown in FIG. 16d, the anchoring means 54 has been deployed inside the superior vena cava 2 and the apparatus 42 is completely deployed.

Figure 17A:
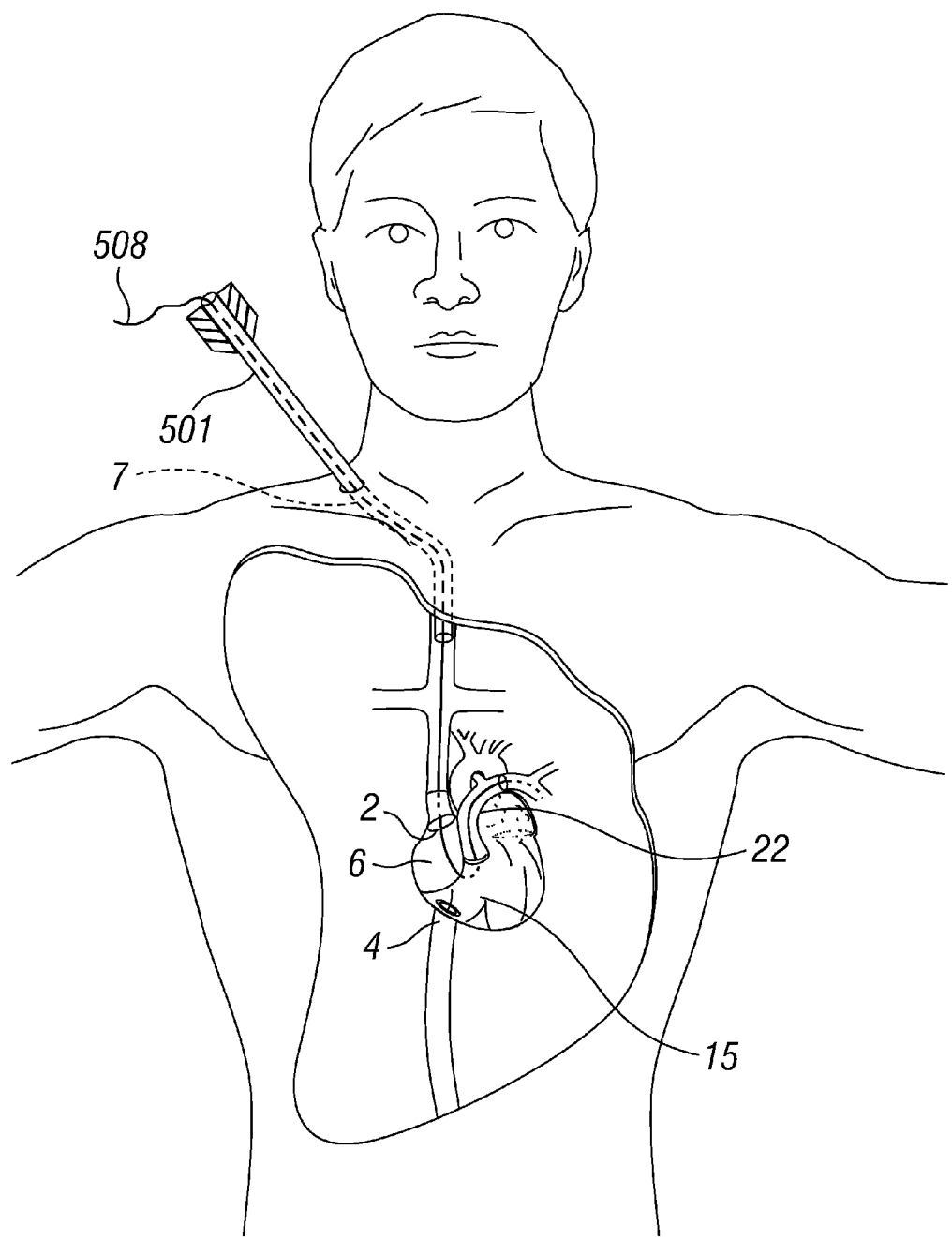
Figure 17B:
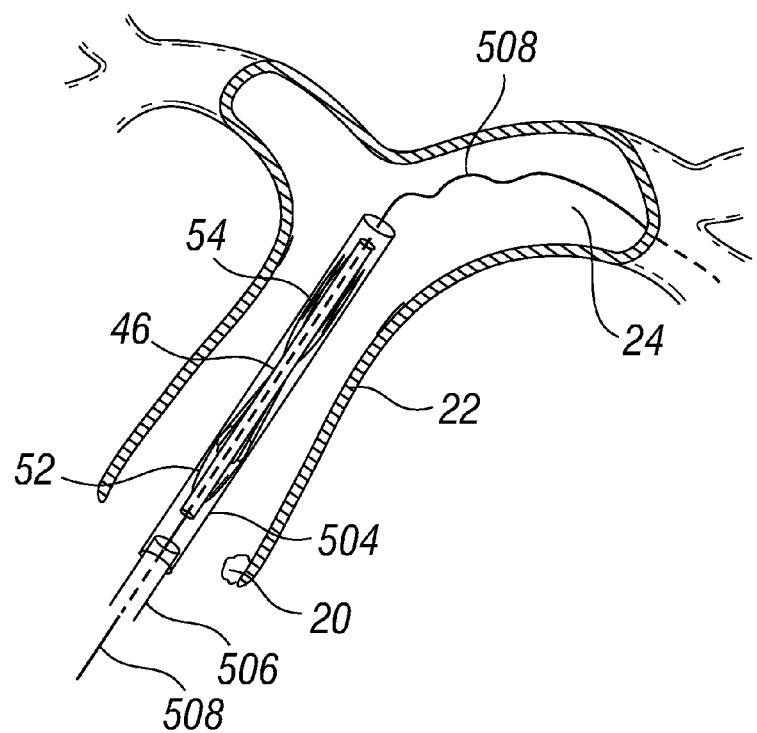
Figure 17C:
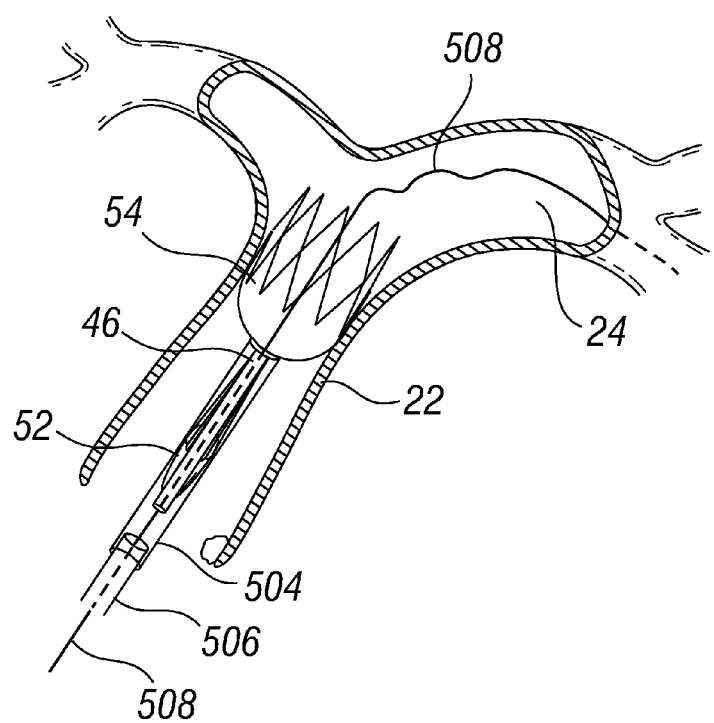
Figure 17D:
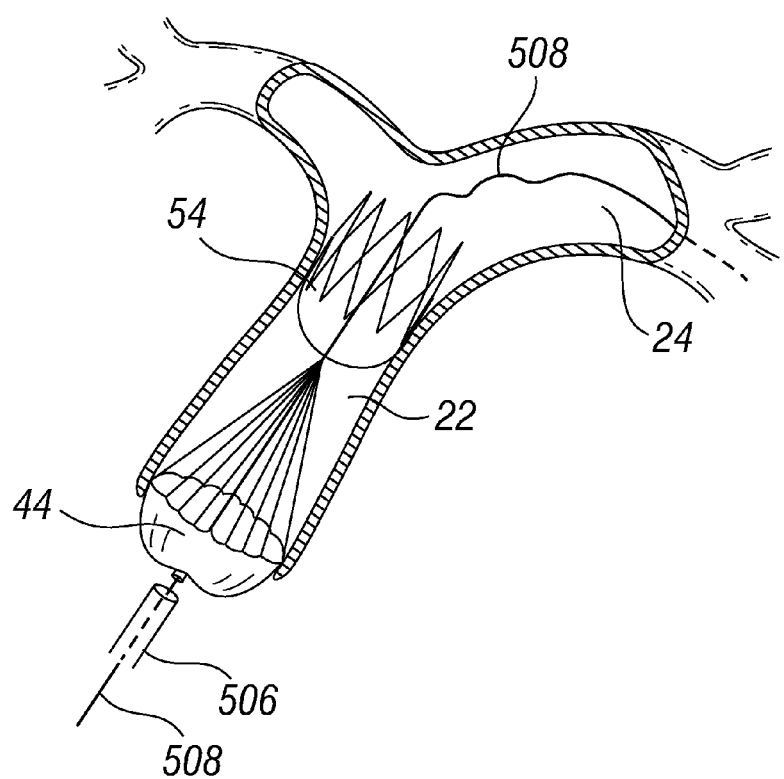

Referring now to FIGS. 17a-d, a method for inserting an apparatus 42 for treatment of the pulmonary valve 20 will be described. In FIG. 17a, an access route to the pulmonary artery 22 is indicated. A puncture is made in the neck of the patient for accessing the internal jugular vein 7 of the patient. The guide wire 508 is lead through the internal jugular vein 7 to the superior vena cava 2 and into the right atrium 6. The guide wire 508 is further introduced through the tricuspid valve 8, the right ventricle 15 and into the pulmonary artery 22. The restraining catheter 504 is introduced over the guide wire 508 and inside the delivery catheter 502 to extend into the pulmonary artery 22, as shown in FIG. 17b. The restraining catheter 504 is retracted, as shown in FIG. 17c, so that the anchoring means 54 is released inside the pulmonary artery 22 for fixing the position of the apparatus 42. The restraining catheter 504 is further retracted and withdrawn from the patient. As shown in FIG. 17d, the valve means 52 is deployed inside the pulmonary artery 22 at the position of the pulmonary valve 20 and the apparatus 42 is completely deployed. The same method may be used in case the anchoring means 54 is arranged on an "inflow" side of the valve means 52, as shown in FIG. 11c, or when a stent 43 is arranged in the pulmonary valve position, as shown in FIG. 11d. In the latter case, the stent 43 is first implanted at the position of the pulmonary valve 20. Thereafter, the apparatus 42 is inserted.

Figure 18A:
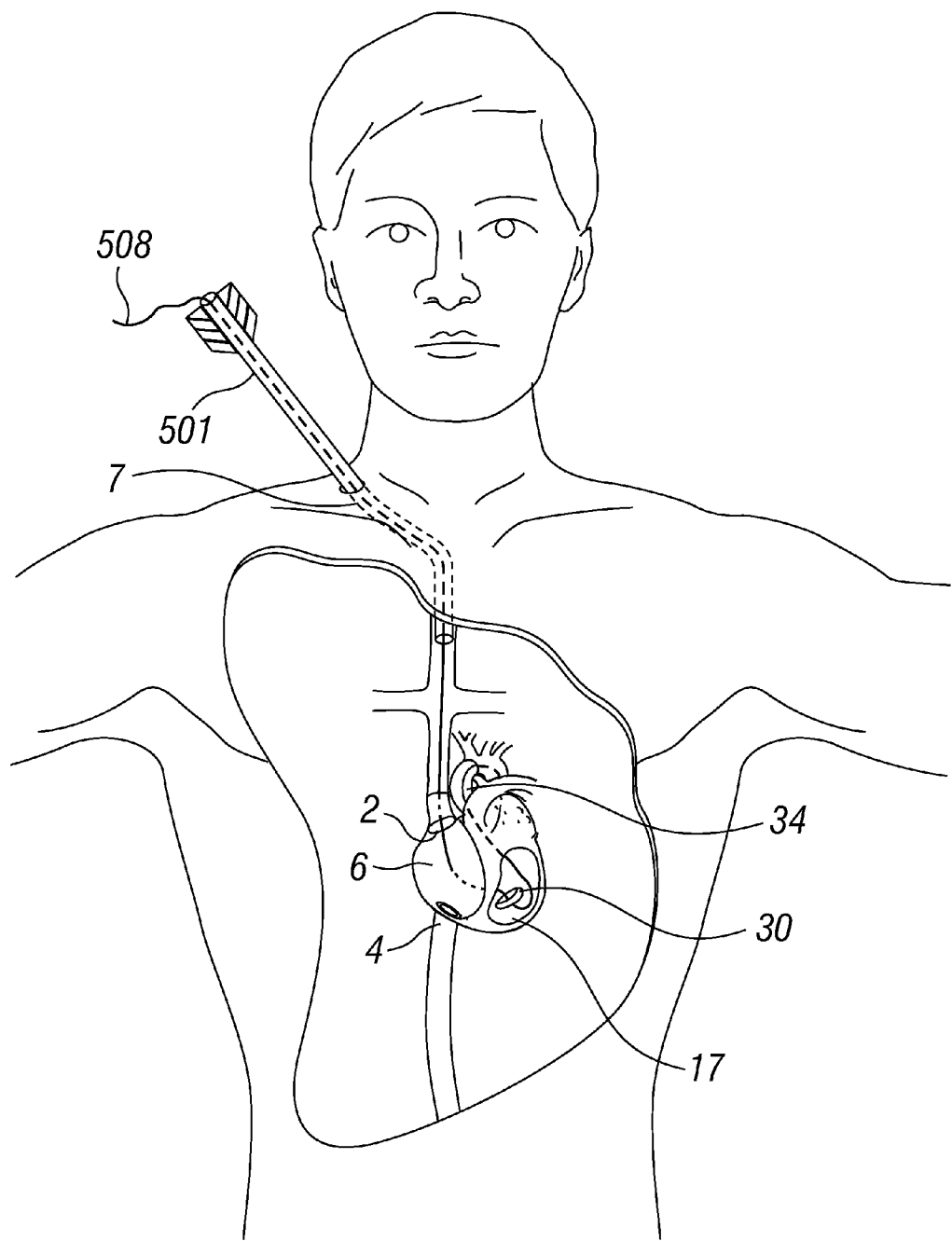
Figure 18B:
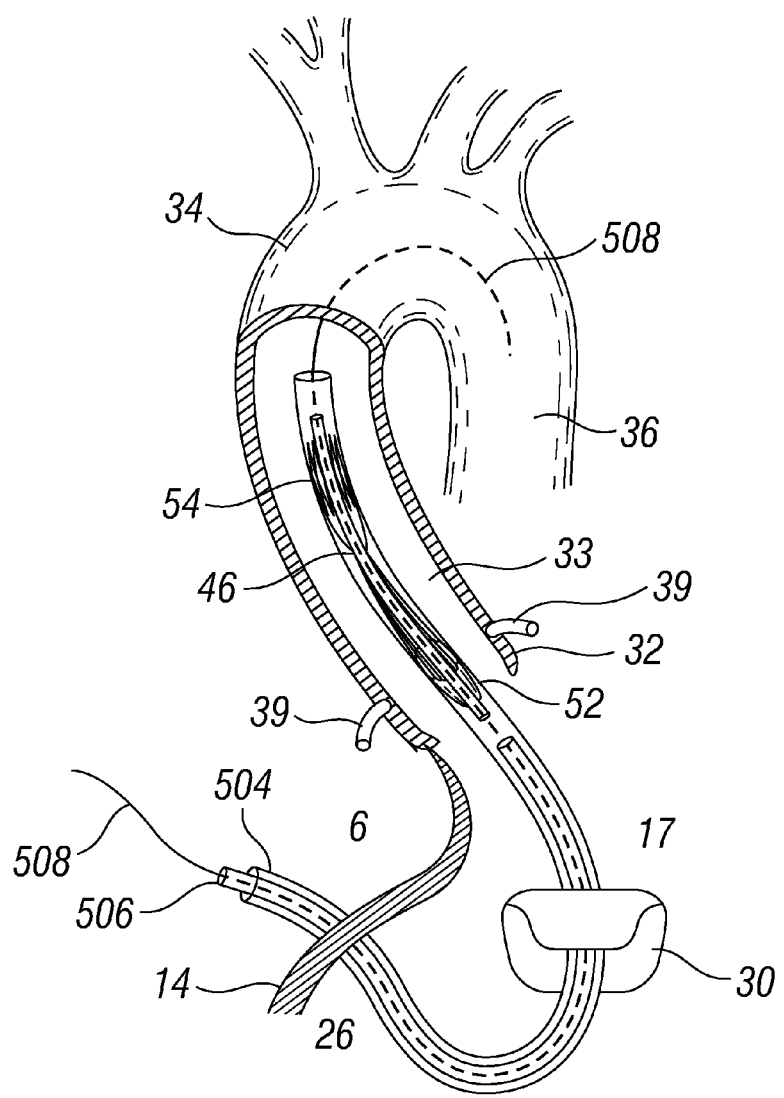
Figure 18C:
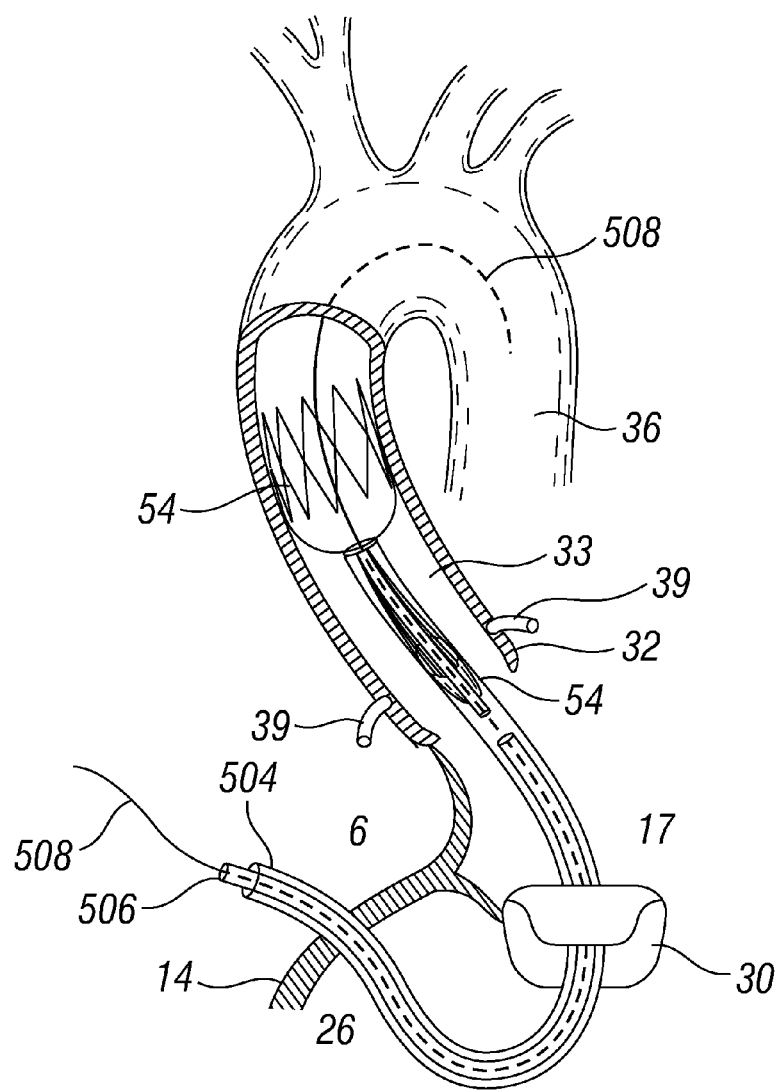
Figure 18D:
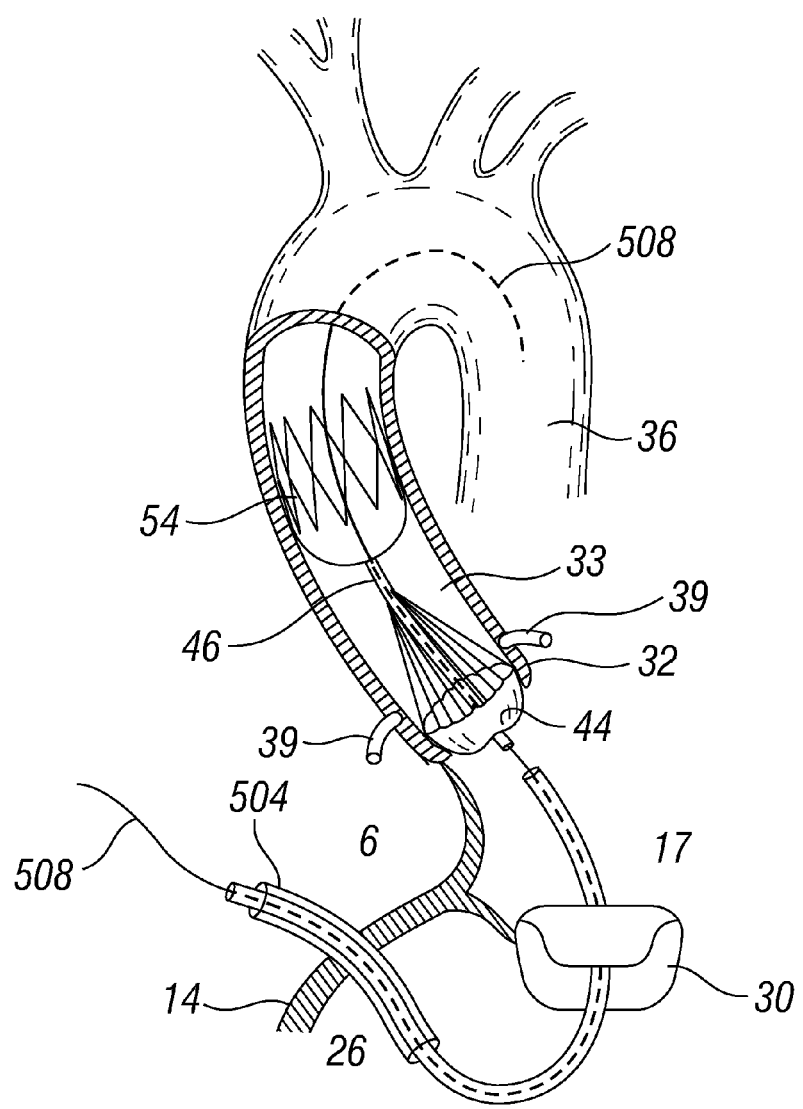

Referring now to FIGS. 18a-d, a method for inserting an apparatus 42 for treatment of the aortic valve 32 will be described. In FIG. 18a, an access route to the aortic valve 32 is indicated. A puncture is made in the neck of the patient for accessing the internal jugular vein 7 of the patient. The guide wire 508 is lead through the internal jugular vein 7 to the superior vena cava 2 and into the right atrium 6. The guide wire 508 is further introduced through the interatrial septum 14 into the left atrium 26, further through the mitral valve 30 into the left ventricle 17, and through the aortic valve 32 into the aorta 34. Alternatively, the route through a persistent foramen ovale might be chosen, as described above with reference to FIG. 16a. The restraining catheter 504 and the apparatus 42 is introduced inside the delivery catheter (not shown) such that the restraining catheter 504 extends into the ascending aorta 33, as shown in FIG. 18b. The valve means 52 is located adjacent to the aortic valve 32 such that the rim 96 of the valve means 52 is located just below the orifices of the coronary arteries 39. Alternatively, the apparatus depicted in FIG. 10b is used, wherein the valve means 52 comprises recesses 97 to fit the orifices of the coronary arteries 39. The restraining catheter 504 is retracted, as shown in FIG. 18c, such that the anchoring means 54 is released inside the ascending aorta 33 for fixing the position of the apparatus 42. The restraining catheter 504 is further retracted and finally withdrawn from the patient. As shown in FIG. 18d, the valve means 52 is deployed inside the aortic ostium and the apparatus 42 is completely deployed.

Figure 19A:
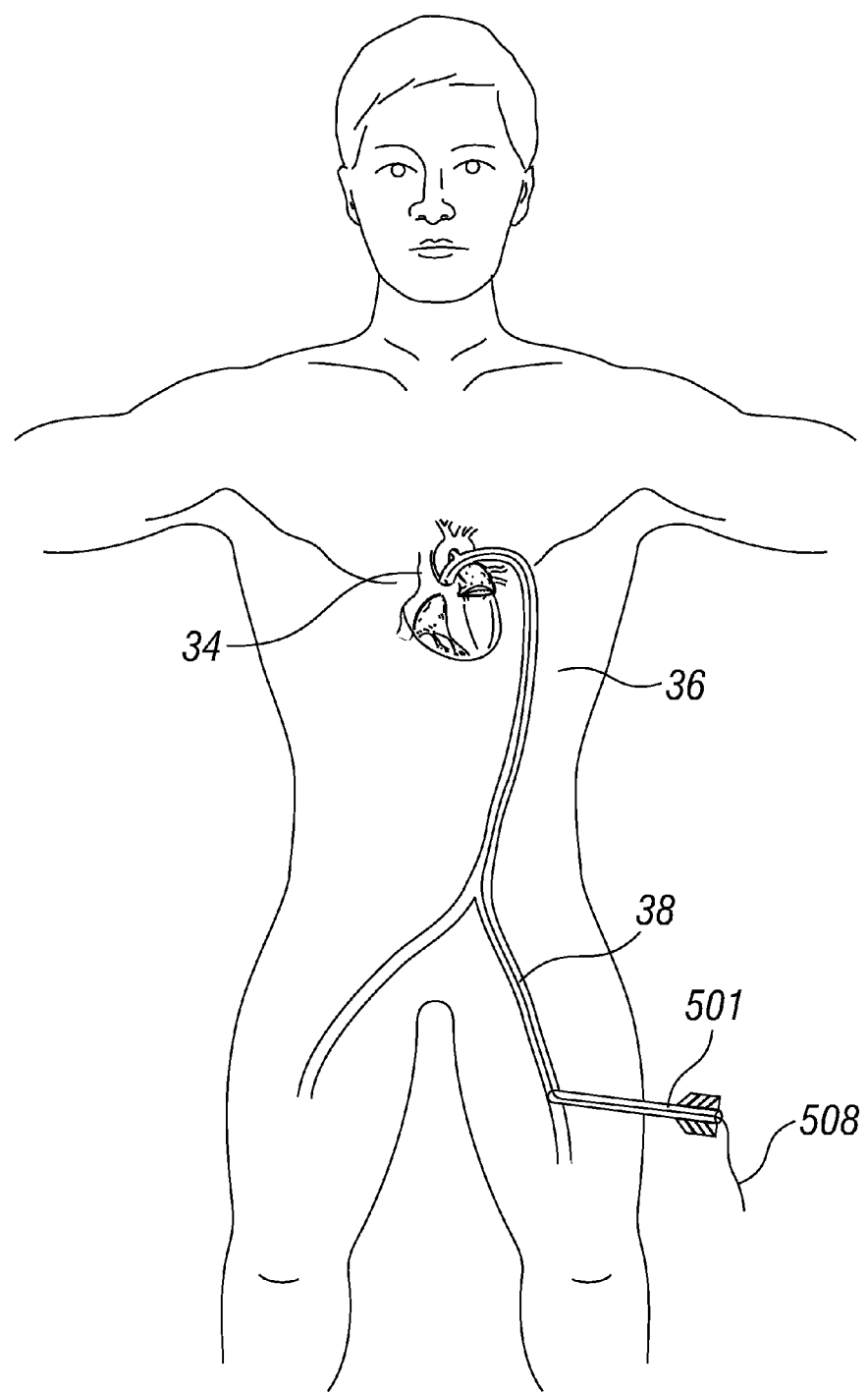
Figure 19B:
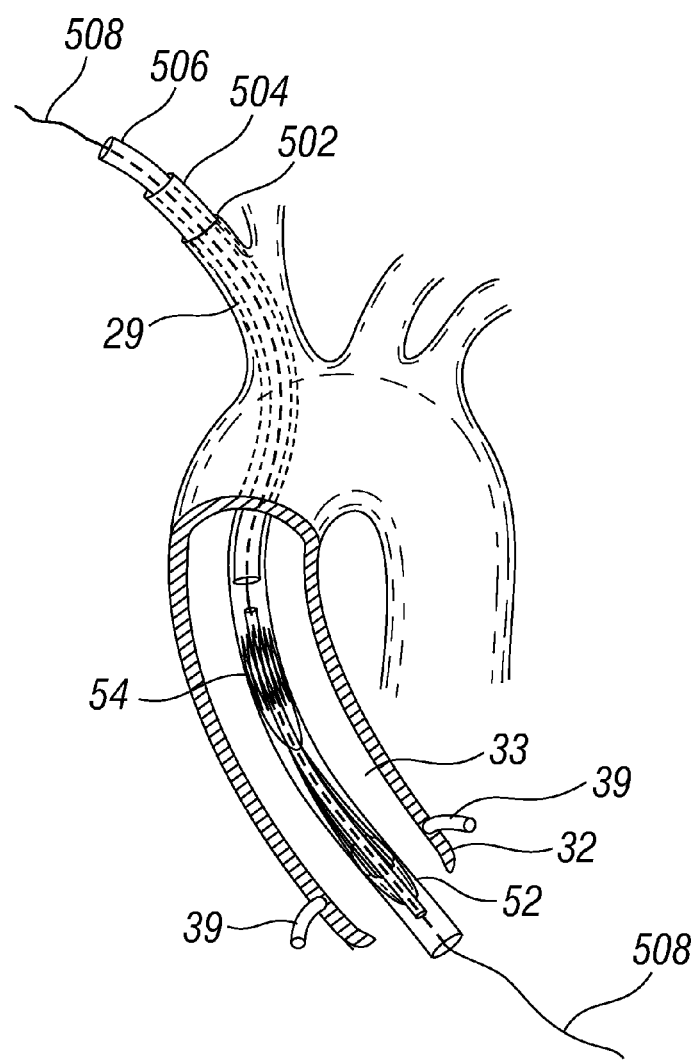
Figure 19C:
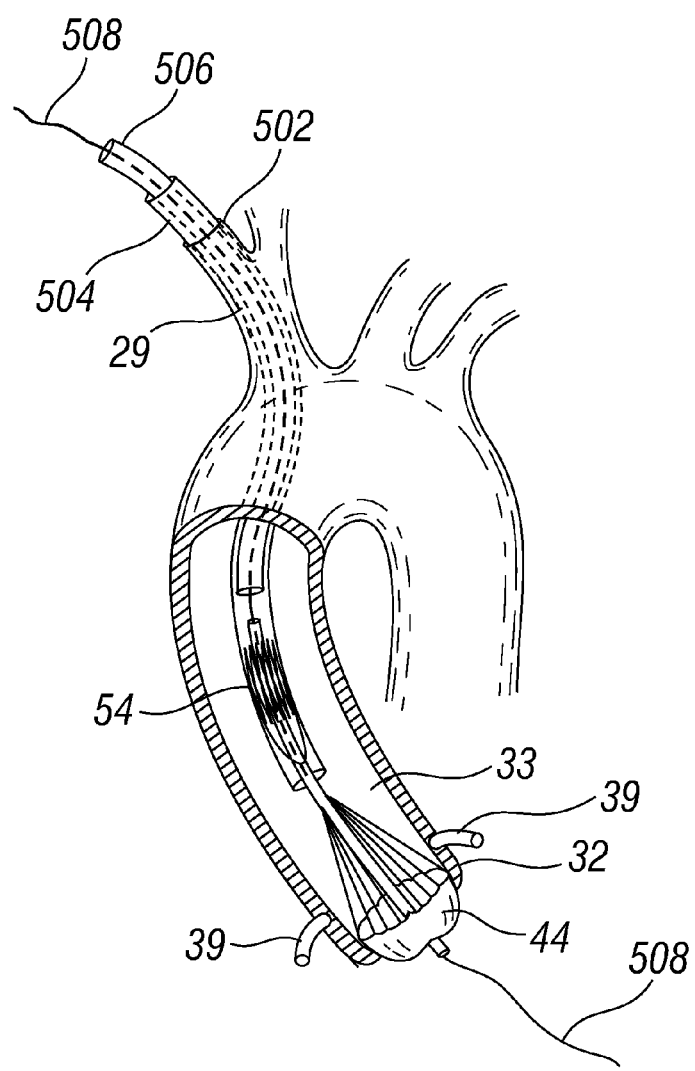
Figure 19D:
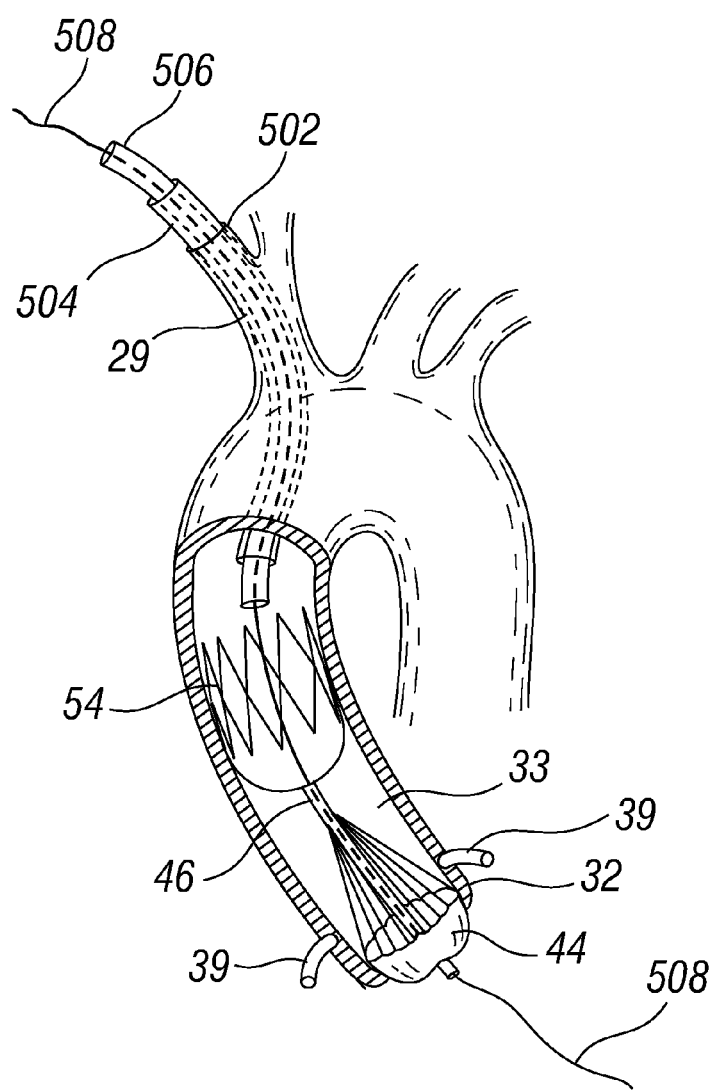

Referring now to FIGS. 19a-d, another method for inserting an apparatus 42 for treatment of the aortic valve 32 will be described. In FIG. 19a, an access route to the aortic valve 32 is indicated. A puncture is made in the groin of the patient to access a femoral artery 38. A guide wire 508 is passed through the femoral artery 38, the descending aorta 36 to the ascending aorta 33 and into the left ventricle 17. Alternatively, other arteries can be used such as the subclavian artery 29. A guide wire 508 is introduced through the arteries to the ascending aorta 33, through the aortic valve 32 and into the left ventricle 17. In FIG. 19b, the guide wire 508 has been introduced through the subclavian artery 29 into the aorta 34. The restraining catheter 504 and the apparatus 42 are introduced inside the delivery catheter (not shown) such that the restraining catheter 504 extends into the ascending aorta 33. The valve means 52 is located adjacent to the aortic valve 32 with the rim 96 of the valve means 52 being located below the orifices of the coronary arteries 39. As shown in FIG. 19c, the restraining catheter 504 is retracted such that the valve means 52 is released inside the aortic valve 32. Again, the entire delivery system 500 with the apparatus 42 may still be moved in the axial direction to find the optimal position of the valve means 52 at the aortic valve 32. The restraining catheter 504 is thereafter withdrawn further and finally from the patient. As shown in FIG. 19d, the anchoring means 54 has been deployed inside the ascending aorta 33 and the apparatus 42 is completely deployed.

Figure 20A:
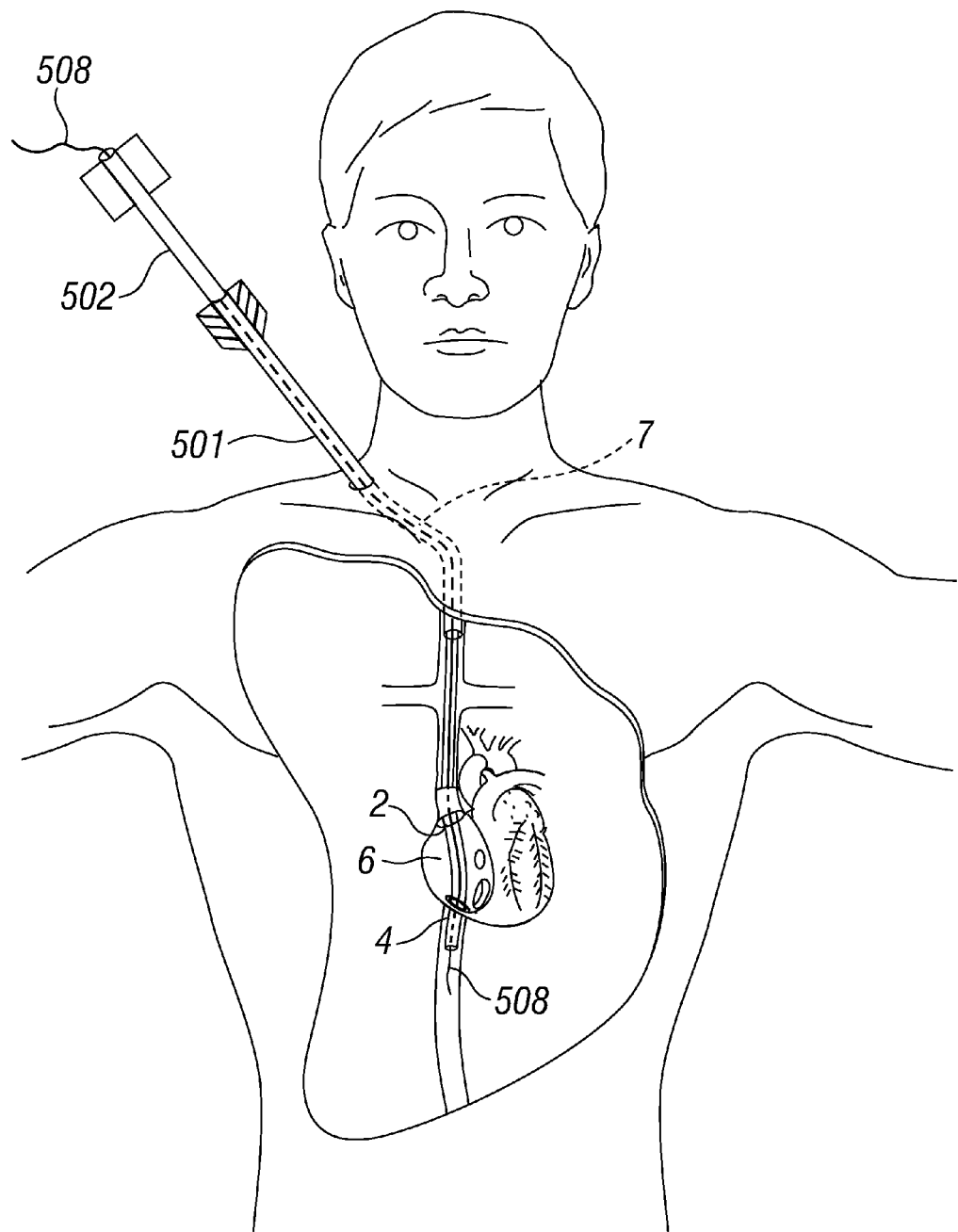
Figure 20B:
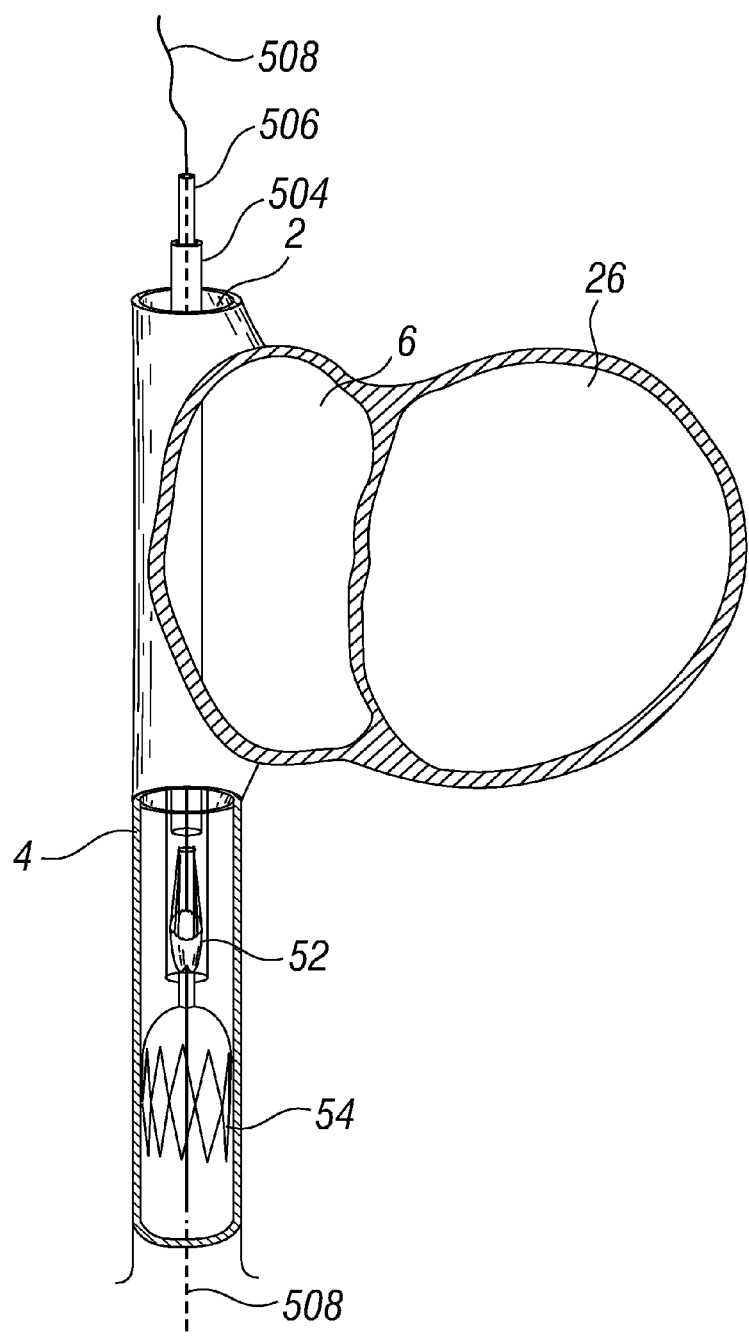
Figure 20C:
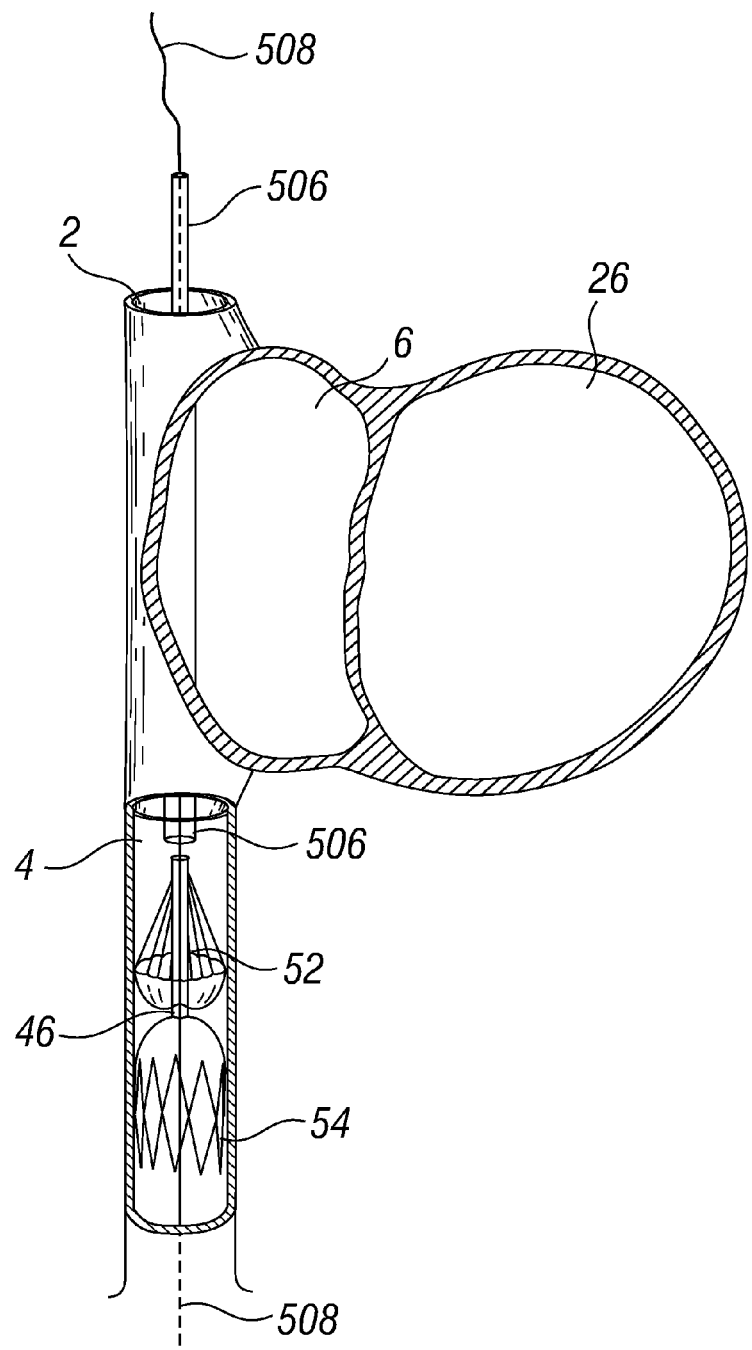

Referring now to FIGS. 20a-e, methods for introducing an apparatus 42 into the inferior vena cava 4 and the superior vena cava 2, respectively, will be described. In FIG. 20a, an access route to the inferior vena cava 4 is indicated. A puncture is made in the neck of the patient to access the internal jugular vein 7. A guide wire 508 is passed through the internal jugular vein 7 into the superior vena cava 2 and the right atrium 6 and further into the inferior vena cava 4. The restraining catheter 504 and the apparatus 42 are introduced inside the delivery catheter (not shown) such that the restraining catheter 504 extends into the inferior vena cava 4. As shown in FIG. 20b, the restraining catheter 504 is retracted such that the anchoring means 54 is released inside the inferior vena cava 4 for fixing the position of the apparatus 42. The restraining catheter 504 is thereafter withdrawn further and finally from the patient. As shown in FIG. 20c, the valve means 52 has been deployed inside the inferior vena cava 4 and the apparatus 42 is completely deployed.

Figure 20D:
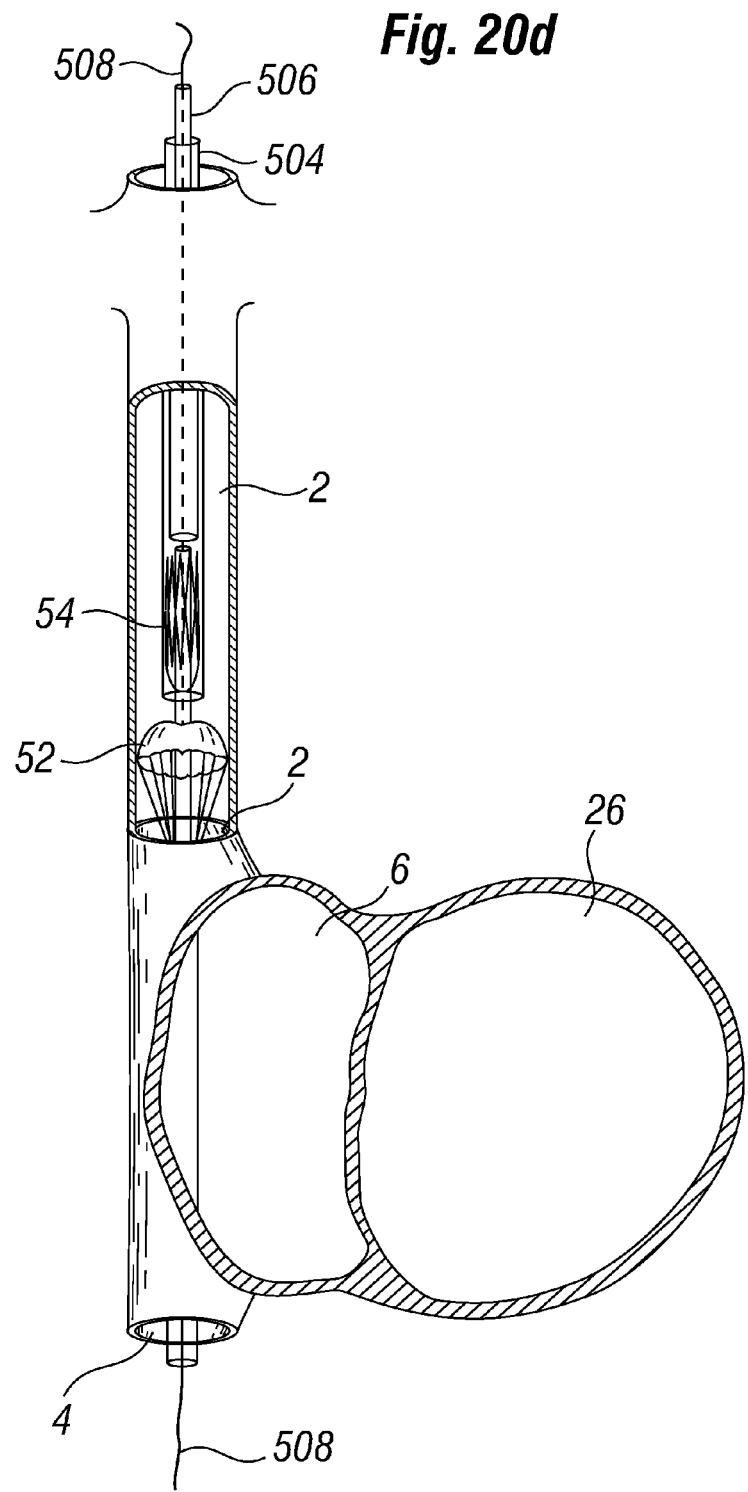
Figure 20E:
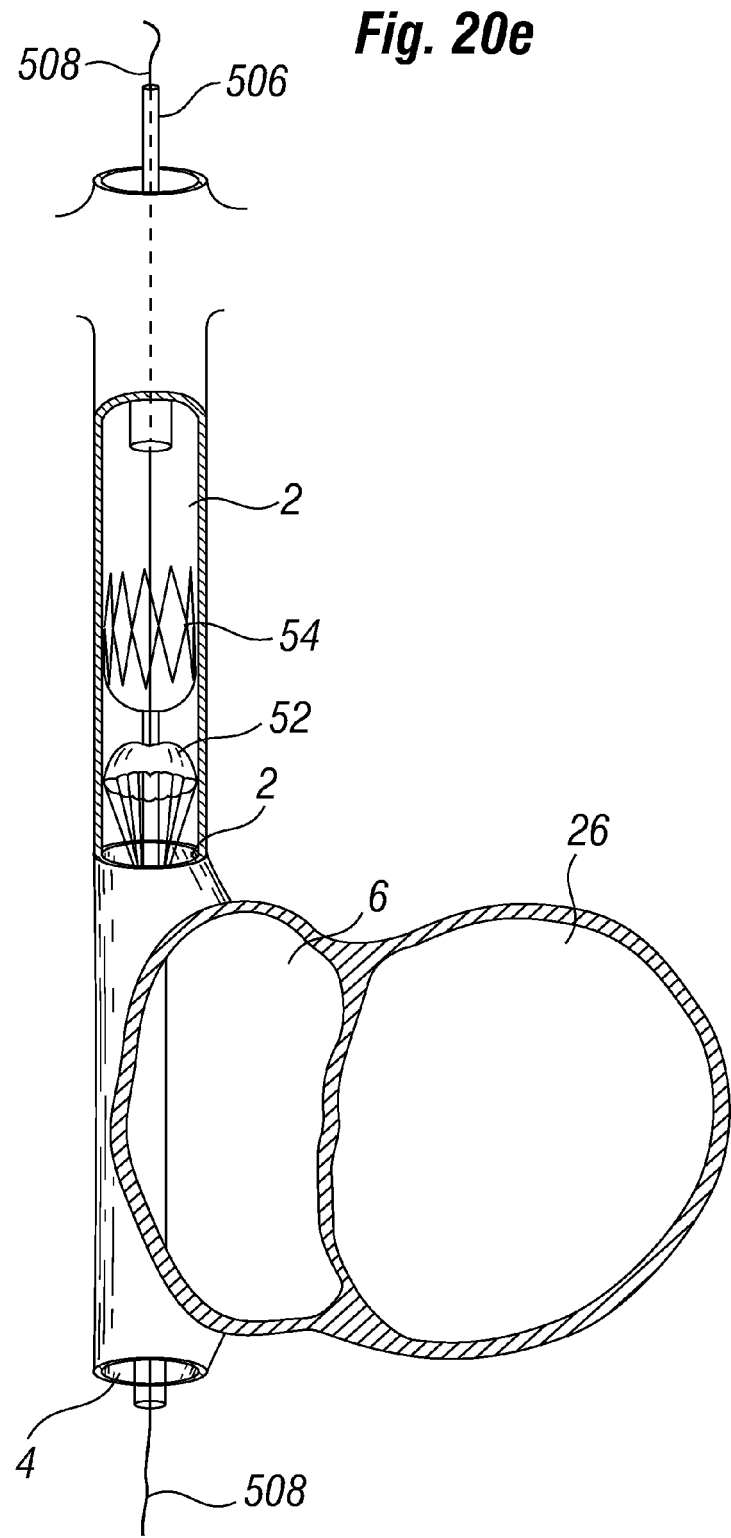

The same access route may be used for placing an apparatus 42 in the superior vena cava 2. The restraining catheter 504 and the apparatus 42 are introduced into the superior vena cava 2. The restraining catheter 504 is retracted such that the valve means 54 is released inside the superior vena cava 2, as shown in FIG. 20d. The restraining catheter 504 is withdrawn further and finally from the patient. As shown in FIG. 20e, the anchoring means 54 is deployed inside the superior vena cava 2 and the apparatus 42 is completely deployed. If the groin access to the femoral vein is used, an apparatus 42 would first be deployed in the superior vena cava 2 and an apparatus 42 would secondly be deployed in the inferior vena cava 4 using an identical method.

It should be emphasized that the preferred embodiments described herein is in no way limiting and that many alternative embodiments are possible within the scope of protection defined by the appended claims. For example, the different embodiments of the valve means and the anchoring means may be combined in any manner. Further, it would be apparent to a person skilled in the art, that other veins or arteries may be chosen in order to obtain access to the large vessels around the heart and to the different chambers of the heart.

What is claimed is:

1. A method for reducing regurgitation in a mitral valve, the method comprising:
percutaneously inserting a mitral valve flow improvement device in a compressed state into a heart, the mitral valve flow improvement device comprising an upstream end and a downstream end; a flexible prosthetic mitral valve leaflet at the upstream end; a tissue penetrating anchor at the downstream end; a connecting member extending axially therebetween, an upstream end thereof encircled by and coupled to the prosthetic mitral valve leaflet; and a plurality of flexible extending members extending from a rim of the prosthetic mitral valve leaflet to the connecting member;
anchoring the tissue penetrating anchor in a wall of the left ventricle with the prosthetic mitral valve leaflet disposed in a gap between native mitral valve leaflets;
releasing the mitral valve flow improvement device from the compressed state; and
permitting the prosthetic mitral valve leaflet to alternate between an open state and a closed state, wherein
blood flow from the left ventricle towards the left atrium expands the prosthetic mitral valve leaflet into the closed state in which the prosthetic mitral valve leaflet is umbrella-shaped, the plurality of flexible extending members limiting an upstream movement and expansion thereof, an upstream face of the prosthetic mitral valve leaflet contacts the native mitral valve leaflets in their closed positions, coapting therewith, thereby improving a seal of the mitral valve and reducing regurgitation therethrough, and
blood flow through the mitral valve from a left atrium into the left ventricle collapses the prosthetic mitral valve leaflet into the open state in which the prosthetic mitral valve leaflet is collapsed towards the connecting member, reducing a reduced radial cross section thereof and at least partially releasing contact with the native mitral valve leaflets in their open positions, thereby facilitating blood flow therearound.

2. The method of claim 1, wherein percutaneously inserting a mitral valve flow improvement device comprises percutaneously inserting the mitral valve flow improvement device into a left atrium through a right atrium and an interatrial septum.

3. The method of claim 1, wherein percutaneously inserting a mitral valve flow improvement device comprising a prosthetic mitral valve leaflet comprises percutaneously inserting a mitral valve flow improvement device comprising a prosthetic mitral valve leaflet, wherein a cross-sectional shape of the prosthetic mitral valve leaflet in the closed state is at least one of circular, oval, or rectangular.

4. The method of claim 1, wherein anchoring the tissue penetrating anchor in a wall of the left ventricle comprises engaging opposite sides of the wall of the left ventricle with disk-shaped elements.

5. The method of claim 1, wherein anchoring the tissue penetrating anchor in a wall of the left ventricle with the prosthetic mitral valve leaflet disposed in a gap between native mitral valve leaflets comprises anchoring the tissue penetrating anchor in a wall of the left ventricle with the prosthetic mitral valve leaflet disposed asymmetrically between native mitral valve leaflets.

6. A method for restoring function to a mitral valve in a human heart, comprising:
introducing a prosthesis into an interior of the heart;
securing one end of the prosthesis to tissue within a left ventricle of the heart around a vertex of the left ventricle;
positioning an opposite end of the prosthesis between opposing leaflets of the mitral valve;
expanding the prosthesis so as to place the prosthesis into contact with at least one leaflet of the mitral valve and thereby substantially prevent blood flow through the mitral valve in a first direction; and contracting the prosthesis so as to at least partially release contact between the prosthesis and the at least one leaflet of the mitral valve and to substantially allow blood flow through the mitral valve in a second direction.

7. The method of claim 6, wherein the securing of one end of the prosthesis in the left ventricle includes extending the one end of the prosthesis at least partially through heart tissue in the left ventricle.

8. The method of claim 7, wherein expanding the prosthesis to contact at least one leaflet of the mitral valve includes coapting at least one leaflet of the mitral valve with the prosthesis.

9. The method of claim 7, wherein expanding the prosthesis to contact at least one leaflet of the mitral valve includes expanding an umbrella-like flexible flap disposed at one end of the prosthesis.

10. The method of claim 9, further comprising securing a periphery of the flexible flap to the prosthesis with a plurality of flexible connecting members extending between the periphery of the flexible flap and the prosthesis.

11. The method of claim 9, wherein the contracting the prosthesis to substantially allow blood flow includes allowing the umbrella-like flexible flap to collapse.

12. A method for treating regurgitation in a mitral valve comprising:
    disposing a flexible flap between native leaflets of a mitral valve in a heart,
    wherein
    the flap collapses in response to blood flow through the mitral valve from a left atrium into a left ventricle, at least partially releasing contact with at least one native leaflet of the mitral valve in an open position, thereby facilitating blood flow therearound, and
    the flap expands into a parachute shape in response to blood flow from the left ventricle towards the left atrium, the parachute shape convex towards the left atrium and concave towards the left ventricle, a surface of the flap coapting with at least one native leaflet of the mitral valve in a closed position, thereby improving a seal of the mitral valve and reducing regurgitation therethrough.

13. The method of claim 12, further comprising anchoring the flexible flap to a wall of the heart.

14. The method of claim 13, wherein anchoring the flexible flap to a wall of the heart comprises anchoring the flexible flap to a wall of a left ventricle.

15. The method of claim 12, further comprising inserting the flexible flap into the heart percutaneously.

16. The method of claim 12, wherein disposing a flexible flap between native leaflets of a mitral valve in a heart comprises disposing the flexible flap asymmetrically between native leaflets of the mitral valve in the heart.

17. The method of claim 12, wherein the flap at least partially releasing contact with at least one native leaflet of the mitral valve in an open position comprises the flap at least partially releasing contact with two native leaflets of the mitral valve in their open positions.

18. The method of claim 12, wherein a surface of the flap coapting with at least one native leaflet of the mitral valve in a closed position comprises the surface of the flap coapting with two native leaflets of the mitral valve in their closed positions.

* * * * *